US010166355B2

(12) United States Patent
Eves et al.

(10) Patent No.: US 10,166,355 B2
(45) Date of Patent: Jan. 1, 2019

(54) NASAL MASK SYSTEM

(71) Applicant: RESMED LIMITED, Bella Vista, New South Wales (AU)

(72) Inventors: Matthew Eves, Sydney (AU); Memduh Guney, Sydney (AU); Rupert Christian Scheiner, Sydney (AU)

(73) Assignee: ResMed Limited, Bella Vista (AU)

( * ) Notice: Subject to any disclaimer, the term of this patent is extended or adjusted under 35 U.S.C. 154(b) by 488 days.

(21) Appl. No.: 14/358,482

(22) PCT Filed: Nov. 15, 2012

(86) PCT No.: PCT/AU2012/001416
§ 371 (c)(1),
(2) Date: May 15, 2014

(87) PCT Pub. No.: WO2013/071359
PCT Pub. Date: May 23, 2013

(65) Prior Publication Data
US 2014/0283843 A1    Sep. 25, 2014

(30) Foreign Application Priority Data
Nov. 15, 2011   (AU) .................................. 2011904754

(51) Int. Cl.
*A61M 16/06*       (2006.01)
*A61M 11/00*       (2006.01)
(Continued)

(52) U.S. Cl.
CPC ........ *A61M 16/0622* (2014.02); *A61M 11/00* (2013.01); *A61M 16/06* (2013.01);
(Continued)

(58) Field of Classification Search
CPC .............. A61M 16/0622; A61M 16/06; A61M 16/0616; A61M 2016/0661
See application file for complete search history.

(56) References Cited

U.S. PATENT DOCUMENTS 2,939,458 A    6/1960  Lundquist
4,907,584 A    3/1990  McGinnis
(Continued)

FOREIGN PATENT DOCUMENTS

JP    2012-527908       11/2012
WO    WO 1998/04310     2/1998
(Continued)

OTHER PUBLICATIONS

International Search Report issued in PCT Appln. No. PCT/AU2012/001416, dated Jan. 31, 2013.
(Continued)

*Primary Examiner* — Gregory Anderson
*Assistant Examiner* — Margaret Luarca
(74) *Attorney, Agent, or Firm* — Nixon & Vanderhye P.C.

(57) ABSTRACT

A mask system includes a cushion for a mask that seals at its upper extent in a region of the nose that is generally above the tip of the nose or pronasale, and extends across a portion of the cartilaginous framework, alar or flares of the patient's nose, e.g., not extending over or across the bone nasal bone of the patient's nose.

38 Claims, 44 Drawing Sheets

(51) Int. Cl.
*A61M 16/08* (2006.01)
*A61M 16/10* (2006.01)

(52) U.S. Cl.
CPC .... *A61M 16/0683* (2013.01); *A61M 16/0825* (2014.02); *A61M 16/0633* (2014.02); *A61M 16/107* (2014.02); *A61M 2202/0225* (2013.01); *A61M 2202/30* (2013.01); *A61M 2205/3569* (2013.01); *A61M 2205/3592* (2013.01); *A61M 2205/50* (2013.01); *A61M 2205/6054* (2013.01); *A61M 2205/8206* (2013.01); *A61M 2205/84* (2013.01); *A61M 2230/432* (2013.01); *A61M 2250/00* (2013.01)

(56) References Cited

U.S. PATENT DOCUMENTS

| | | | |
|---|---|---|---|
| 4,944,310 | A | 7/1990 | Sullivan |
| 4,960,121 | A | 10/1990 | Nelson et al. |
| 5,243,971 | A | 9/1993 | Sullivan et al. |
| 5,724,965 | A | 3/1998 | Handke et al. |
| 6,119,694 | A | 9/2000 | Correa et al. |
| 6,412,488 | B1 | 7/2002 | Barnett et al. |
| 6,418,928 | B1 | 7/2002 | Bordewick et al. |
| 6,494,207 | B1 | 12/2002 | Kwok |
| 6,532,959 | B1 | 3/2003 | Berthon-Jones |
| 6,581,594 | B1 | 6/2003 | Drew et al. |
| 7,210,481 | B1 * | 5/2007 | Lovell ............ A61M 16/06 128/205.25 |
| 2003/0019495 | A1 | 1/2003 | Palkon et al. |
| 2003/0196656 | A1 | 10/2003 | Moore et al. |
| 2004/0079374 | A1 | 4/2004 | Thornton |
| 2006/0118117 | A1 * | 6/2006 | Berthon-Jones ...... A61M 16/06 128/206.21 |
| 2007/0125385 | A1 * | 6/2007 | Ho ............. A61M 16/06 128/206.26 |
| 2008/0230068 | A1 | 9/2008 | Rudolph |
| 2008/0295846 | A1 | 12/2008 | Han et al. |
| 2009/0044808 | A1 | 2/2009 | Guney et al. |
| 2009/0050156 | A1 | 2/2009 | Ng et al. |
| 2009/0107504 | A1 * | 4/2009 | McAuley ............ A61M 16/06 128/205.25 |
| 2009/0139526 | A1 * | 6/2009 | Melidis ............. A61M 16/06 128/206.26 |
| 2010/0000534 | A1 | 1/2010 | Kooij et al. |
| 2011/0000492 | A1 | 1/2011 | Veliss et al. |
| 2012/0138061 | A1 * | 6/2012 | Dravitzki ............. A61M 16/06 128/205.25 |

FOREIGN PATENT DOCUMENTS

| | | |
|---|---|---|
| WO | WO 1998/34665 | 8/1998 |
| WO | WO 2000/78381 | 12/2000 |
| WO | WO 2003/090827 | 11/2003 |
| WO | WO 2005/079726 | 9/2005 |
| WO | WO 2006/074513 | 7/2006 |
| WO | WO 2007/022562 | 3/2007 |
| WO | WO 2007/045023 | 4/2007 |
| WO | WO 2007/064665 | 6/2007 |
| WO | WO 2007/145534 | 12/2007 |
| WO | WO 2008/011682 | 1/2008 |
| WO | WO 2008/011683 | 1/2008 |
| WO | WO 2008/070929 | 6/2008 |
| WO | PCT/AU2008/001557 | 11/2008 |
| WO | WO 2010/073142 | 7/2010 |
| WO | 2010/148453 | 12/2010 |
| WO | WO 2010/135785 | 12/2010 |
| WO | WO 2010/139014 | 12/2010 |
| WO | WO 2011/059346 | 5/2011 |
| WO | WO 2011/121463 | 10/2011 |
| WO | WO 2012/028995 | 3/2012 |
| WO | PCT/AU2012/001416 | 11/2012 |
| WO | WO 2013/071359 | 5/2013 |

OTHER PUBLICATIONS

Written Opinion of International Preliminary Examining Authority issued in PCT Appln. No. PCT/AU2012/001416, dated Oct. 29, 2013.
International Preliminary Report on Patentability issued in PCT Appln. No. PCT/AU2012/AU2012/001416 dated Feb. 25, 2014.
Notice of Acceptance issued in corresponding Australian Application No. 2012339622 dated Apr. 20, 2015.
Extended European Search Report issued in corresponding EP Application No. 12 85 0600.3 dated Apr. 30, 2015.
First Office Action issued in corresponding Chinese Application No. 201280067153.7 dated Aug. 24, 2015, with English translation thereof.
Second Office Action issued in corresponding Chinese Application No. 201280067153.7 dated Apr. 27, 2016, with English language translation thereof.
Further Examination Report issued in corresponding New Zealand Patent Appln. No. 624925 dated Jun. 27, 2016.
First Examination Report issued in corresponding New Zealand Patent Appln. No. 720877 dated Jun. 27, 2016.
Patent Examination Report No. 1 issued in corresponding Australian Application No. 2015205927 dated May 3, 2016.
First Examination Report issued in corresponding New Zealand Appln. No. 624925 dated Mar. 9, 2015.
Patent Examination Report No. 1 issued in corresponding Australian Appln. No. 2012339622 dated Aug. 11, 2014.
Office Action dated Feb. 16, 2017 issued in European Application No. 12850600.3 (5 pages).
Second Examination Report dated Feb. 28, 2017 issued in Australian Application No. 2015205927 (4 pages).
Communication from New Zealand Intellectual Property Office dated Mar. 7, 2017 issued in New Zealand Application No. 624925 (1 page).
Notice of Opposition to Grant of Patent (Section 21) filed Feb. 24, 2017 by Fisher & Paykel Healthcare Limited in New Zealand Application No. 624925 (2 pages).
Third Examination Report dated Apr. 19, 2017 issued in Australian Application No. 2015205927 (3 pages).
Notification of Third Office Action dated Oct. 17, 2016 issued in Chinese Application No. 201280067153.7 with English translation (4 pages).
Office Action dated Nov. 21, 2016 issued in Japanese Application No. 2014-541485 with English translation (8 pages).
Communication Regarding Deadline for Counterstatement dated Jun. 14, 2017 issued in New Zealand Application No. 624925 (2 pages).
Amended Notice of Opposition to Grant of Patent (Section 21), with no markups, dated May 29, 2017, filed by Fisher & Paykel Healthcare Limited in New Zealand Application No. 624925 (2 pages).
Amended Notice of Opposition to Grant of Patent (Section 21), with markups, dated May 29, 2017, filed by Fisher & Paykel Healthcare Limited in New Zealand Application No. 624925 (2 pages).
Statement of Case dated May 29, 2017, filed by Fisher & Paykel Healthcare Limited in New Zealand Application No. 624925 (18 pages).
Further Examination Report dated Sep. 19, 2017 issued in New Zealand Application No. 720877 (2 pages).
First Examination Report dated Dec. 18, 2017 issued in New Zealand Application No. 737918 (3 pages).
Office Action dated Jul. 23, 2018 issued in Japanese Application No. 2017-170187 with English translation (11 pages).

* cited by examiner

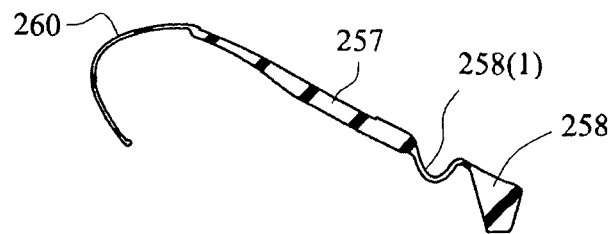
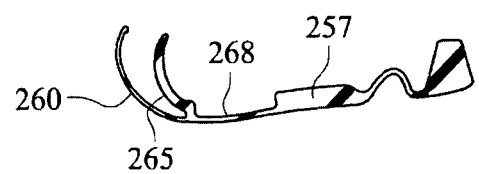
FIG. 3-23
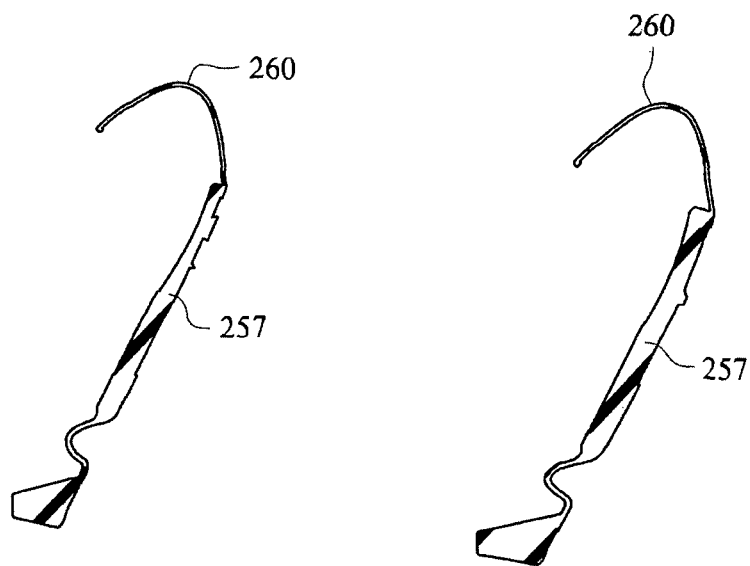
FIG. 3-24  FIG. 3-25

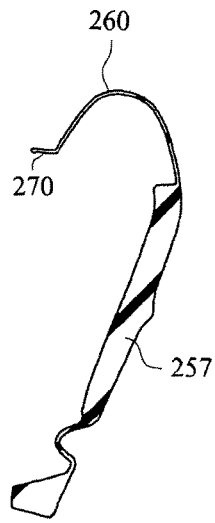 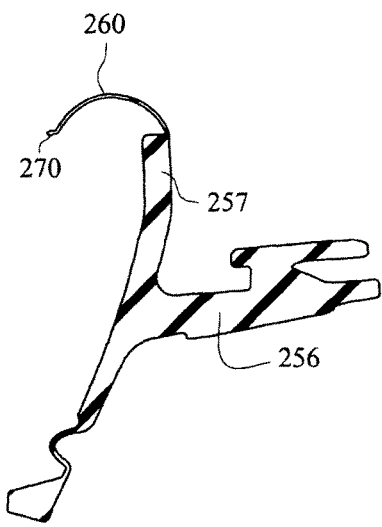
FIG. 3-26  FIG. 3-27
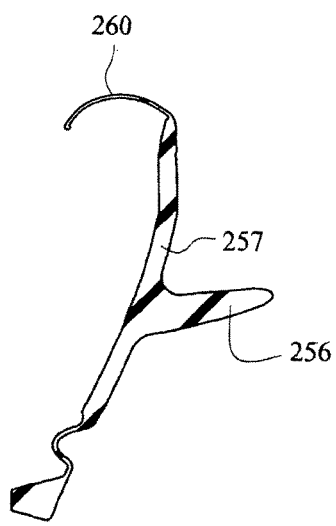 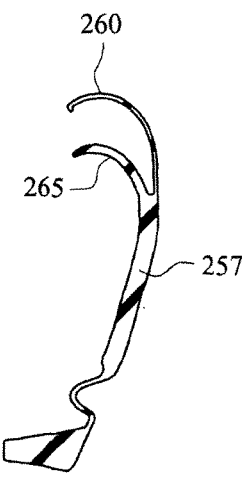 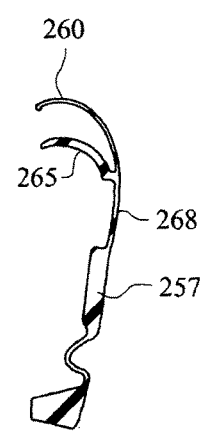
FIG. 3-28   FIG. 3-29   FIG. 3-30

NASAL MASK SYSTEM

CROSS-REFERENCE TO RELATED APPLICATIONS

This application is the U.S. national phase of International Application No. PCT/AU2012/001416 filed 15 Nov. 2012 which designated the U.S. and claims priority to Australian Provisional Application No. AU 2011904754, filed Nov. 15, 2011, the entire contents of each of which are incorporated herein by reference in its entirety.

STATEMENT REGARDING FEDERALLY SPONSORED RESEARCH OR DEVELOPMENT

Not Applicable

THE NAMES OF PARTIES TO A JOINT RESEARCH DEVELOPMENT

Not Applicable

SEQUENCE LISTING

Not Applicable

BACKGROUND OF TECHNOLOGY

(1) Field of Technology

The present technology relates to treatment of respiratory disorders, and to procedures to prevent respiratory disorders. In particular, the present technology relates to medical devices, and their use for treating respiratory disorders and for preventing respiratory disorders. More particularly, the present technology relates to a nasal mask system used for treatment, e.g., of Sleep Disordered Breathing (SDB) with Continuous Positive Airway Pressure (CPAP) or Non-Invasive Positive Pressure Ventilation (NIPPY).

(2) Description of the Related Art

The respiratory system of the body facilitates gas exchange. The nose and mouth form the entrance to the airways of a patient.

The airways consist of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnoea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnoea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnoea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, NMD and Chest Wall disorders.

Patient Interface

The application of a supply of air at positive pressure to the entrance of the airways of a patient, e.g., while a patient sleeps, is facilitated by the use of a patient interface, such as a nasal mask, full-face mask or nasal pillows.

Known patient interface devices suffer from being one or more of obtrusive, aesthetically undesirable, poorly fitting, difficult to use and uncomfortable, especially when worn for long periods of time or when a patient is unfamiliar with a system.

Seal-Forming Portion

Patient interfaces typically include a seal-forming portion.

A range of patient interface seal-forming portion technologies are disclosed in the following patent applications, assigned to ResMed Limited: WO 1998/004,310; WO 2006/074,513; WO 2010/135,785.

Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses.

Vent Technologies

Some forms of patient interface systems may include a vent to allow the washout of exhaled carbon dioxide.

ResMed Limited has developed a number of mask vent technologies. See WO 1998/034,665; WO 2000/078,381; U.S. Pat. No. 6,581,594; US Patent Application; US 2009/0050156; US Patent Application 2009/0044808.

BRIEF SUMMARY OF TECHNOLOGY

The present technology is directed towards providing medical devices used in the diagnosis, treatment or prevention of respiratory disorders having one or more of improved comfort, cost, efficacy, ease of use and manufacturability.

A first aspect of the present technology relates to apparatus used in diagnosis, treatment or prevention of a respiratory disorder.

Another aspect of the present technology relates to methods used in diagnosis, treatment or prevention of a respiratory disorder.

One aspect of the present technology is a patient interface that is one or more of comfortable, effective, simple to use, unobtrusive and with a wide fit range.

An aspect of one form of the present technology is a patient interface that avoids a jetting effect of nasal pillows or prongs, and/or a feeling of discomfort from locating a portion of a mask within a nasal cavity of a patient.

An aspect of one form of the present technology is a nasal mask that is easy to put on, and may avoid a need for headgear straps to interfere with, or cross the ears in use, and may avoid interfering or crossing the ears while putting on or removing.

Another aspect of one form of the present technology is a method of putting on or removing a mask.

In one form of the present technology, a small, unobtrusive nasal mask is provided.

In one form of the present technology, a nasal mask is provided that does not form a seal on a lower lip, or a chin of a patient.

In one form of the present technology, a patient interface is provided that does not exert a rearward force on the mandible, e.g. the patient interface does not push on the mandible from the anterior towards the posterior.

In one form of the present technology, a patient interface is provided that does not comprise a rigid shell or rigid frame.

In one form of the present technology, a patient interface is provided that comprises a plenum chamber constructed from a flexible or semi-rigid material, for example a flexible rubber of a suitable thickness (e.g. silicone with a type A hardness in the range of about 35 to about 45, and about 1.5 mm to about 3 mm thick).

In one form of the technology, a nasal mask is provided that does not require engagement or disengagement of a clip to don or remove the mask.

An aspect of one form of the present technology is a patient interface comprising a seal-forming portion having a first sealing region that is constructed to have little nor no resistance to compression, and a second sealing region that is constructed to substantially resist a compressive force (e.g. as a result of headgear tension). In an example in use, the first sealing region is arranged to overlay a portion of the cartilaginous framework of the nose, and the second sealing region is arranged to overlay a portion of a bone region the face. In an example, the bone region of the face is a region adjacent the ala, and optionally adjacent to the alar crest point.

According to one form of the present technology, a patient interface is provided that comprises: (i) a seal-forming portion that in use overlays at least part of a top lip region of a patient's face, and a portion of the cartilaginous framework of the nose; and (ii) a seal positioning and stabilising structure that may be donned and removed without interfering with the ears of the patient.

Another aspect of one form of the present technology is a patient interface having a seal-forming portion associated with a two point connection with a seal positioning and stabilising structure. In an example, the patient interface does not comprise a forehead support. In an additional or alternative example, the seal positioning and stabilising structure comprises a non-rigid or flexing connection element.

Another aspect of one form of the present technology is a patient interface that is moulded or otherwise constructed with a clearly defined perimeter shape which is intended to match that of an intended wearer in use.

Another aspect of one form of the present technology is a patient interface that is constructed and arranged so that while forming a seal on at least part of the cartilaginous framework of the nose, it avoids or reduces a tendency to restrict nasal air flow therethrough.

According to one form of the present technology, a patient interface is provided that comprises a first superior sealing portion that in use overlays a portion of the cartilaginous framework of the nose, and a second inferior sealing portion that in use overlays a portion of the upper lip and wherein in use, a relatively larger portion of a headgear sealing force is directed towards the portion of the upper lip and the underlying maxilla, teeth or gum than is directed towards the cartilaginous framework of the nose.

Another aspect of one form of the present technology is a patient interface that is constructed and arranged to avoid or reduce a tendency to put unnecessary pressure on the nasal septum.

According to one form of the present technology, a patient interface is provided that in use forms a seal on a portion of an upper lip of a patient, and which comprises a plenum chamber having a wall and wherein a first portion of the wall that is constructed to be located adjacent the septum in use has a relatively less stiff spring constant that portions of the wall that are adjacent to said first portion.

Another aspect of one form of the present technology is a patient interface that while forming a seal on a portion of the cartilaginous framework of the nose, provides an effective or improved seal on the region of the nose near a junction between the greater alar cartilage and the lateral cartilage.

According to one form of the present technology, a patient interface is provided that comprises a sealing flange that defines a generally T-shaped, or three lobed orifice. In an example, the sealing flange includes a membrane and a sealing flap that protrudes from the edge of the membrane along its inner perimeter in each side of nose region. The edge of the membrane along its inner perimeter along with the edge of each sealing flap along its inner perimeter cooperate to define an orifice into the plenum chamber. In an example, such orifice includes a general T-shape, or three lobed orifice, including an upper orifice portion (along vertical axis v as viewed in FIG. 3-20) and a lower orifice portion (along horizontal axis h as viewed in FIG. 3-20) that extends generally transverse to the upper orifice portion.

According to one form of the present technology, an inner edge of a sealing flange is spring biased towards the face of a wearer in use, e.g. with respect to a middle portion of the sealing flange.

Another aspect of one form of the present technology is a nasal mask that is constructed and arrange to pivot or rotate about a top lip region upon adjustment of a headgear tension.

Another aspect of one form of the present technology is a method of manufacturing a patient interface.

Another aspect of one form of the present technology is a device for preventing, treating or ameliorating one or more of OSA, CSA, OHS, COPD, NMD and chest-wall disorders.

Another aspect of the present technology is a mask system that can accommodate a wide range of different facial shapes including faces with high and low nose bridge regions, and narrow and wide noses. Another aspect of the present technology is a mask system with a wide fit range.

Another aspect of one form of the present technology is a mask system that is small and unobtrusive, and yet is stable on the face while a patient is sleeping.

One aspect of the present technology is a mask that is constructed and arranged to seal at its upper extent on a region of the nose that is generally above or superior to the pronasale, or tip of the nose.

One aspect of one form of the present technology is a mask that is constructed and arranged to seal at its upper extent at locations that are generally below or inferior to the nasal bones.

In one form of the present technology, a mask is provided that is constructed and arranged to have a seal forming portion that overlays a portion of the upper or superior lip, and that overlays a portion of the cartilaginous framework of the nose, e.g., without overlaying the nasal bones.

In one form of the present technology a mask is provided that is constructed and arranged to have a first seal forming portion that overlays a portion of the upper or superior lip, and a second seal-forming portion that overlays of the cartilaginous framework of the nose, e.g., without overlaying the nasal bones.

In one form of the present technology a mask is provided that is constructed and arranged to have a first seal forming portion that is substantially in compression, or subject to bending forces in use, and a second seal-forming portion that is substantially in tension in use.

In one form of the present technology a mask is provided that is constructed and arranged to have a first seal forming portion that is relatively stiff before use, and a second seal-forming portion that is relatively floppy before use.

Another aspect of one form of the present technology is a mask system with an improved sealing cuff. In an example, the mask system includes a facial flap comprising a relatively thin member formed of a flexible, e.g., and at least semi-resilient, material. In an example, the mask system further comprises, in at least some regions, a back-up band.

Another aspect of the present technology is a mask that is formed, moulded or otherwise constructed with a clearly defined perimeter shape which is intended to match that of an intended wearer.

A further aspect of the present technology is a cushion for a mask that seals at its upper extent in a region of the nose that is generally superior to or above the pronasale or tip of the nose, and extends across the alar or flares of the patient's nose.

A further aspect of the present technology is a cushion for a mask that seals at its upper extent in a region of the nose that is generally superior to or above the pronasale or tip of the nose, and extends across the alar or flares of the patient's nose, e.g., not extending over or across the nasal bones of the patient's nose.

One aspect of one form of the present technology is a cushion for a mask that seals at its upper extent in a region of the nose that is generally close to the junction between bone and cartilage on a range of people with larger noses, and which avoids impinging on the sight of people with smaller noses.

In one form of the present technology, a mask system is provided that does not require a rigid frame or skeleton, and which seals at its upper extent in a region of the nose that is generally above or superior to the pronasale, or tip of the nose.

One aspect of the present technology is a cushion for a mask that includes a sealing membrane and a backup band or undercushion, in at least some regions.

Another aspect of the present technology is a cushion for a nasal mask that includes an undercushion or backup band in the region of the top lip.

Another aspect of one form of the present technology is a cushion for a nasal mask that includes an undercushion or backup band in the region of the top lip, and no undercushion or backup band in the sides of the nose or ridge of the nose regions to avoid relatively high sealing forces on the sides of the nose or ridge of the nose regions as these relatively high sealing forces may cause occlusion of the nasal airway.

Another aspect of the present technology includes a cushion for a nasal mask, the cushion having a sealing region, a side wall region and an attachment region, wherein the sealing region is, adapted to form a seal with a patient, the side wall region connects the sealing region and attachment region, and the attachment region is adapted to connect or otherwise attach to an air delivery system.

Another aspect of the present technology includes a cushion for a nasal mask, the cushion having a sealing region and an attachment region, wherein the attachment region comprises a decoupling element.

Another aspect of the present technology includes a cushion for a nasal mask, the cushion having a sealing region and an attachment region, wherein the attachment region comprises a decoupling element, the decoupling element comprising a relatively thinner wall section. For example, the relatively thinner wall section may be 50-85% thinner.

Another aspect of the present technology includes a cushion for a nasal mask, the cushion comprising headgear connectors integrally formed with a side wall, e.g., wherein the side wall is constructed of a flexible elastomer or rubber.

Another aspect of the present technology includes a cushion for a nasal mask, the cushion comprising headgear connectors, the headgear connectors constructed and arranged to position a portion of a sealing region superior to or above the pronasale or tip of the patient's nose.

Another aspect of the present technology includes a cushion for a nasal mask, the cushion having a nose ridge region, the nose ridge region having a dip or curvature, e.g. a local saddle region, adapted to conform to, or be complementary to the nose ridge of the patient.

A further aspect of the present technology includes a cushion for a nasal mask, the cushion having a nose ridge region, the nose ridge region having a relatively longer membrane length when compared to other regions of the cushion, the relatively longer membrane length adapted to engage a greater fit range of patient's nose ridge heights.

Another aspect of the present technology includes a cushion for a nasal mask, the cushion having a sides of the nose region, the sides of the nose region having a raised portion, the raised portion having a greater height when compared to the nose ridge region, the raised portion adapted to engage with the sides of the patient's nose and ensure engagement with tall nose ridges as well as flat nose ridges.

Another aspect of the present technology includes a cushion for a nasal mask, the cushion having a corners of the nose region, generally corresponding to the region of the face between and including the subalare and the alar crest, the corners of the nose region having the greatest height when compared to all other regions of the cushion, wherein the corners of the nose region anchors the cushion in position. The height of the corners of the nose region may be arranged to ensure seal in the corners of the nose, as this is a particularly difficult area of the face to seal on.

Another aspect of the present technology includes a cushion for a nasal mask, the cushion having a top lip region, the top lip region configured to conform to the curvature of a patient's top lip region. The top lip region may be generally rounded, extending from a trough or dip and continuing up to the sides of the nose region. The membrane at the top lip region may stretch across a patient's top lip to ensure a seal with the patient's top lip.

Another aspect of the present technology relates to a nasal mask system including a cushion assembly including a sealing region that provides a single orifice adapted to surround both nares of the patient's nose and a headgear assembly including a pair of side straps and a rear strap. The side straps are adapted to extend along sides of the patient's face between the patient's eyes and ears and engage respective headgear connectors provided to the cushion assembly to provide a two-point connection with the cushion assembly. The rear strap extends between the side straps and is adapted to engage along the back or posterior of the patient's head along, below or inferior to the occipital bone.

Another aspect of the present technology relates to a nasal mask system including a cushion assembly including a sealing region having a nose ridge region, sides of nose region, corners of nose region, and a top lip region adapted to seal around both nares of the patient's nose. The nose ridge region is adapted to be positioned and seal along a nasal cartilage region which is above or superior to the pronasale and below or inferior to a nasal bone region of the patient's nasal bridge. In one form, the sealing region includes a membrane seal that extends around an entire perimeter of the sealing region and an undercushion that is only provided in the top lip and corners of nose regions.

Another aspect of the present technology relates to a nasal mask system including a cushion assembly including a sealing region adapted to seal around both nares of the patient's nose, an attachment region adapted to receive an elbow assembly, and a side wall region extending between the sealing region and the attachment region. The sealing region has a nose ridge region, sides of nose region, corners of nose region, and a top lip region. The side wall region includes an area adjacent the top lip region of the sealing region that includes a thickness that is less than corresponding thicknesses adjacent the nose ridge, sides of nose, and corners of nose regions of the sealing region.

Another aspect of the present technology relates to a nasal mask system including a cushion assembly including a sealing region having a nose ridge region, sides of nose region, corners of nose region, and a top lip region adapted to seal around both nares of the patient's nose. The sides of nose region includes a portion adapted to be positioned and seal along a region adjacent the junction between the nasal greater alar cartilage and the lateral nasal cartilage of the patient's nose.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure includes a pair of side straps that provide a two-point connection to the nasal mask and being constructed and arranged to be donned or removed without the side straps passing inferior to the patient's ears.

Another aspect of the present technology relates to a method for fitting a patient interface to a patient. The method includes positioning a sealing region of the patient interface with respect the patient's nose such that the sealing region surrounds both nares and engaging headgear straps of the patient interface with the patient's head without passing straps inferior to the patient's ears.

Another aspect of the present technology relates to a nasal mask for delivery of a supply of air to the entrance of a patient's airways. The nasal mask includes a superior sealing portion and an inferior sealing portion. The superior sealing portion is constructed and arranged to be located on a portion of the cartilaginous framework of the nose, and to form a seal therewith without exerting a sealing force that would restrict a flow of air through the nasal cavity. The inferior sealing portion is constructed and arranged to be located in part on a portion of an upper lip of a patient and to direct a sealing force to a portion of a maxilla bone of the patient.

Another aspect of the present technology relates to a nasal mask defining a breathing chamber for delivery of a supply of gas at positive pressure to the airways of a patient. The nasal mask includes a vent ad a cushion. The vent is adapted to exhaust breathable gas and is adapted to be sufficiently rigid to avoid collapse. The cushion includes a sealing cuff and headgear connectors. The sealing cuff comprises a membrane seal and an undercushion. The membrane seal extends about a perimeter of the cushion including a nose ridge region of the cushion and a side of the nose region of the cushion, and the undercushion is located in a top lip region of the cushion and does not extend to the nose ridge region of the cushion or the side of the nose region of the cushion. The headgear connectors are formed with a side wall of the cushion.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure provides a sealing vector oriented at an angle with respect to a Frankfort horizontal direction. The positioning and stabilising structure includes a two-point connection to the nasal mask.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure provides a scaling vector oriented at an angle with respect to a Frankfort horizontal direction. The nasal mask does not include a forehead support.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure provides a sealing vector oriented at an angle with respect to a Frankfort horizontal direction. The positioning and stabilising structure includes a pair of side straps adapted to extend towards and over a crown of the patient's head.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

Treatment Systems

Therapy

Respiratory System

Figure 2A:
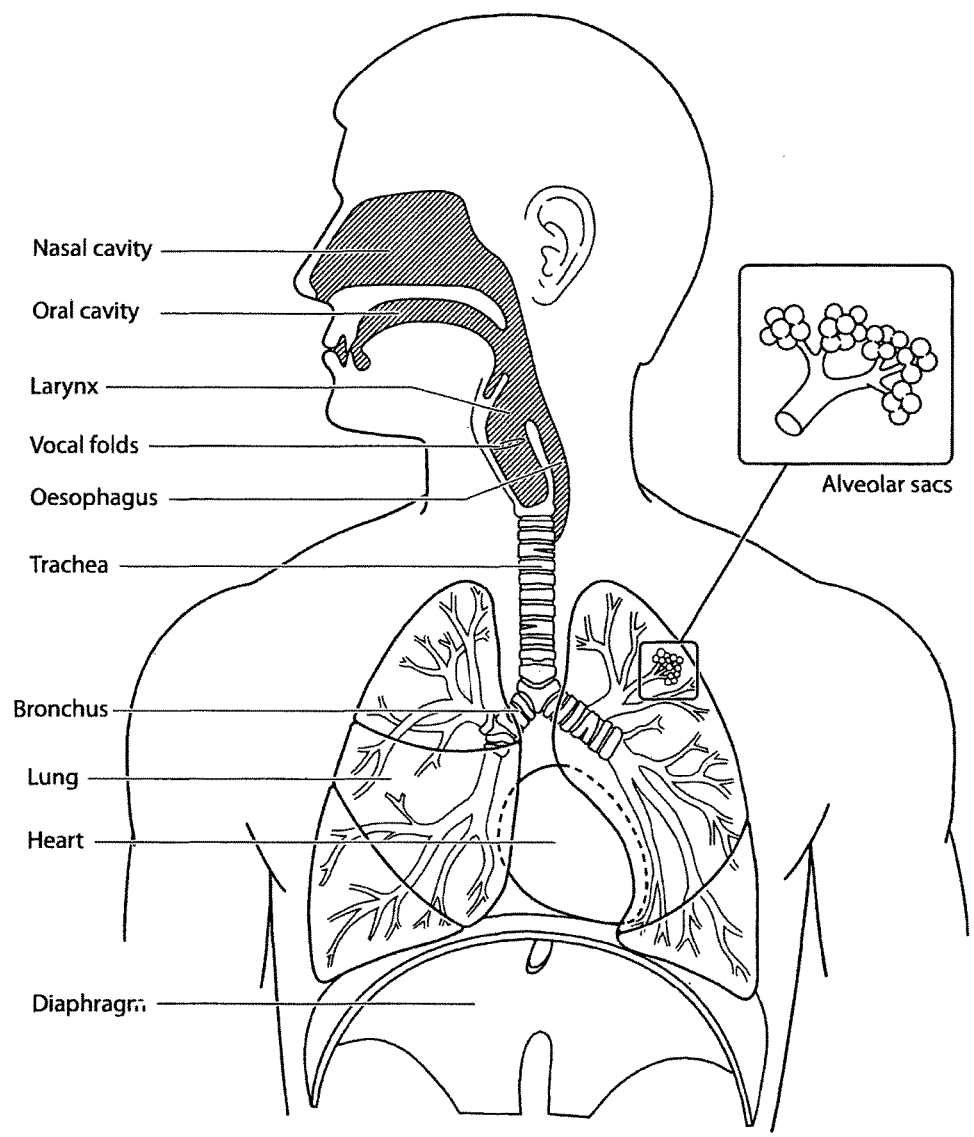

FIG. 2a shows an overview of a human respiratory system including the nasal and oral cavities, the larynx, vocal folds, oesophagus, trachea, bronchus, lung, alveolar sacs, heart and diaphragm.

Figure 2B:
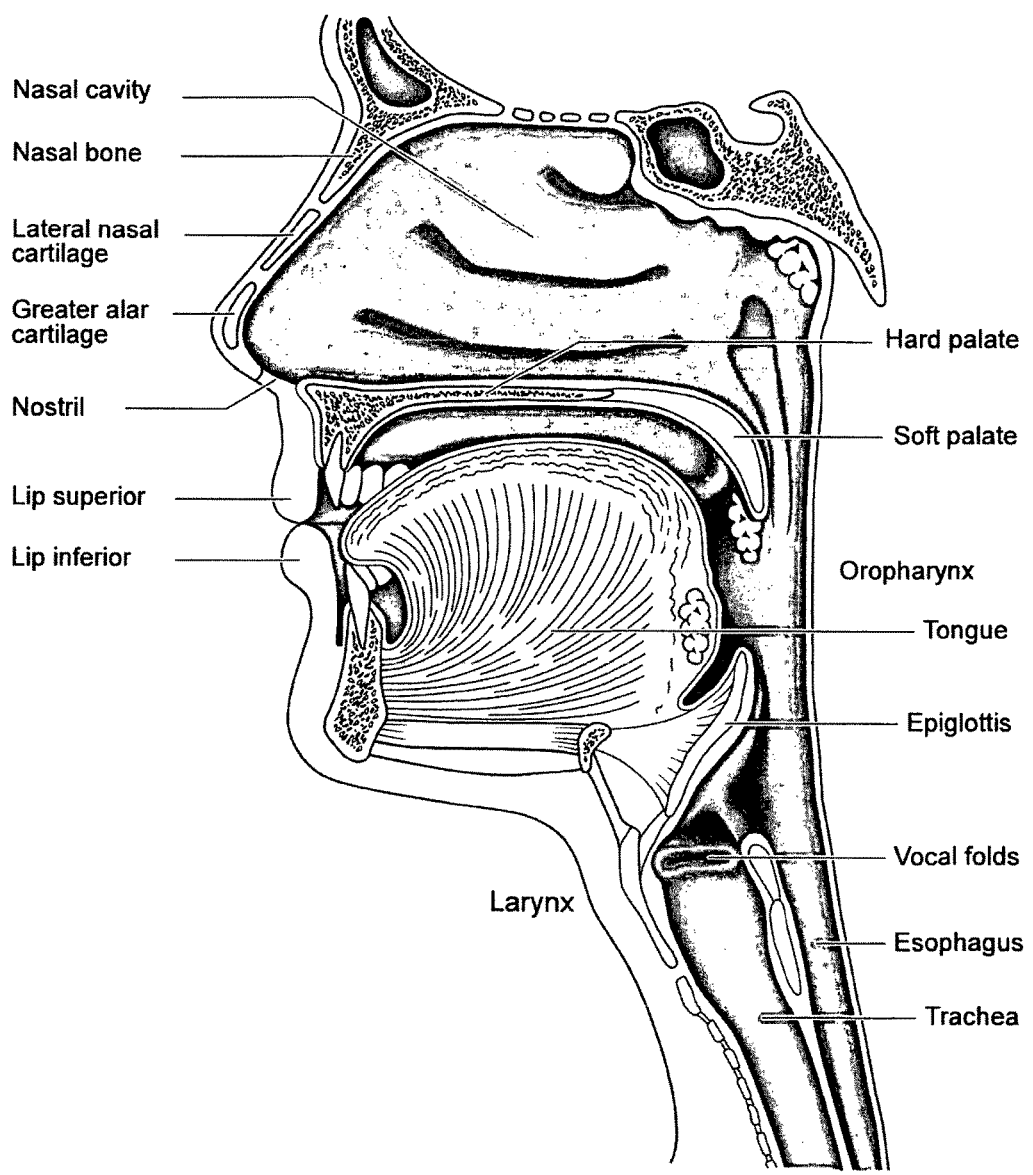

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Facial Anatomy

Figure 2C:
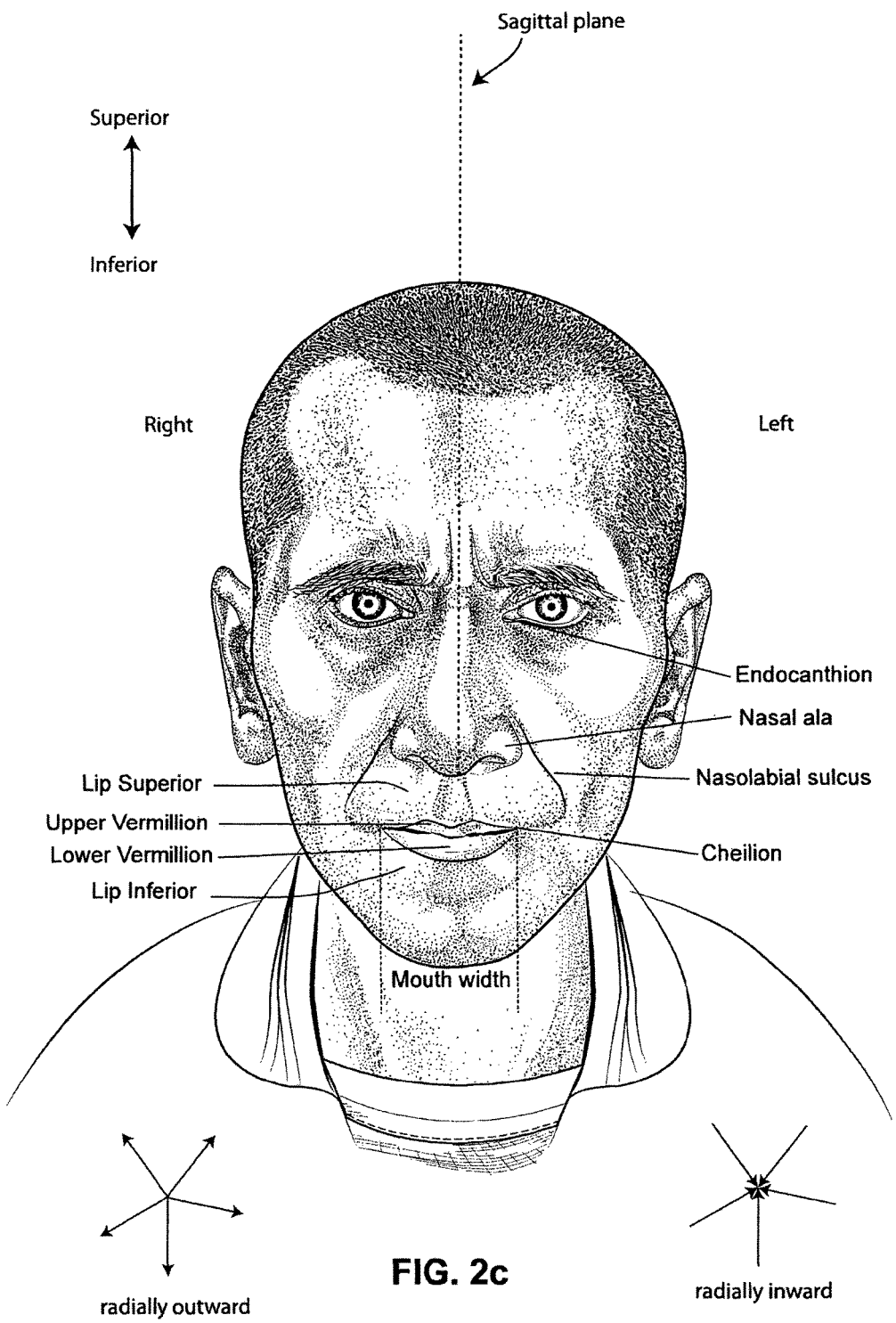

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
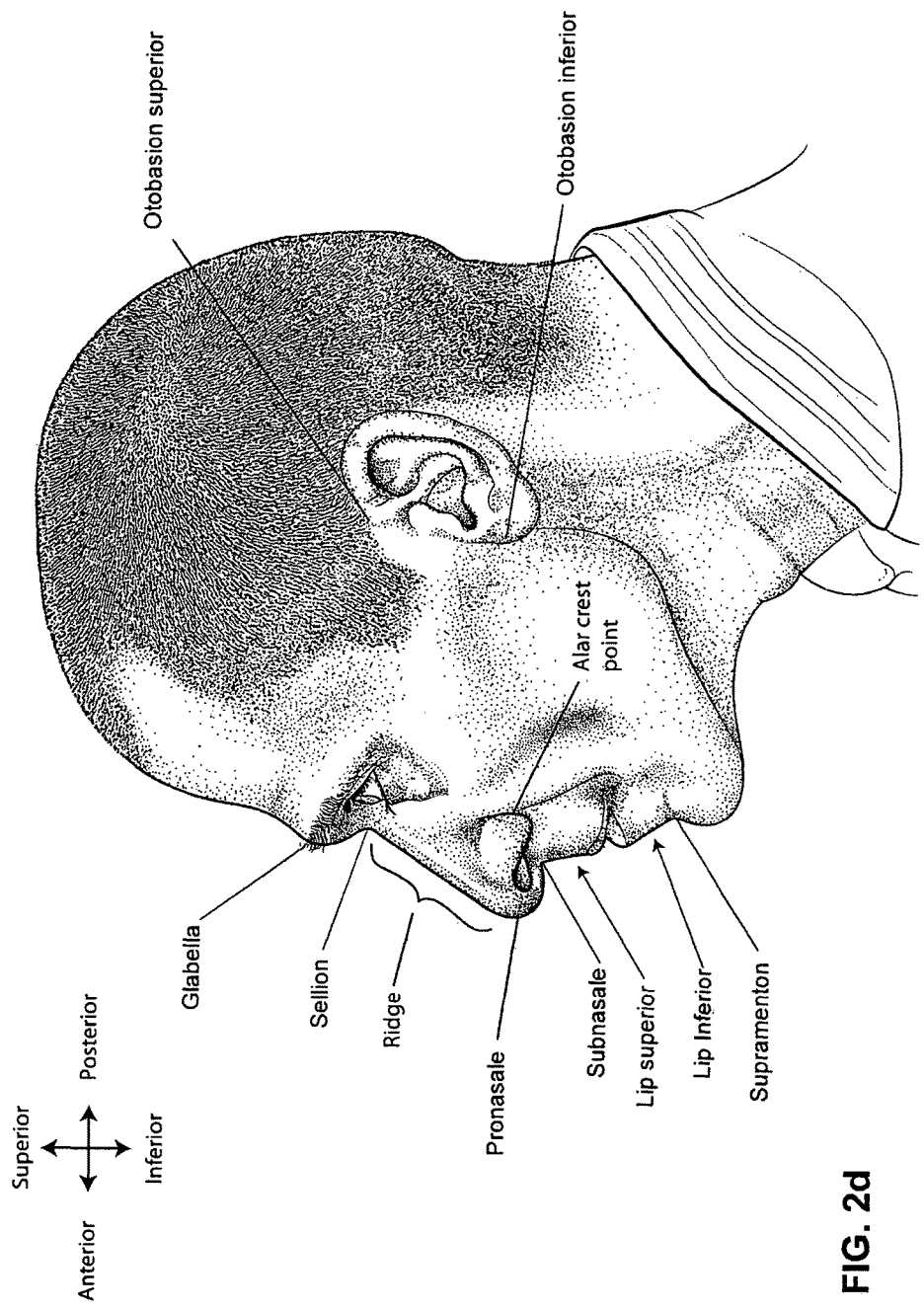

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
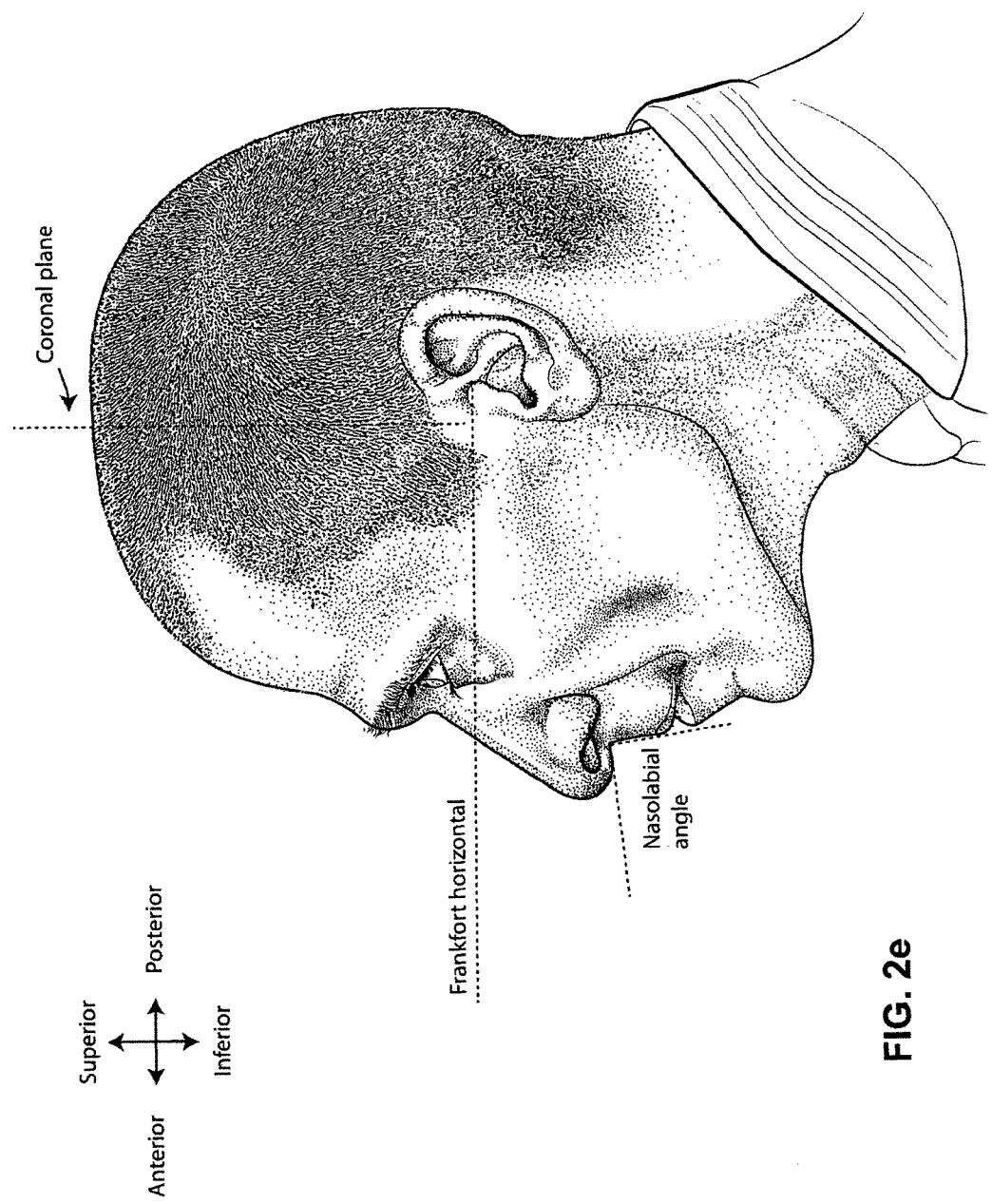

FIG. 2e is a further side view of a head. The approximate locations of the Frankfort horizontal and nasolabial angle are indicated.

Figure 2F:
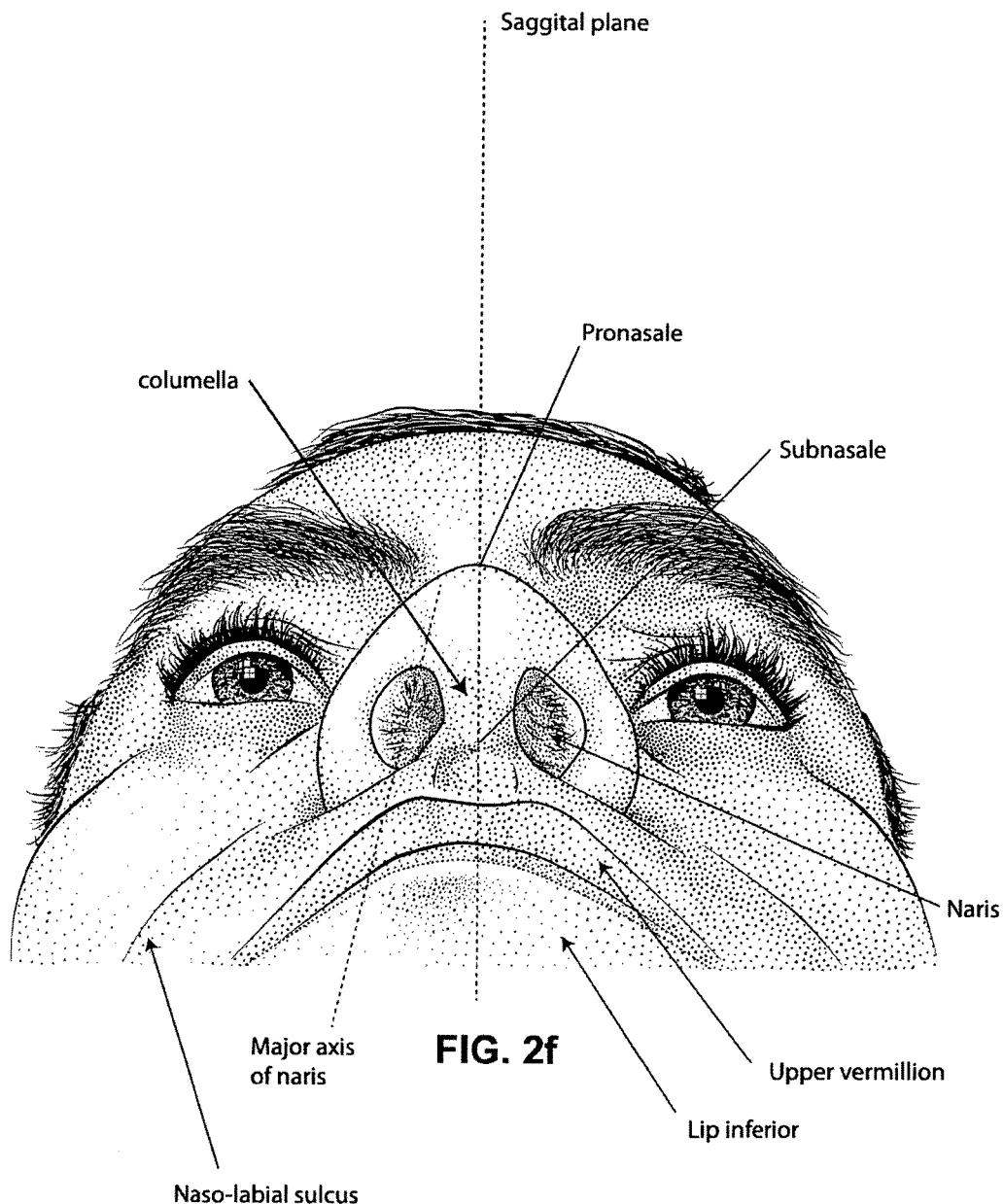

FIG. 2f shows a base view of a nose.

Figure 2I:
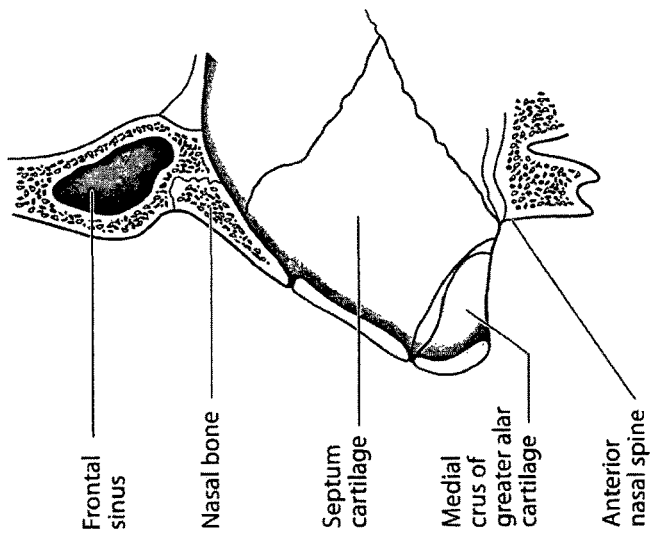
Figure 2H:
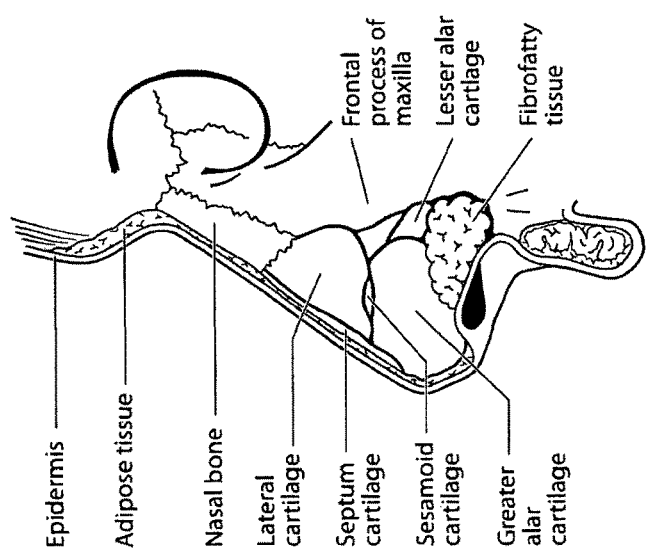
Figure 2G:

FIG. 2g shows a side view of the superficial features of a nose.

FIG. 2h shows subcutaneal structures of the nose, including the cartilaginous framework comprising the lateral cartilage, septum cartilage, greater alar cartilage, lesser alar cartilage and also shows the fibrofatty tissue.

FIG. 2i shows a medial dissection of a nose, approximately several millimeters from a sagittal plane, amongst other things showing the septum cartilage and medial crus of greater alar cartilage.

Figure 2K:
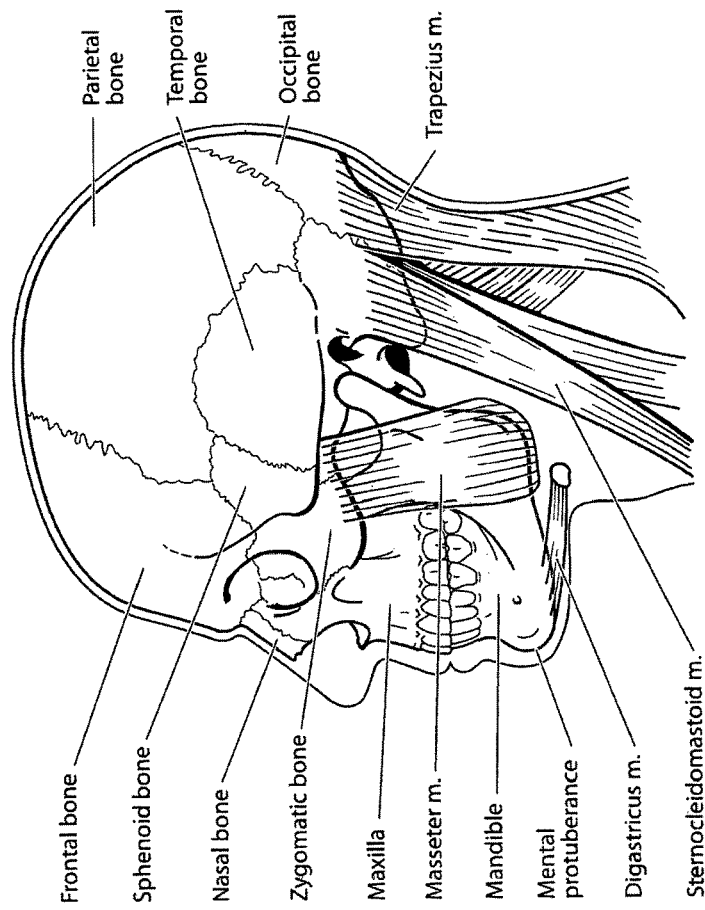
Figure 2J:
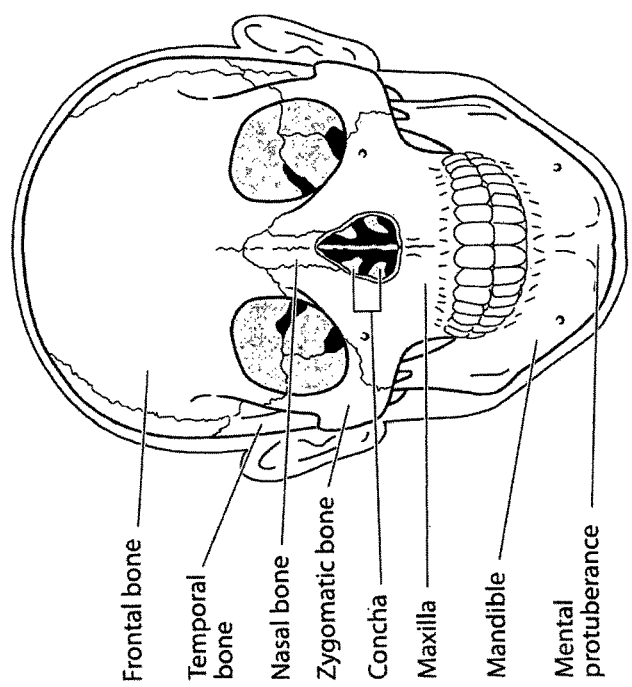

FIG. 2j shows a front view of the bones of a skull including the frontal, temporal, nasal and zygomatic bones. Nasal concha are indicated, as are the maxilla, mandible and mental protuberance.

FIG. 2k shows a lateral view of a skull with the outline of the surface of a head, as well as several muscles. The following bones are shown: frontal, sphenoid, nasal, zygomatic, maxilla, mandible, parietal, temporal and occipital.

The mental protuberance is indicated. The following muscles are shown: digastricus, masseter sternocleidomastoid and trapezius.

Patient Interface

Figures 1, 3:
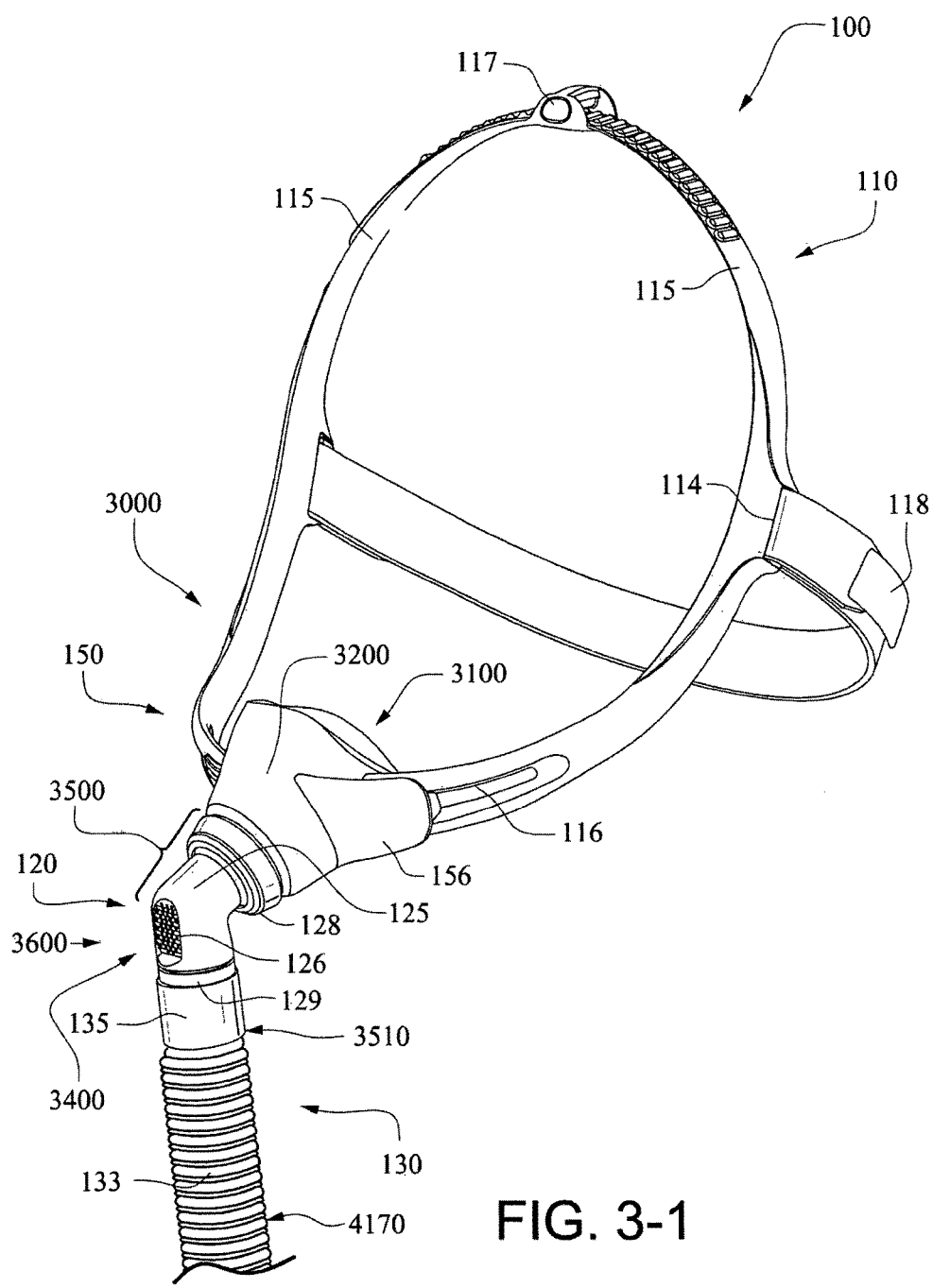

FIG. 3-1 is a perspective view of a nasal mask system according to an example of the present technology.

Figures 2, 3:
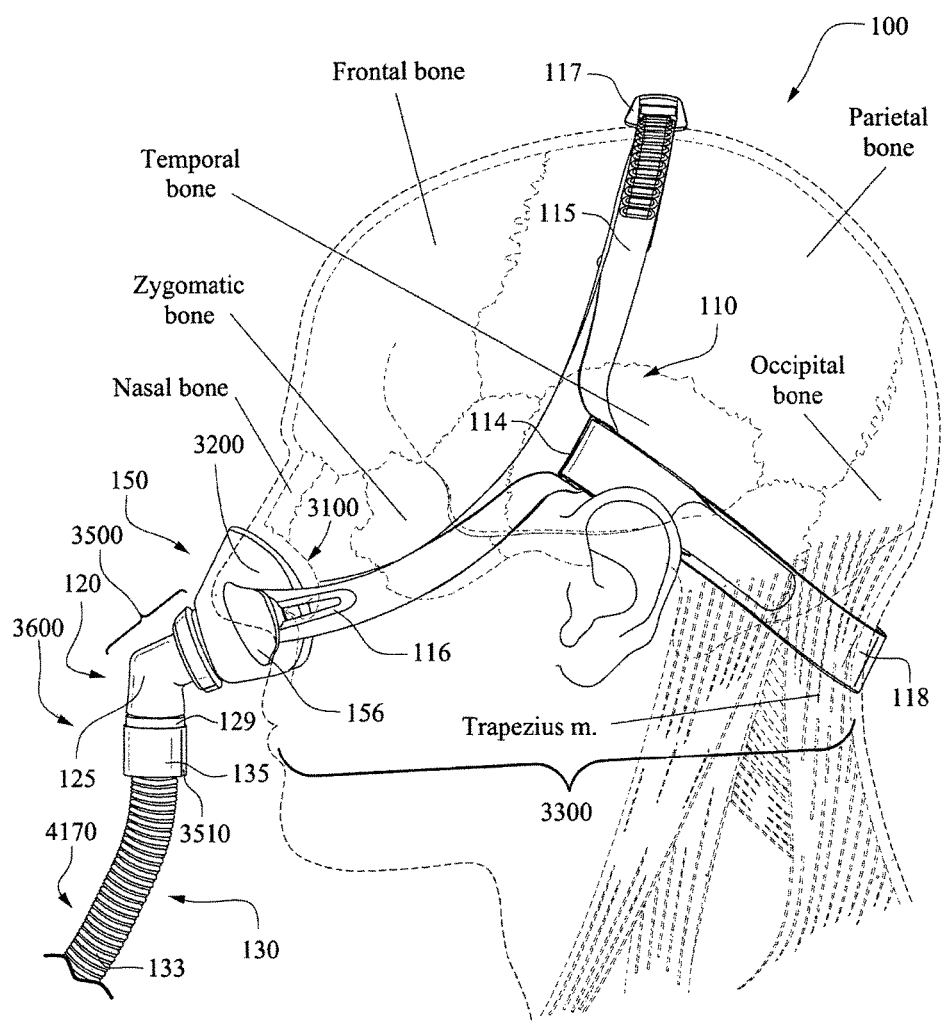
Figure 3:
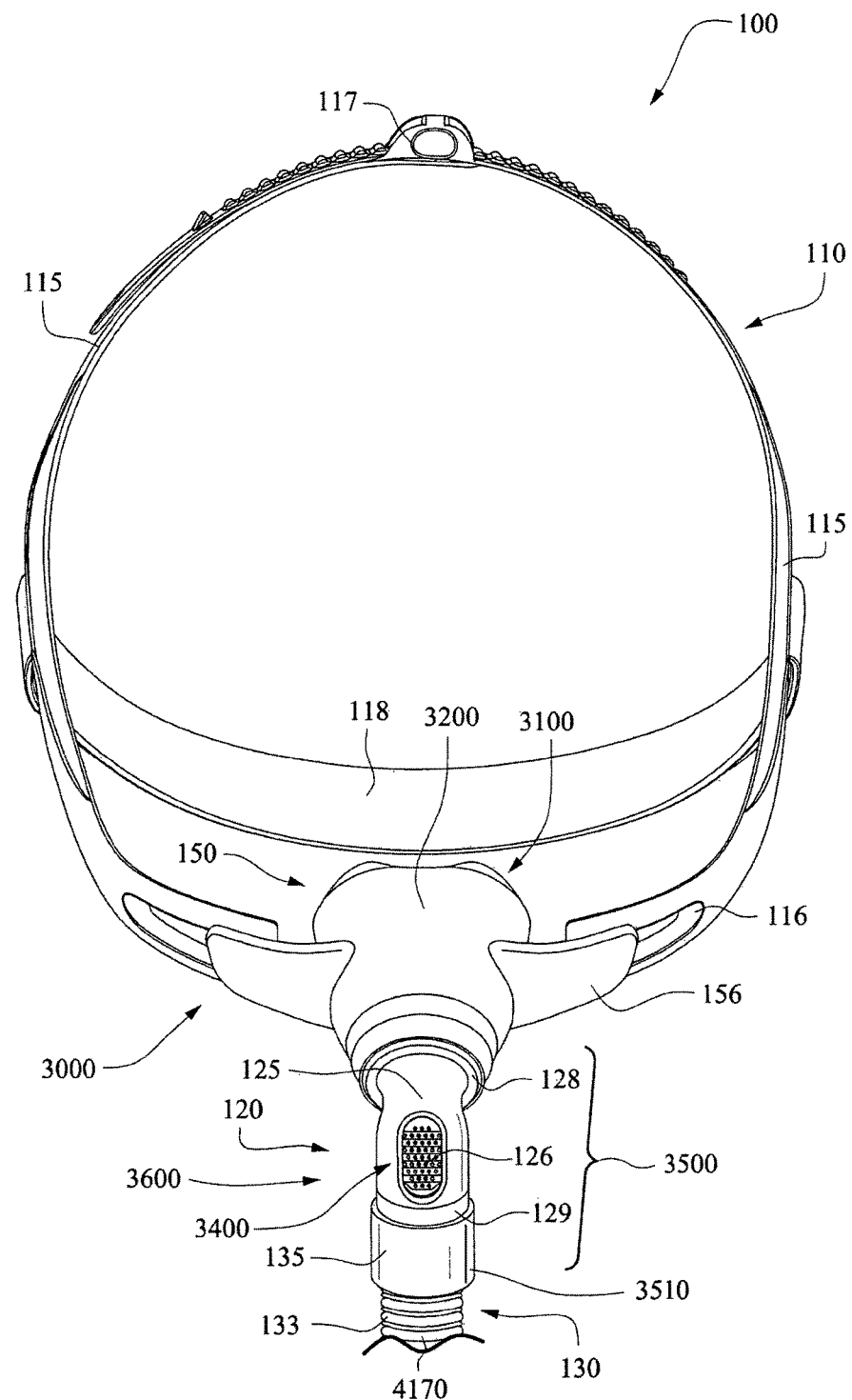

FIG. 3-2 is a side view of a nasal mask system according to an example of the present technology. The nasal mask system is shown overlaying a head to indicate the approximate relative location of the headgear in use.

FIG. 3-3 is a front view of a nasal mask system according to an example of the present technology.

Figures 3, 4:
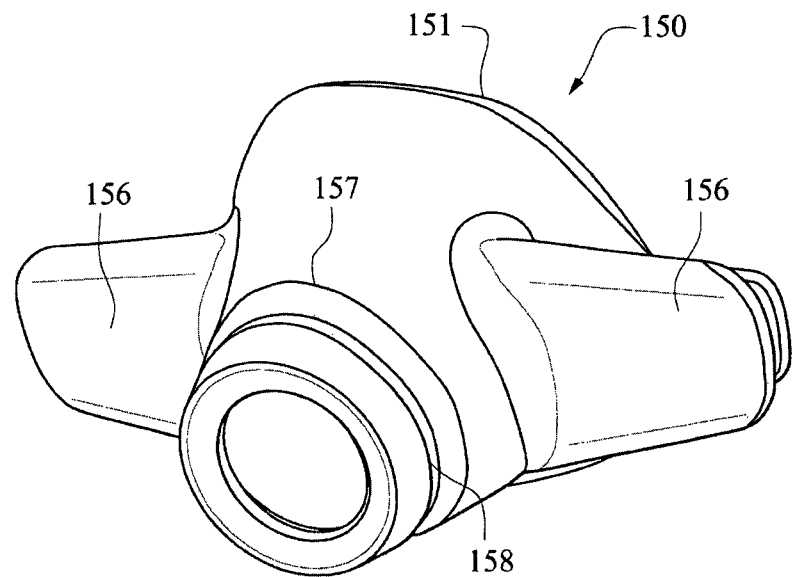

FIG. 3-4 is a perspective front view of a cushion of a nasal mask system according to an example of the present technology.

Figures 3, 4, 5:
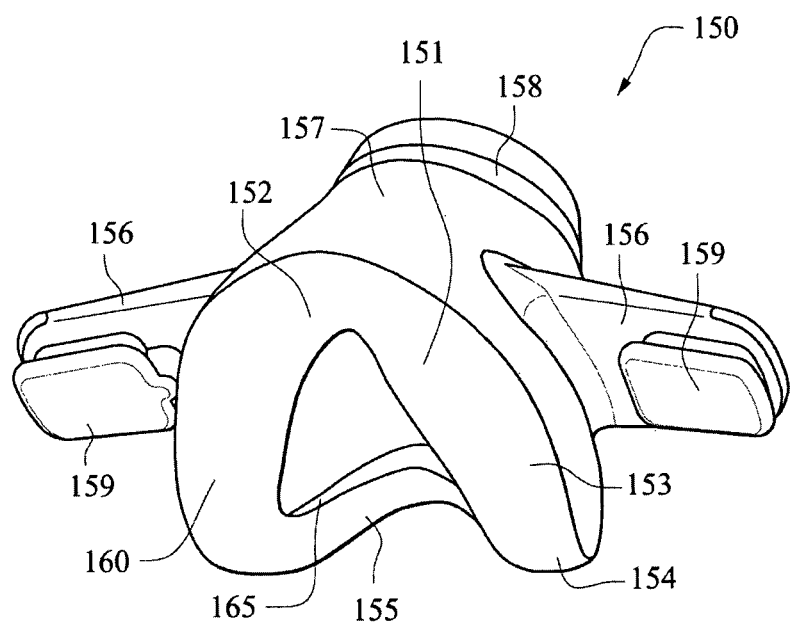
Figures 3, 4, 5, 6:
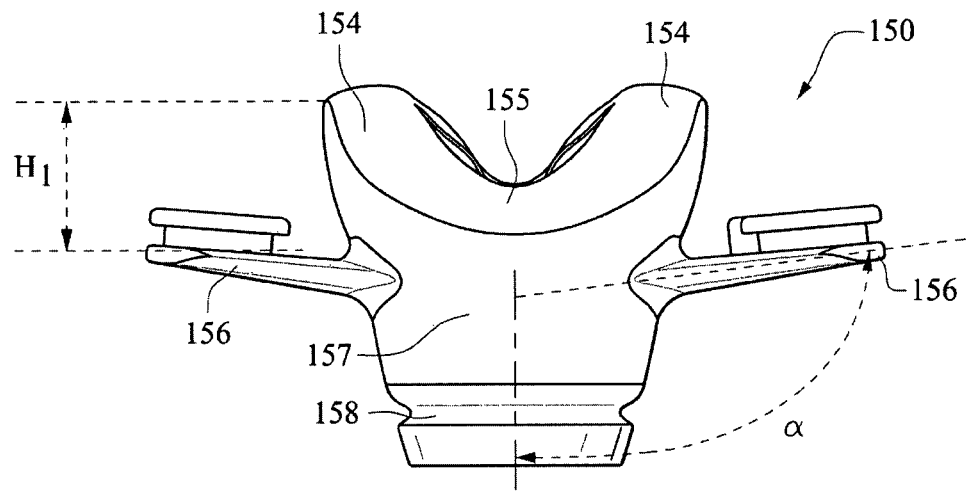
Figures 3, 4, 5, 6, 7:
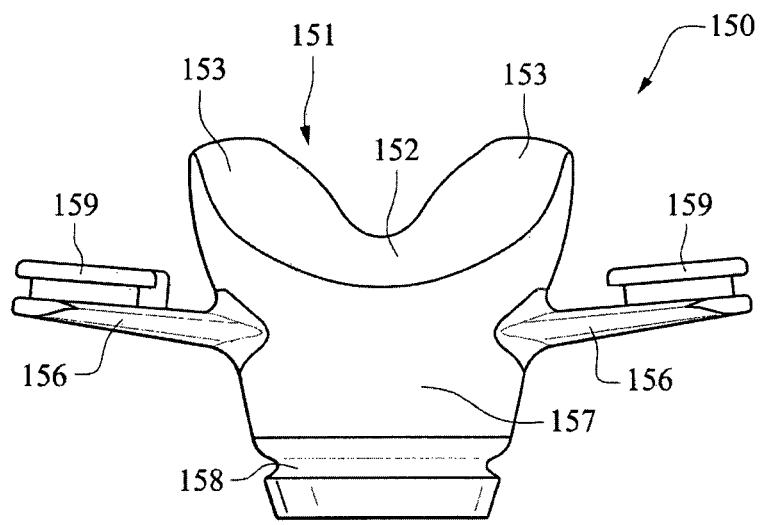
Figures 3, 4, 5, 6, 7, 8:
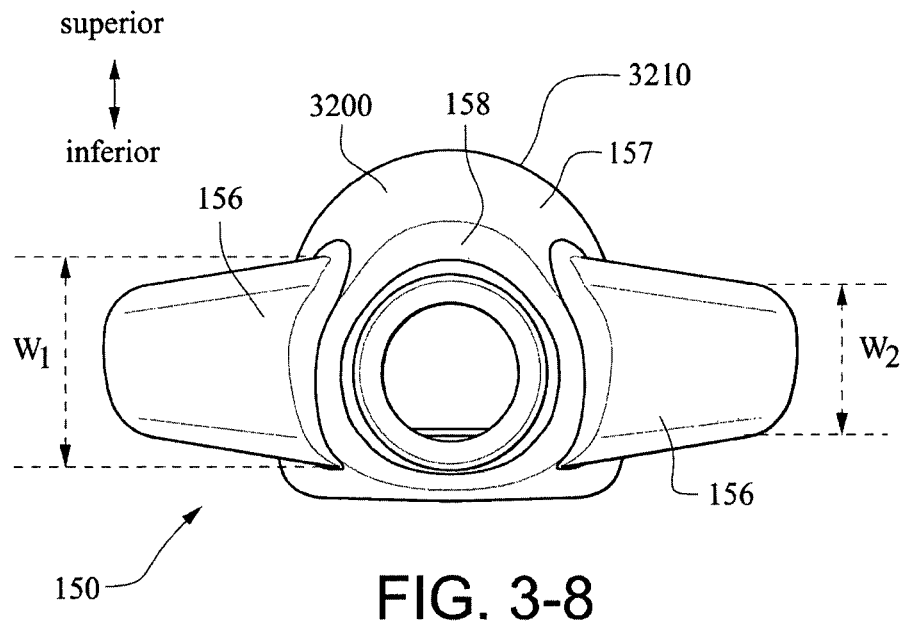
Figures 3, 4, 5, 6, 7, 8, 9:
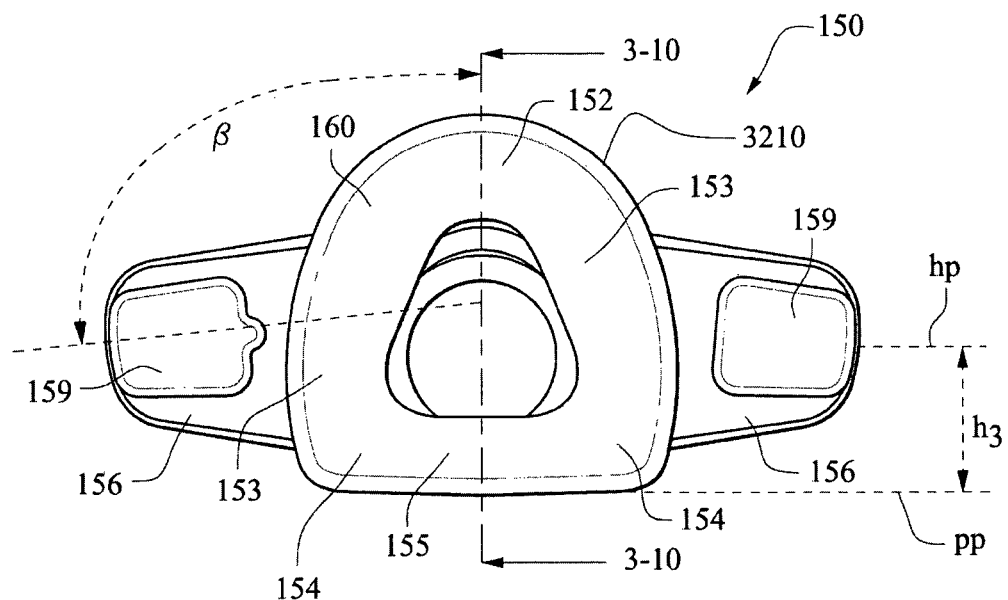
Figures 3, 4, 5, 6, 7, 8, 9, 10:
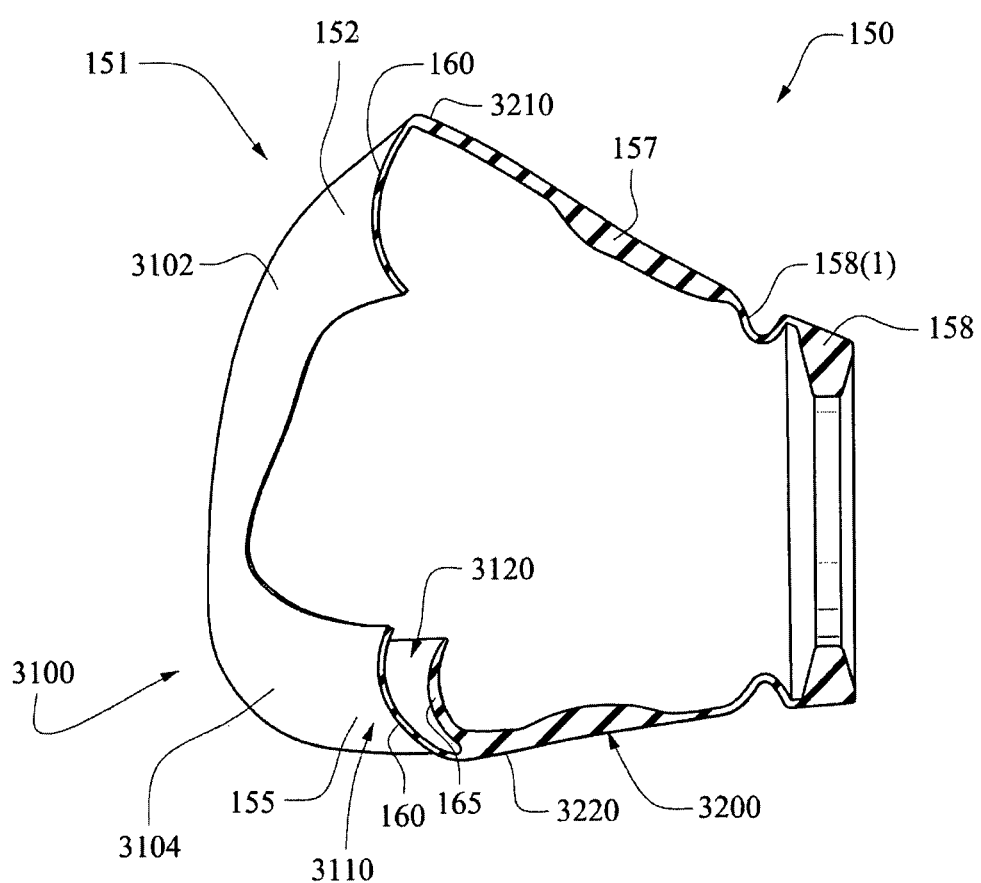
Figures 3, 4, 5, 6, 7, 8, 9, 10, 11:
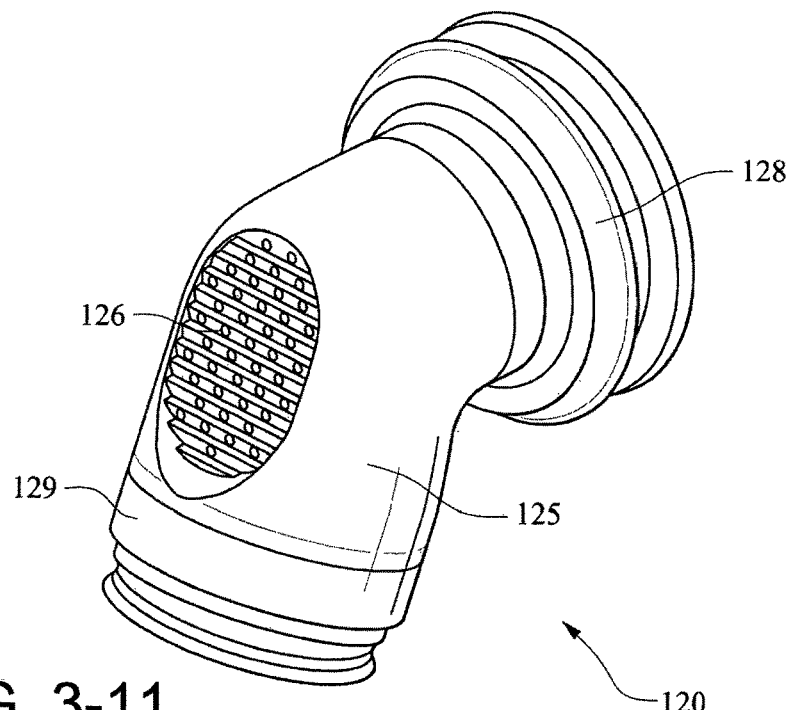
Figures 3, 4, 5, 6, 7, 8, 9, 10, 11, 12:
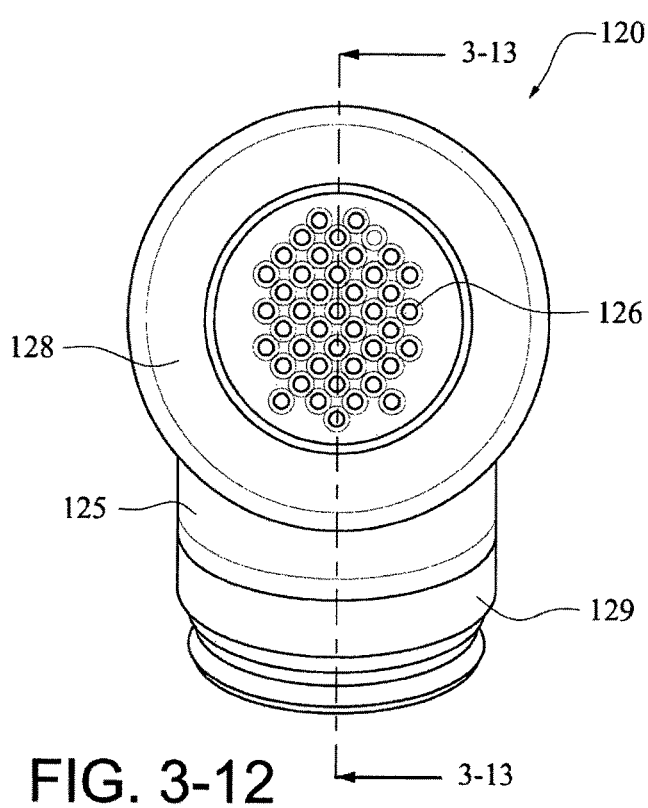
Figures 3, 4, 5, 6, 7, 8, 9, 10, 11, 12, 13:
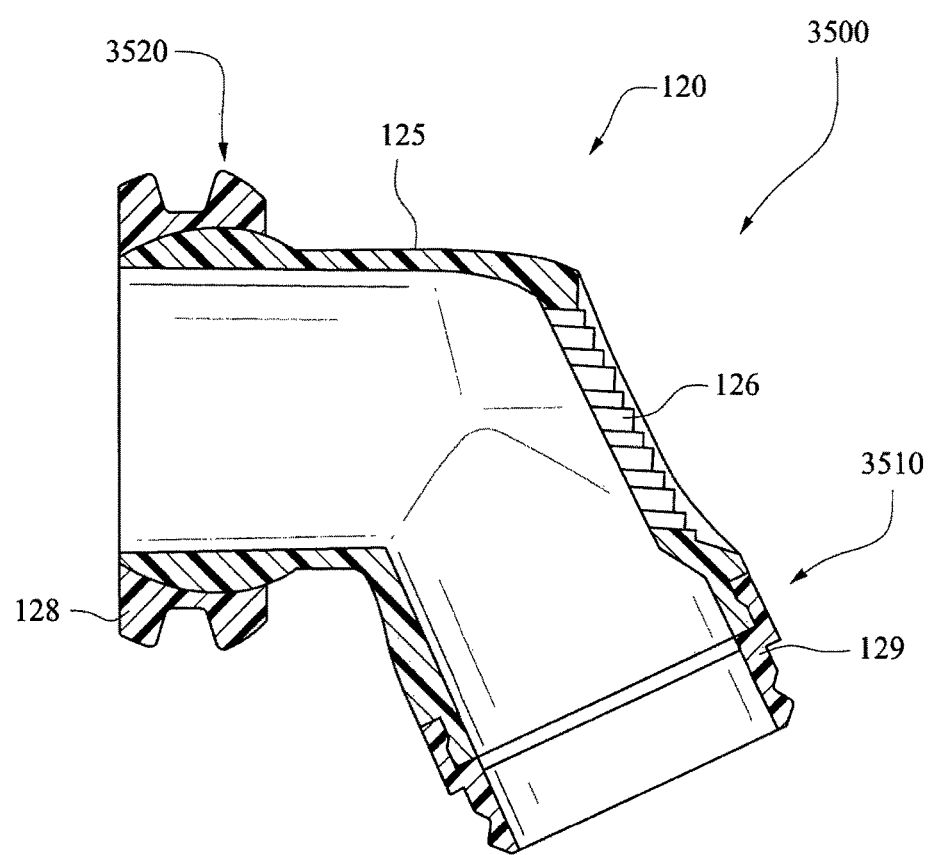
Figures 3, 4, 5, 6, 7, 8, 9, 10, 11, 12, 13, 14:
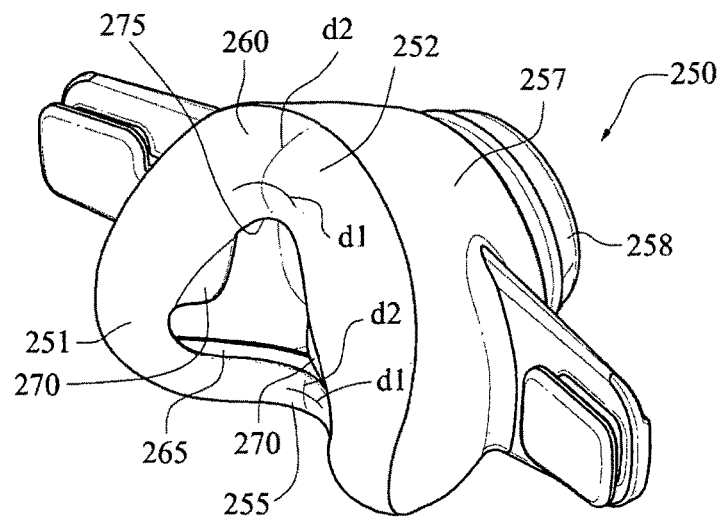
Figures 3, 4, 5, 6, 7, 8, 9, 10, 11, 12, 13, 14, 15:
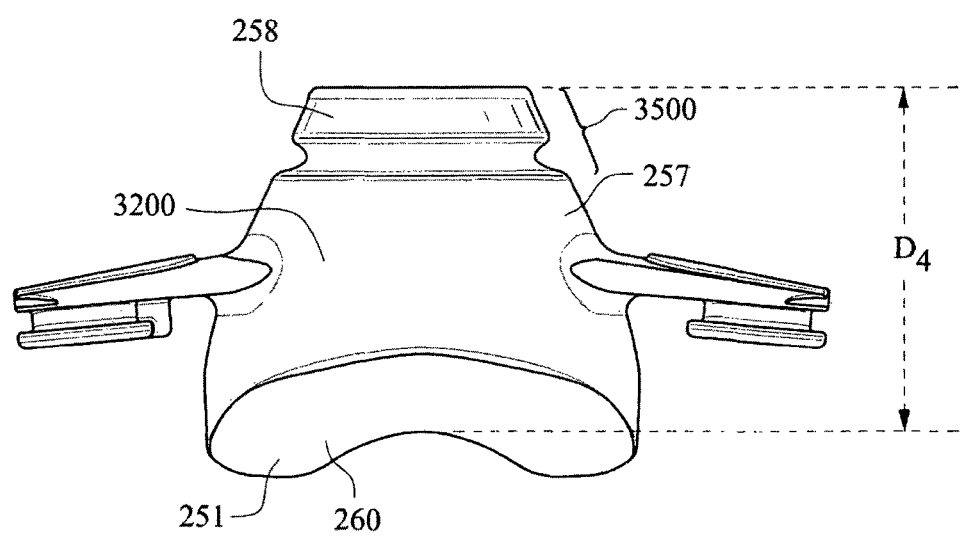
Figures 3, 4, 5, 6, 7, 8, 9, 10, 11, 12, 13, 14, 15, 16:
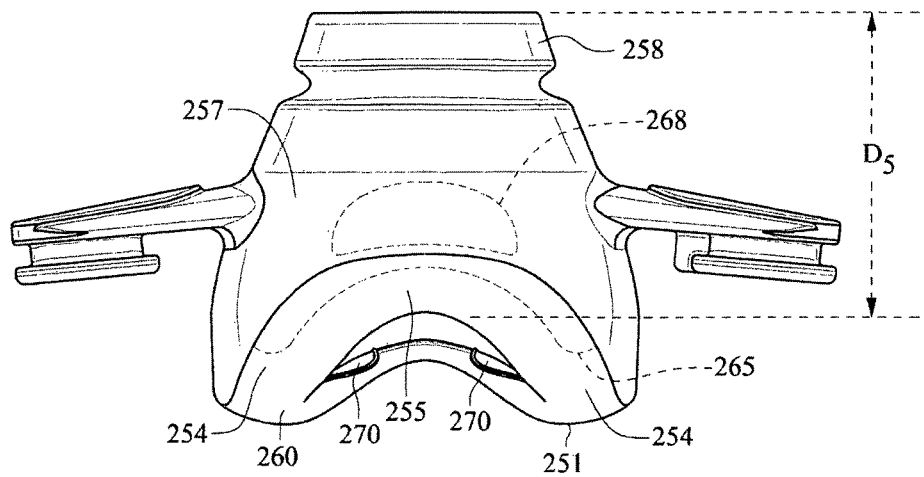
Figures 3, 4, 5, 6, 7, 8, 9, 10, 11, 12, 13, 14, 15, 16, 17:
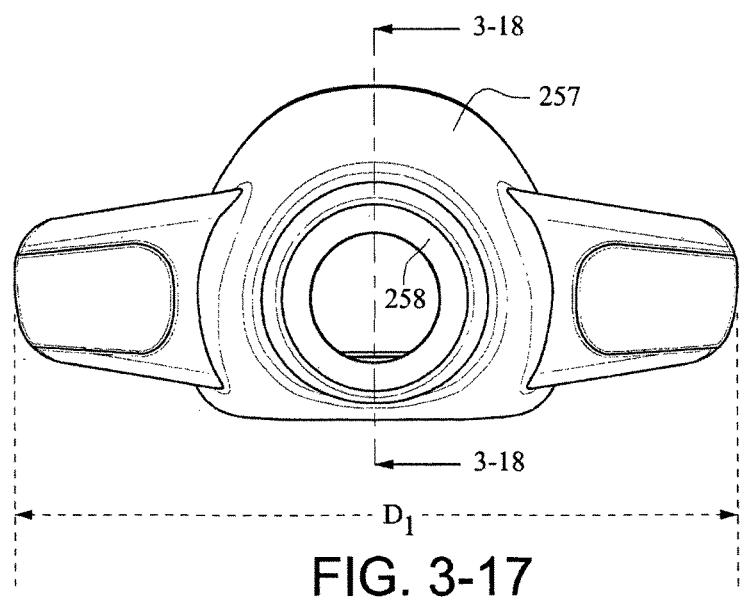
Figures 3, 4, 5, 6, 7, 8, 9, 10, 11, 12, 13, 14, 15, 16, 17, 18:
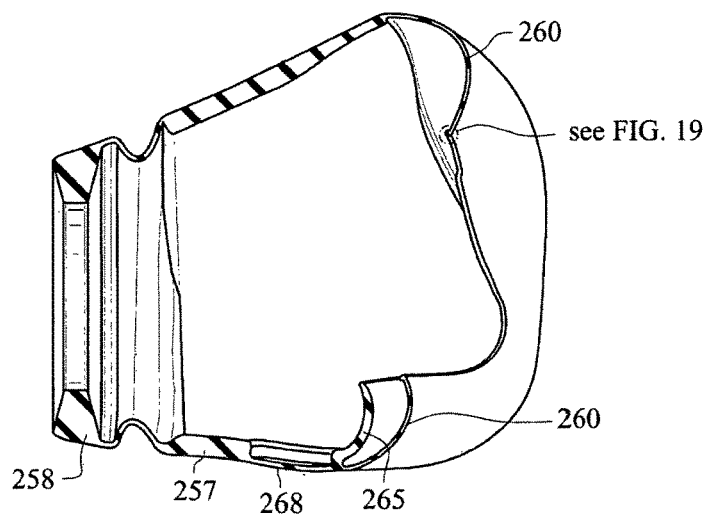
Figures 3, 4, 5, 6, 7, 8, 9, 10, 11, 12, 13, 14, 15, 16, 17, 18, 19:
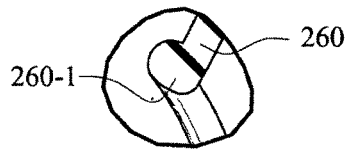
Figures 3, 4, 5, 6, 7, 8, 9, 10, 11, 12, 13, 14, 15, 16, 17, 18, 19, 20:
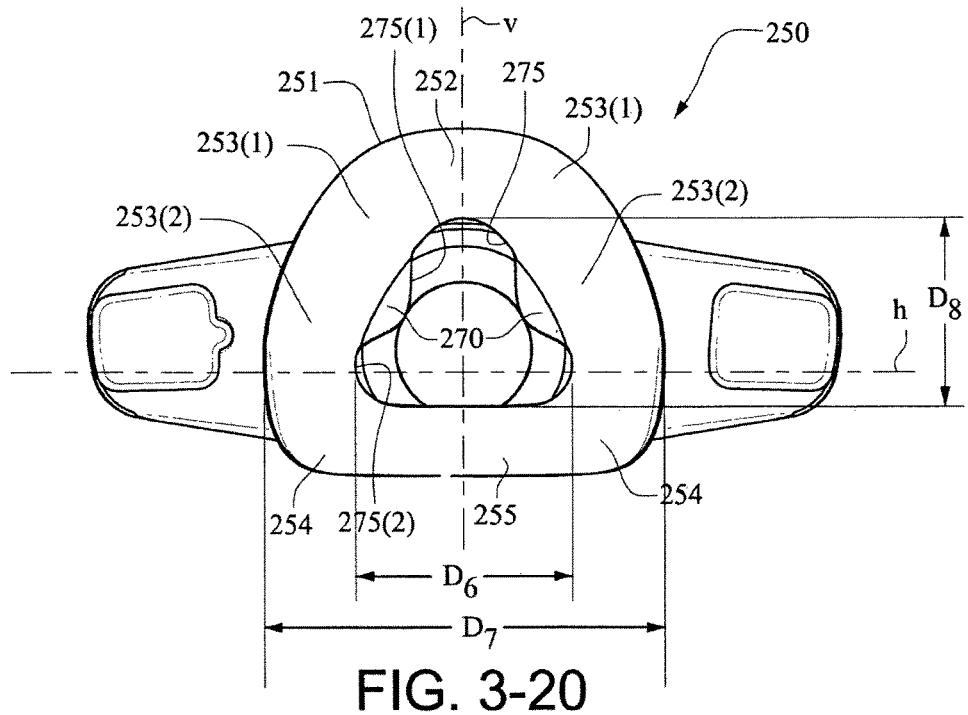
Figures 3, 4, 5, 6, 7, 8, 9, 10, 11, 12, 13, 14, 15, 16, 17, 18, 19, 20, 21:
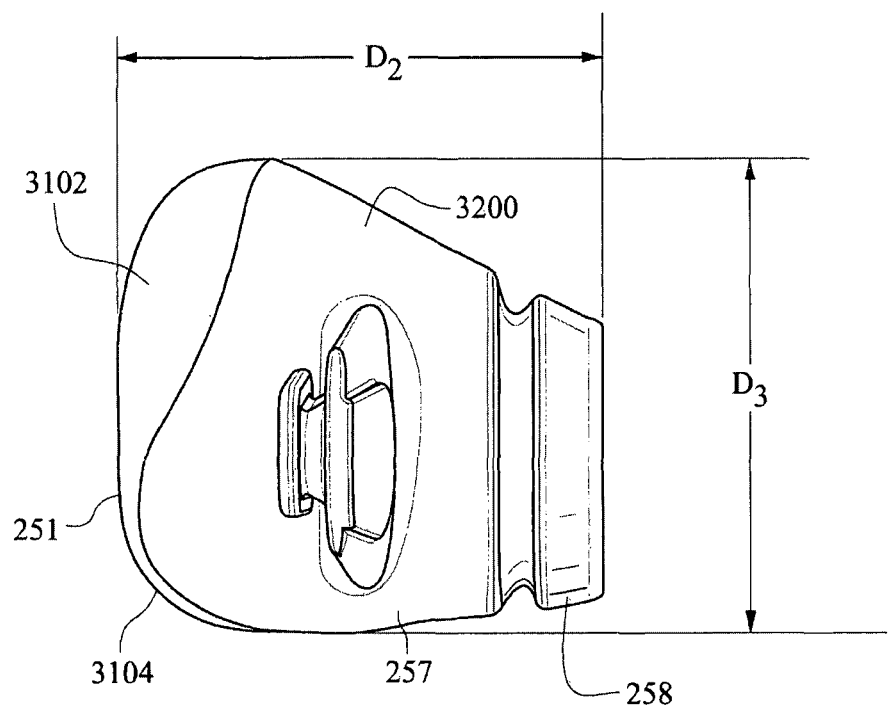
Figures 3, 4, 5, 6, 7, 8, 9, 10, 11, 12, 13, 14, 15, 16, 17, 18, 19, 20, 21, 22:
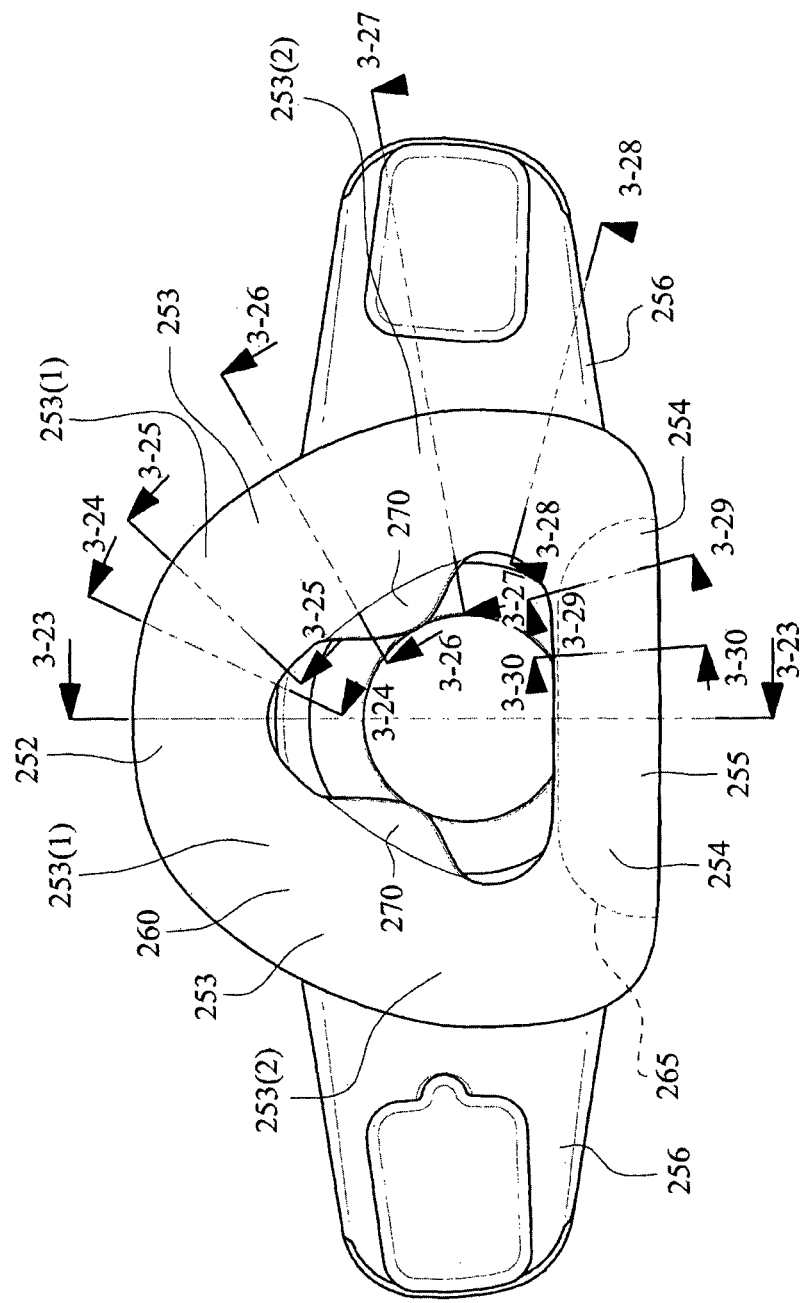
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31:
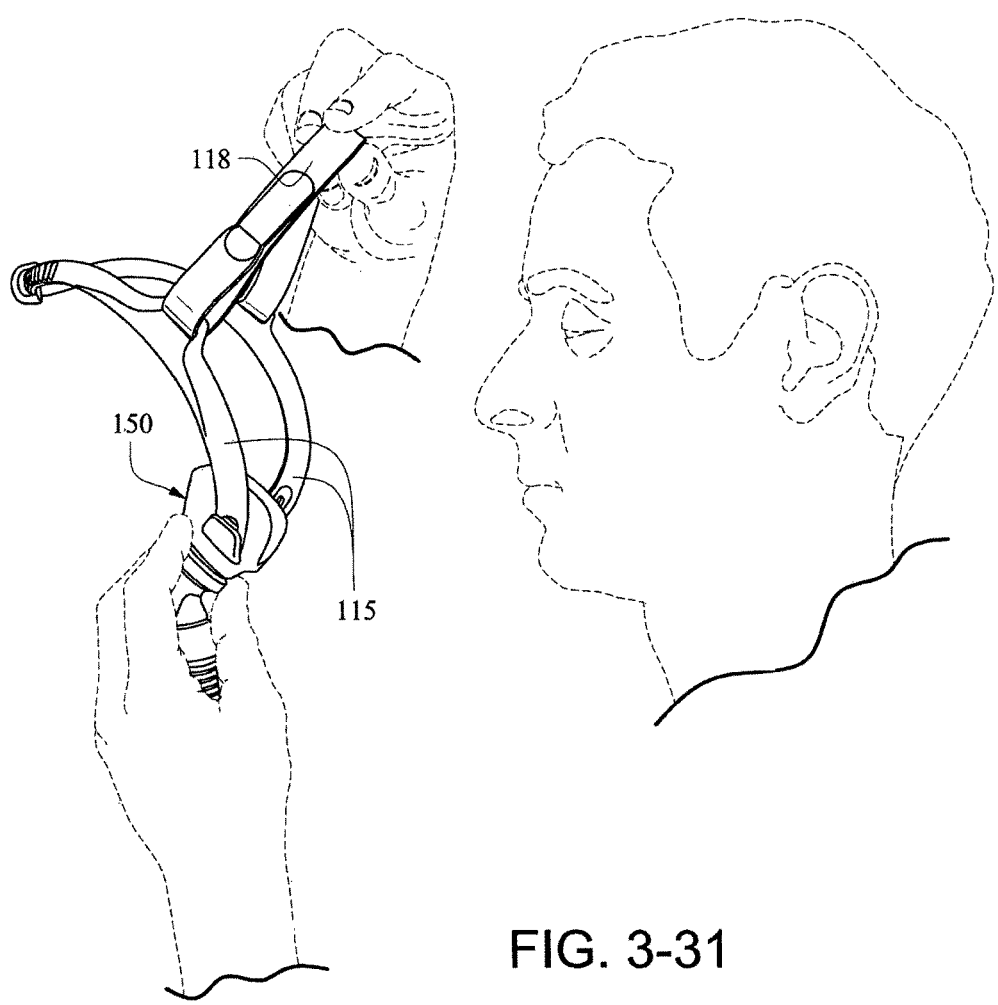
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
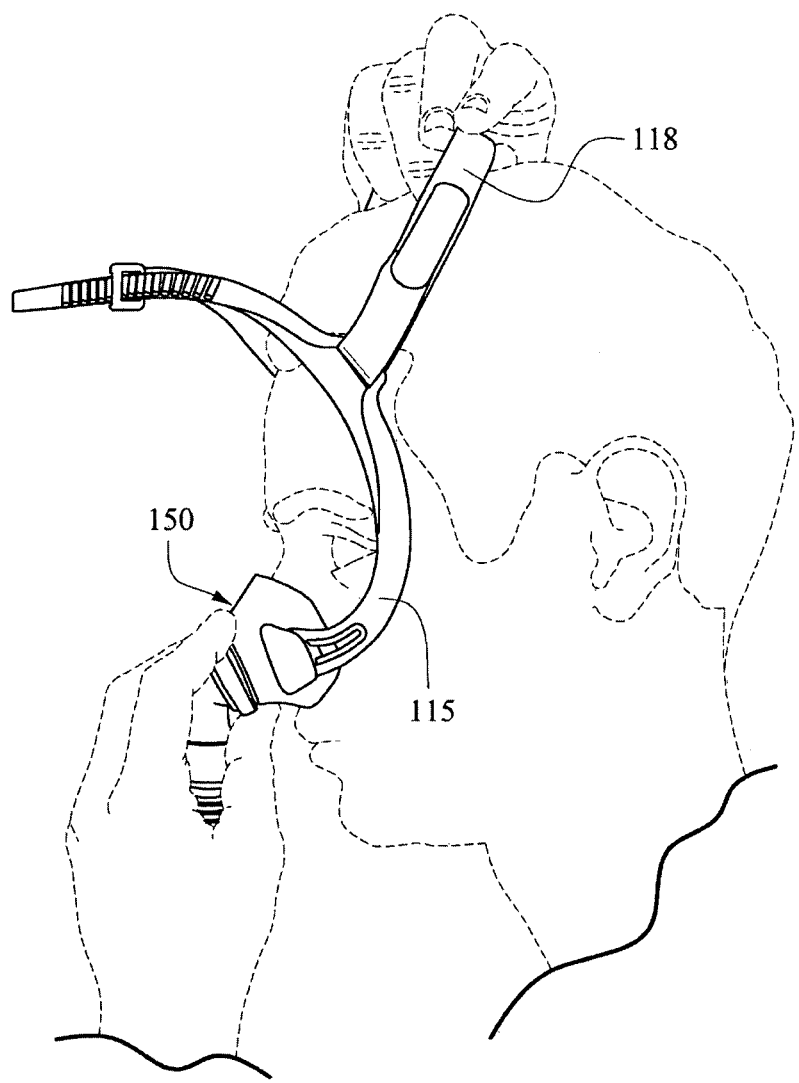
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
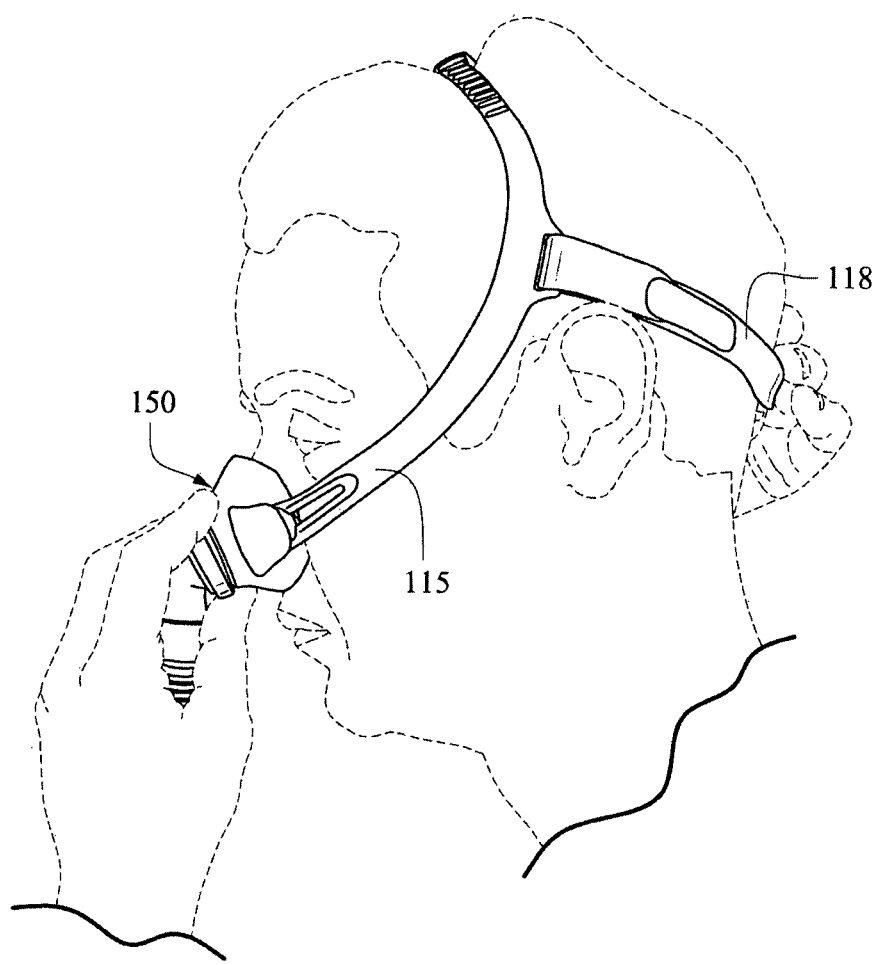
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
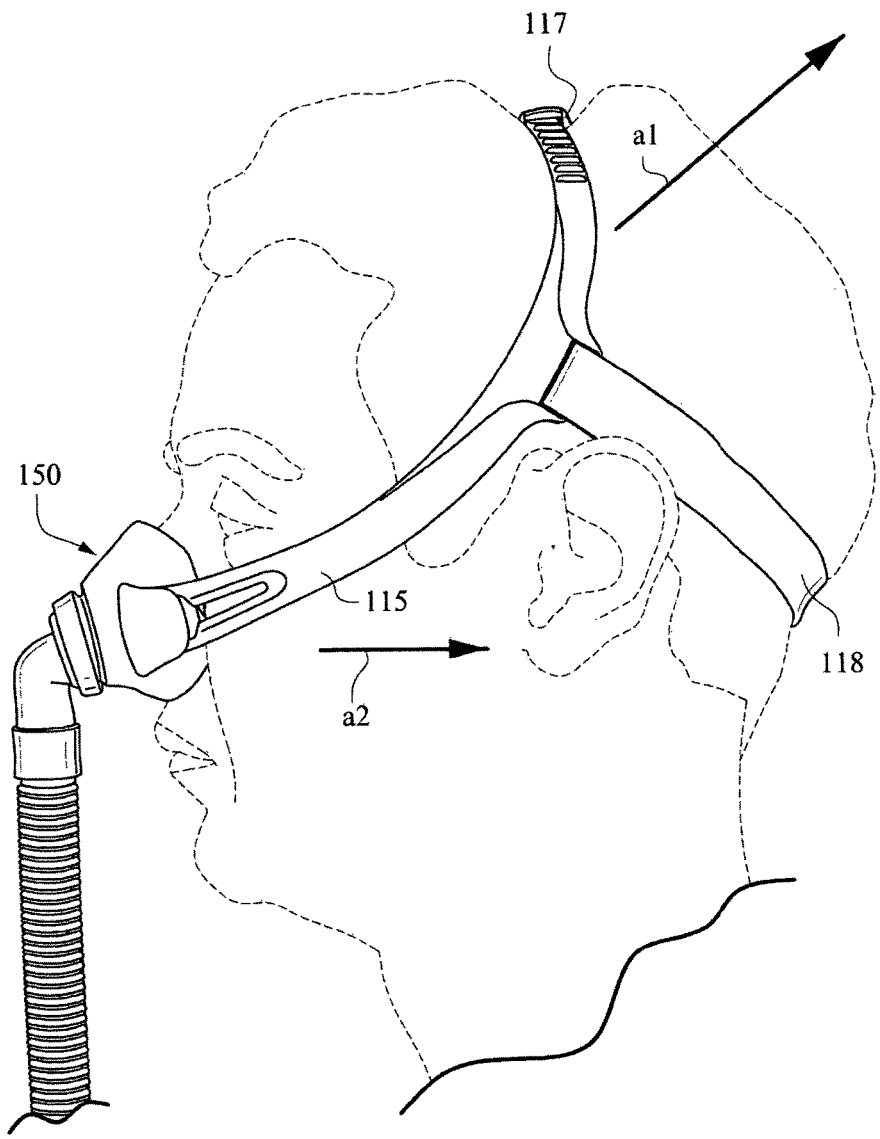
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
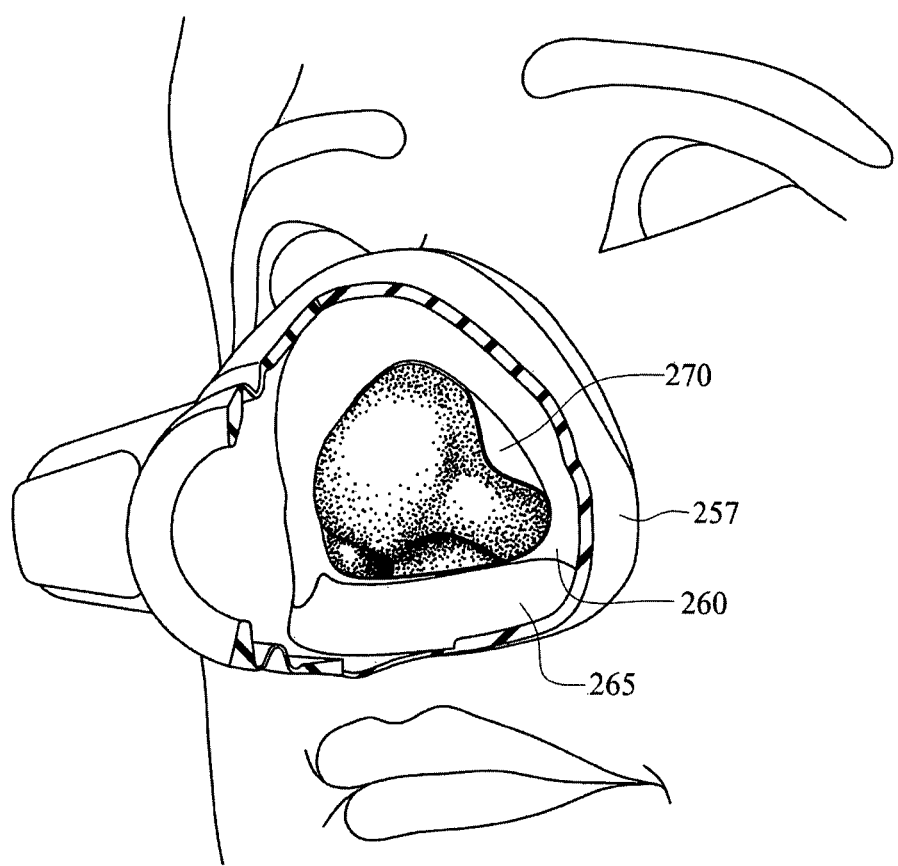
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
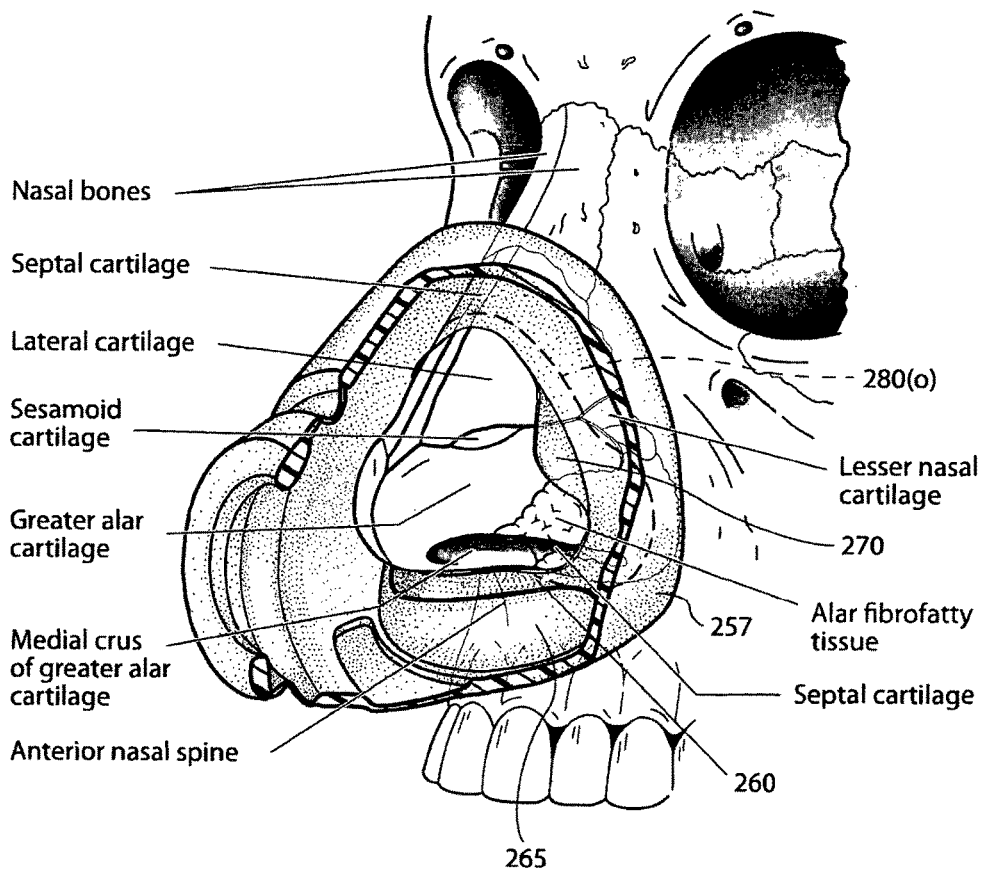
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
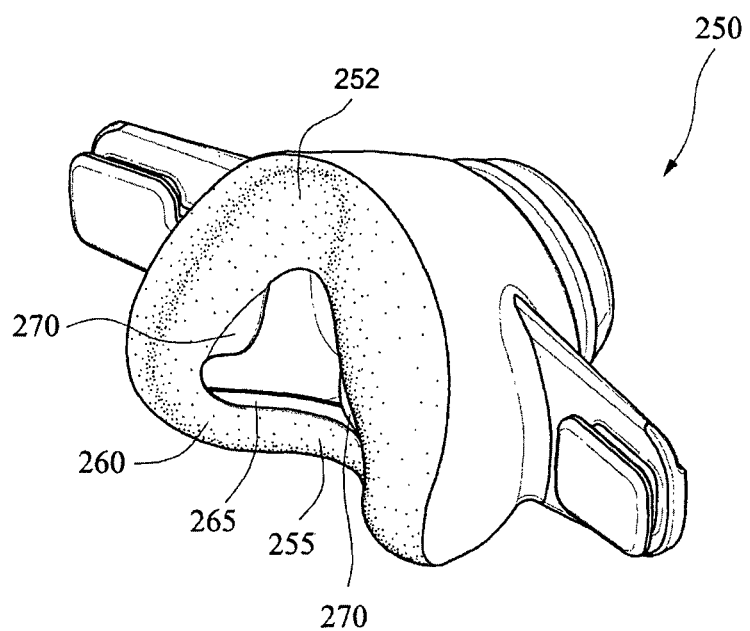
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
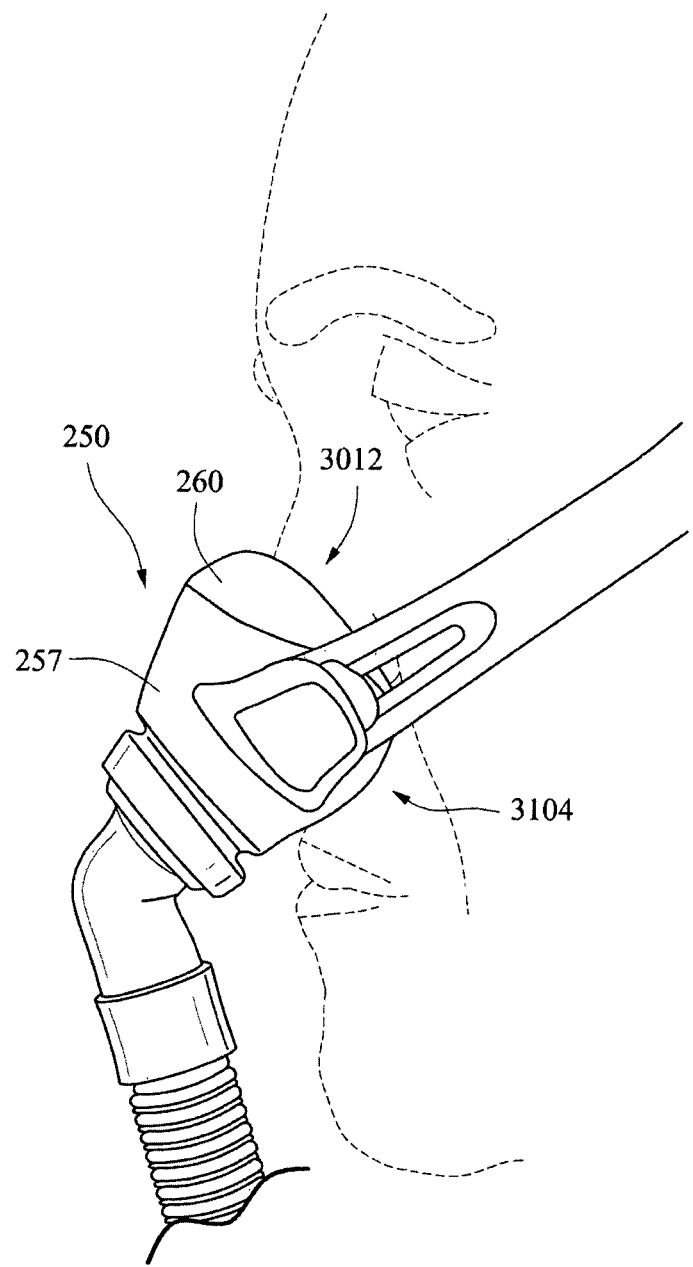
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
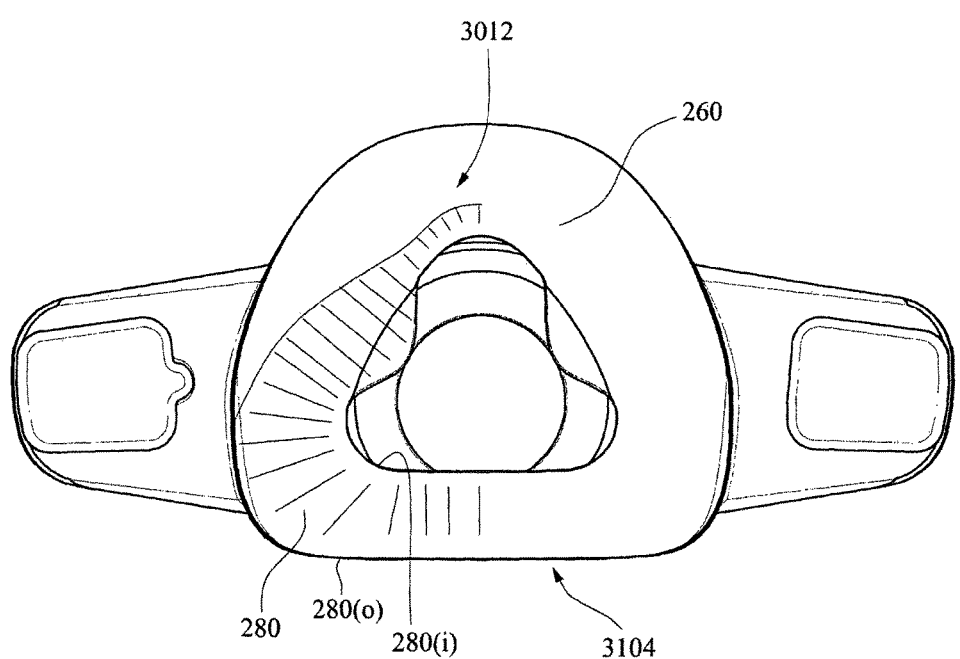
Figures 1, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
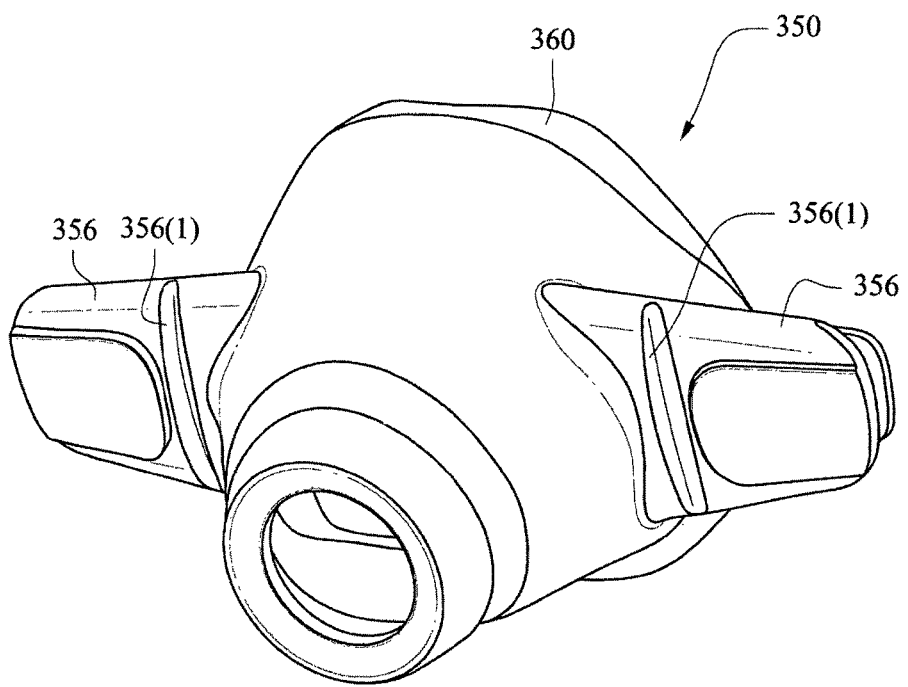
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
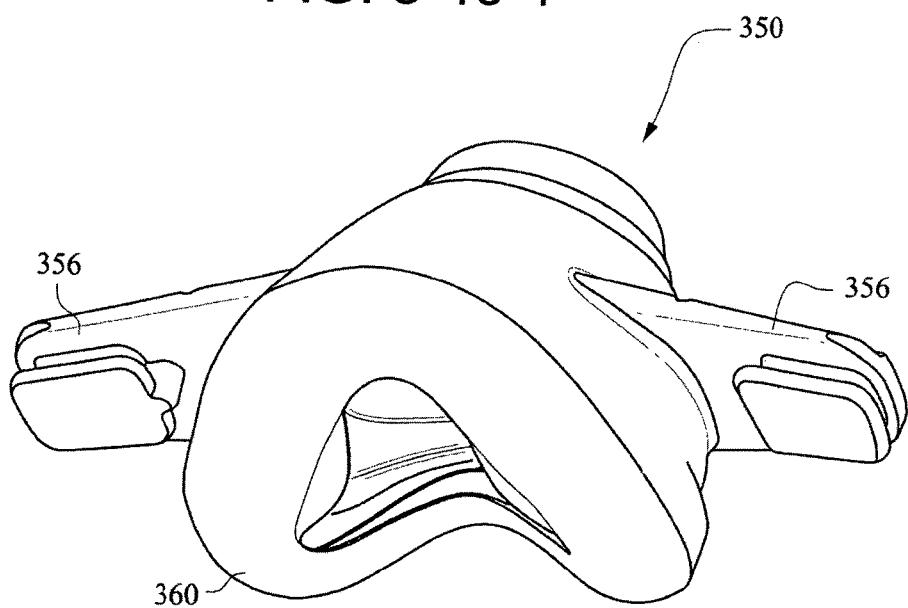
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
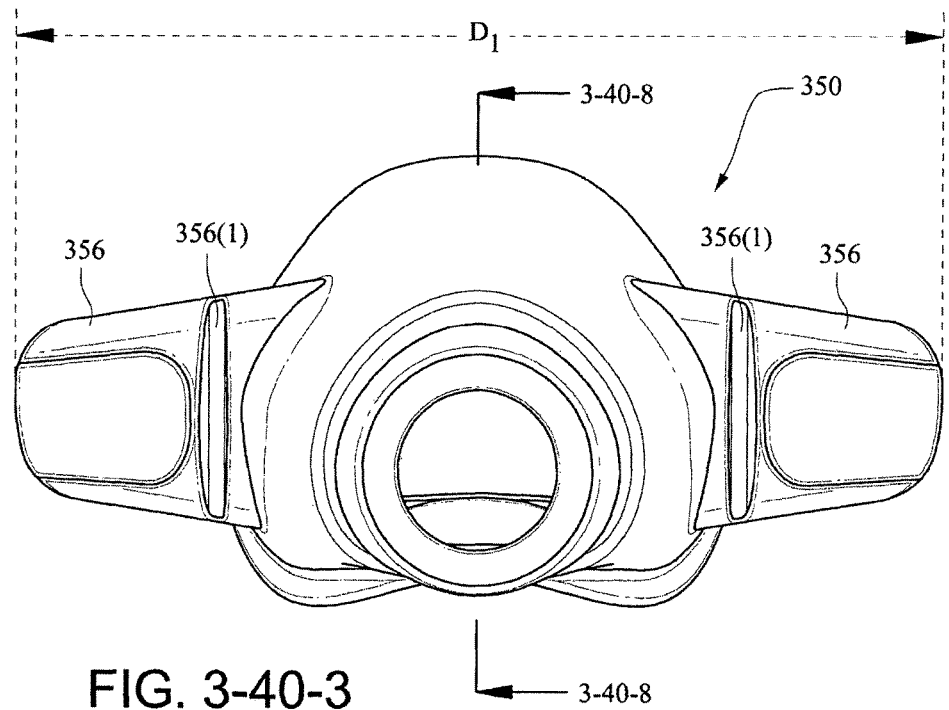
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
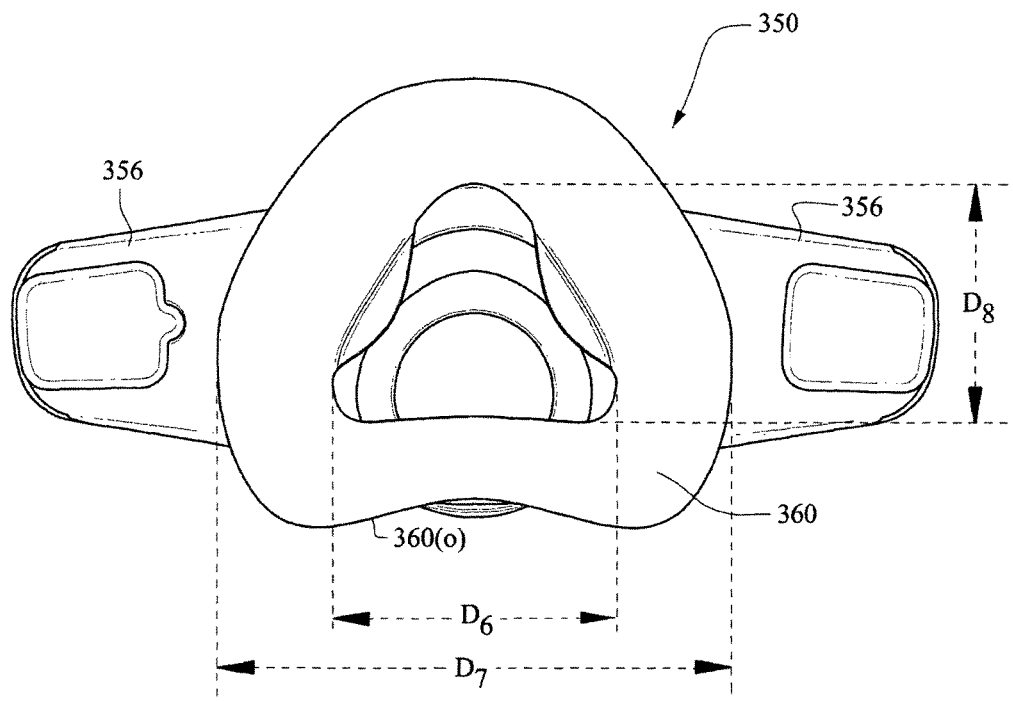
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
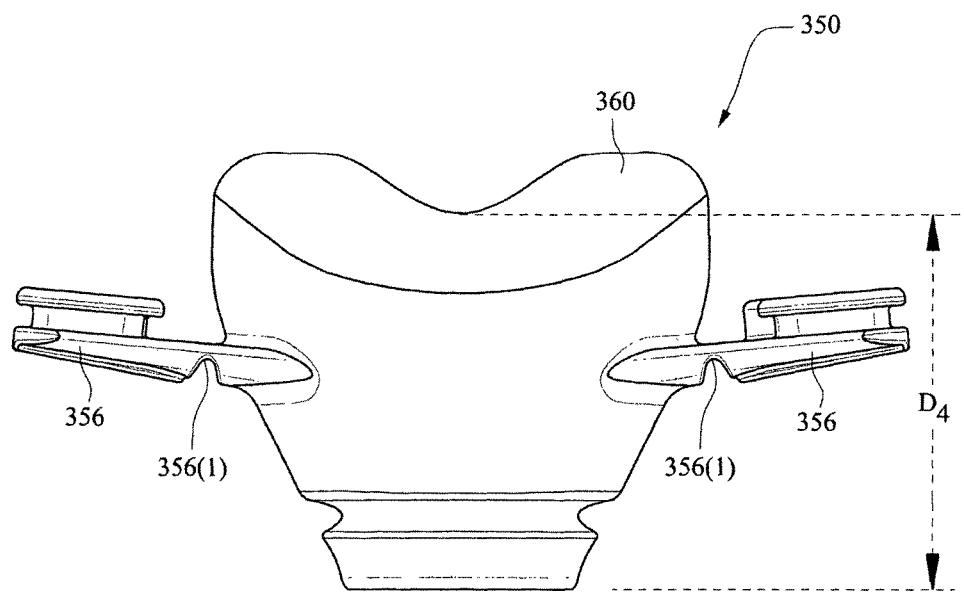
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
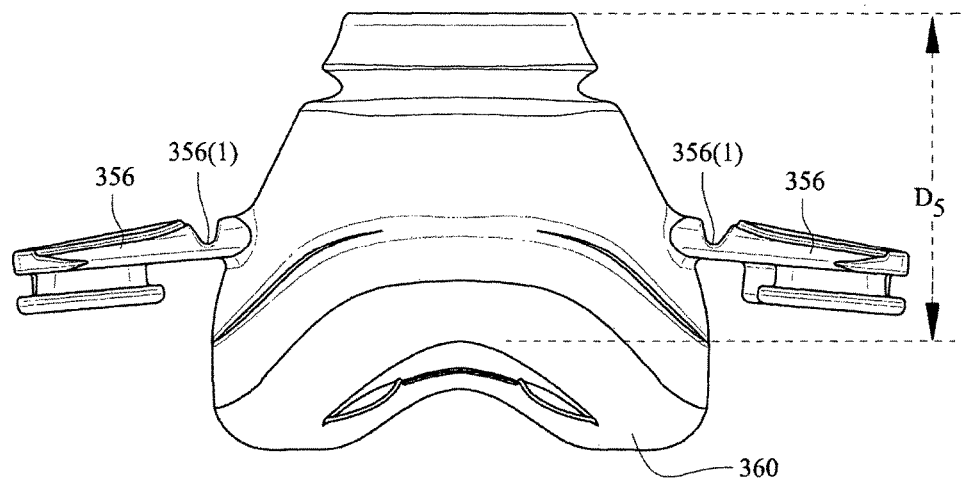
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
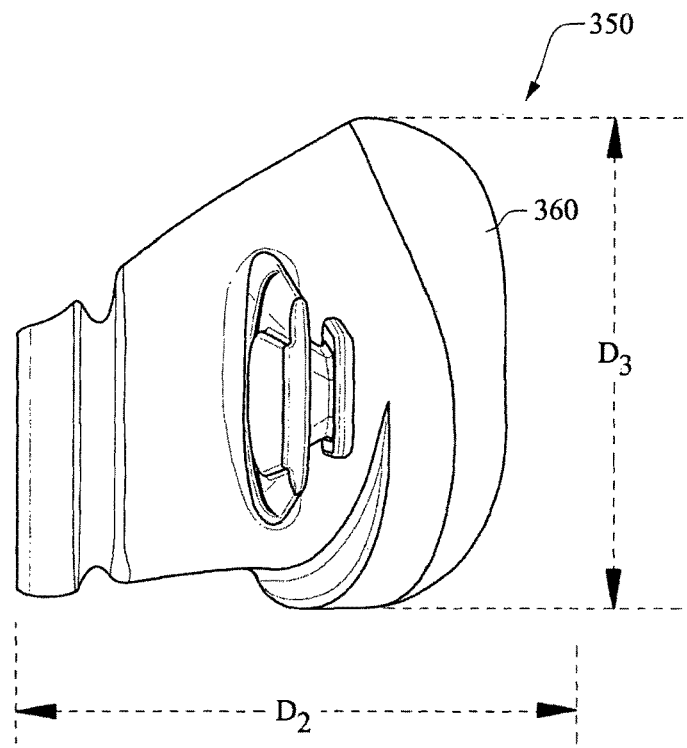
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
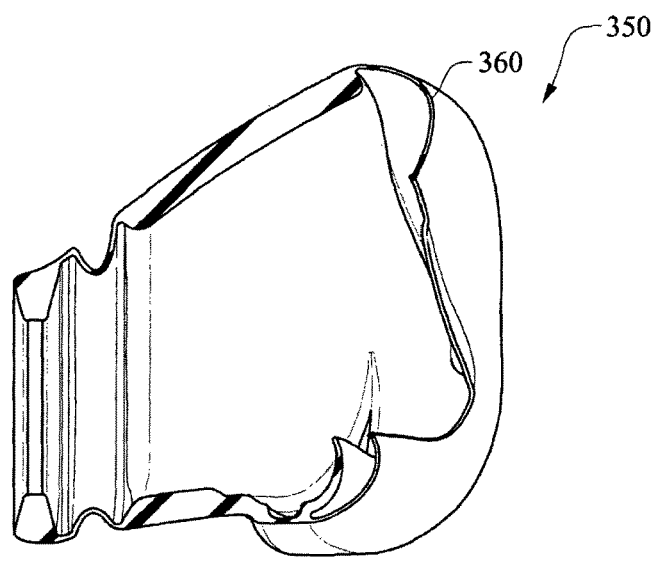
Figures 1, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
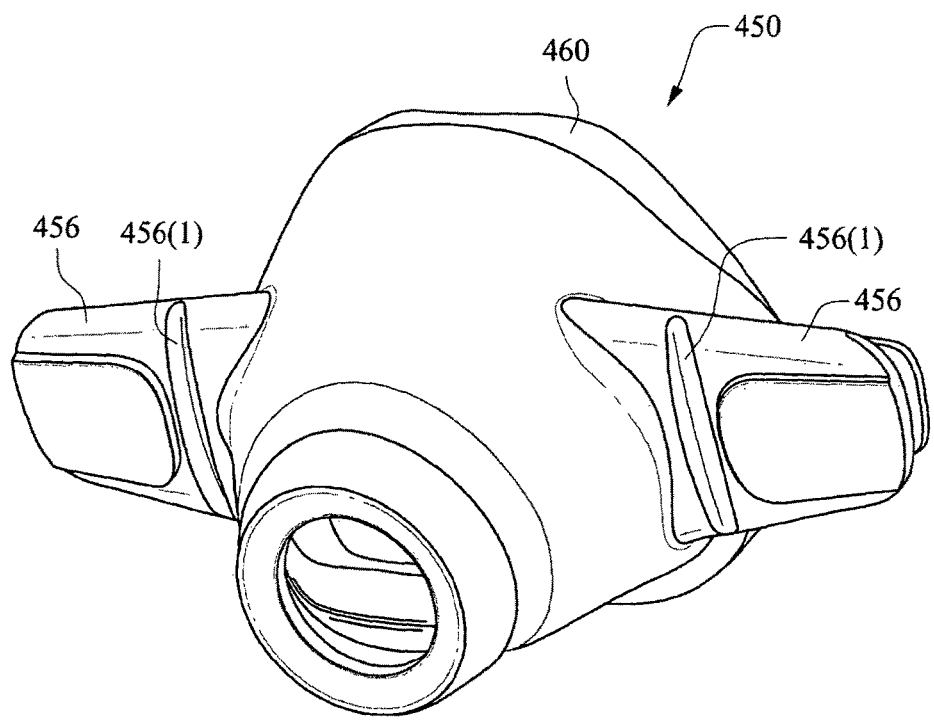
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
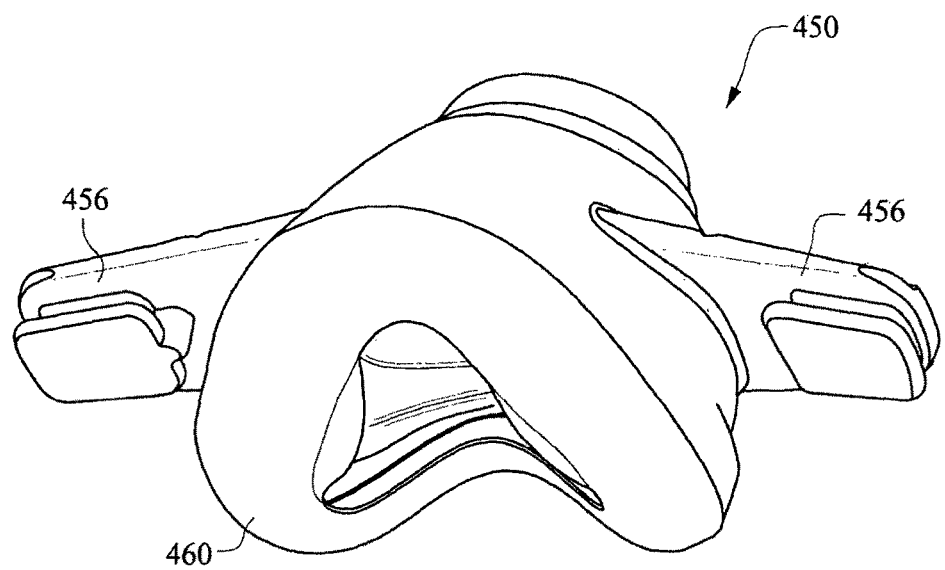
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
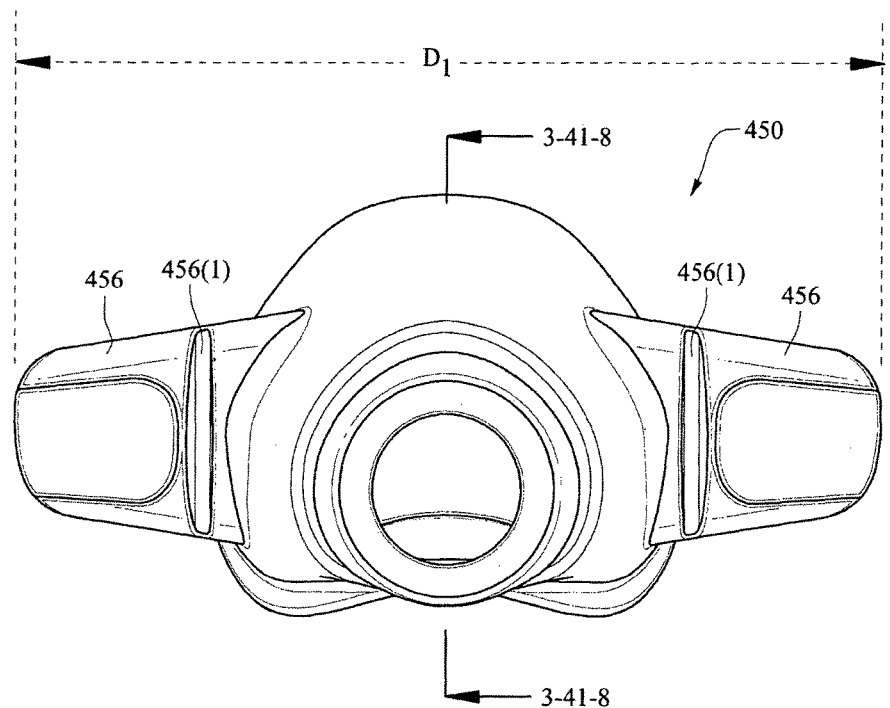
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
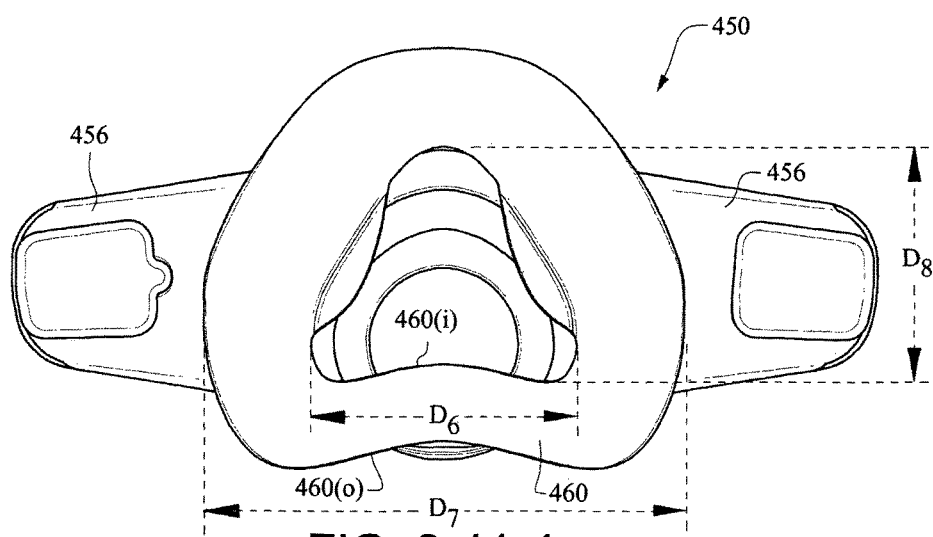
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
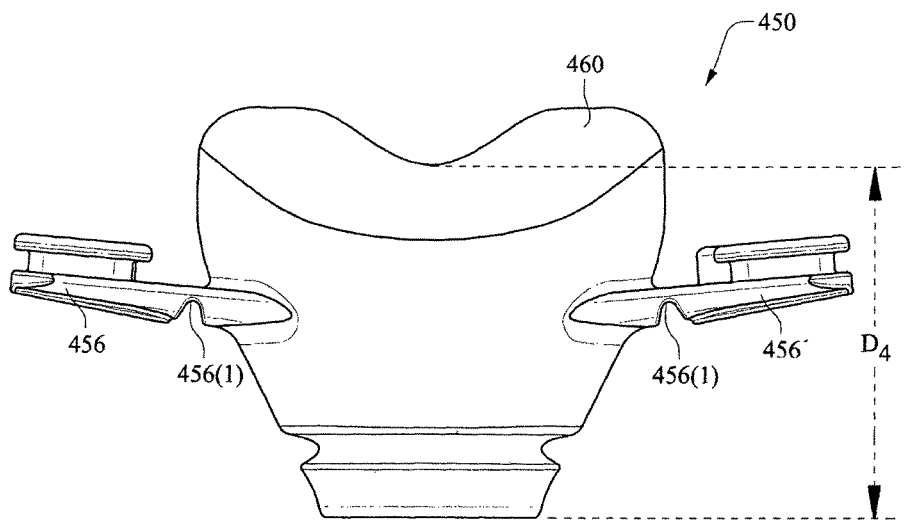
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
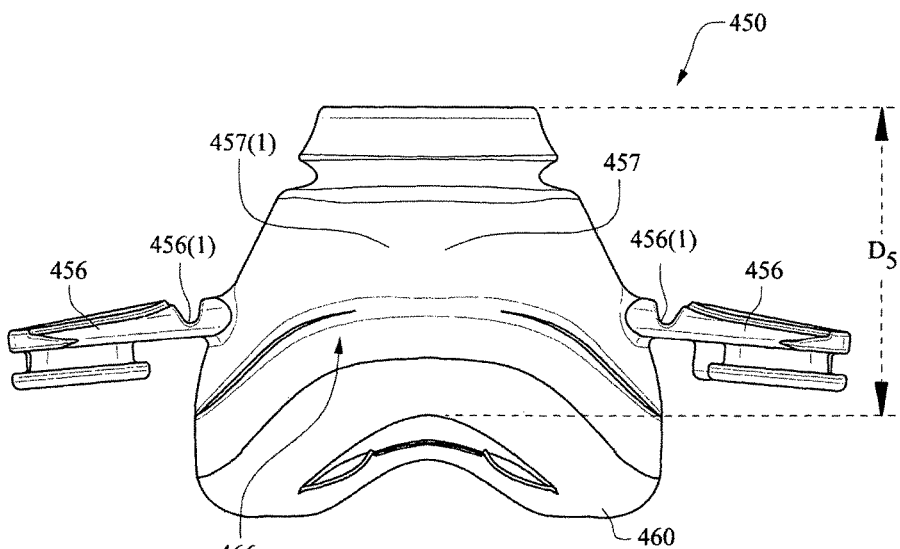
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
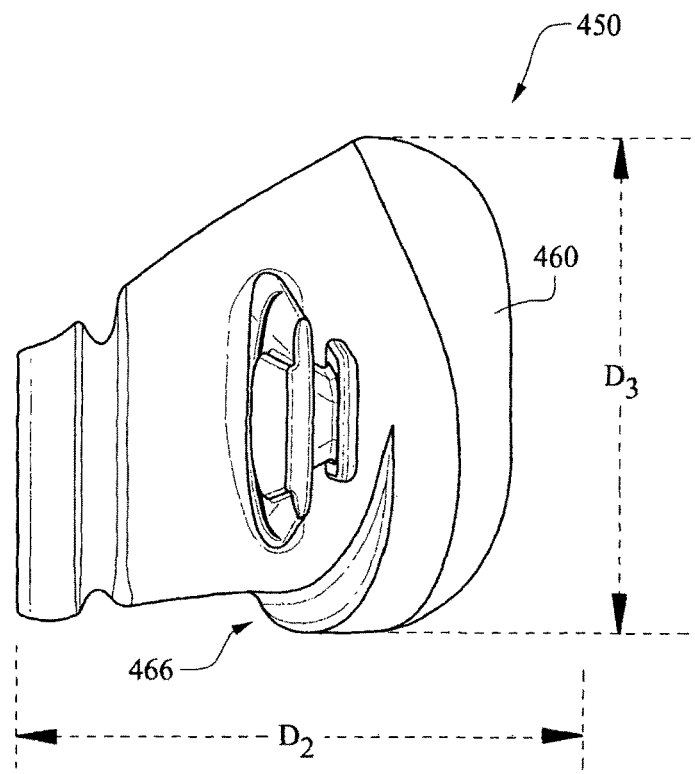
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
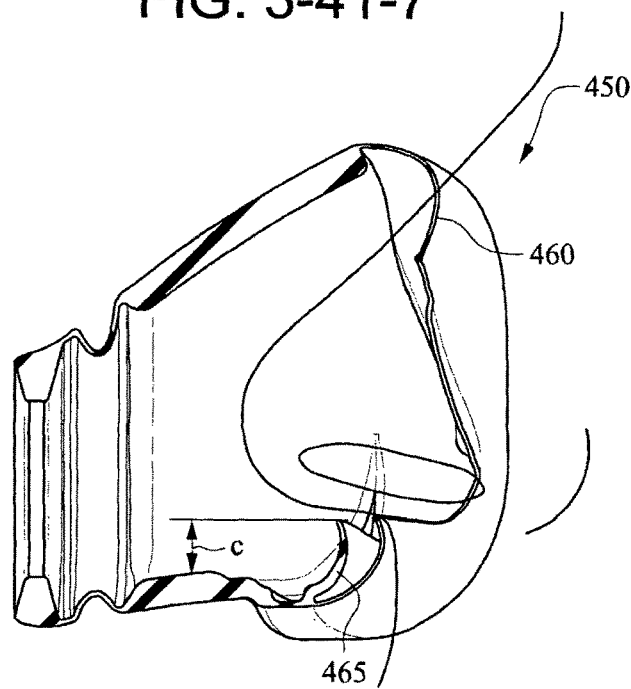
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
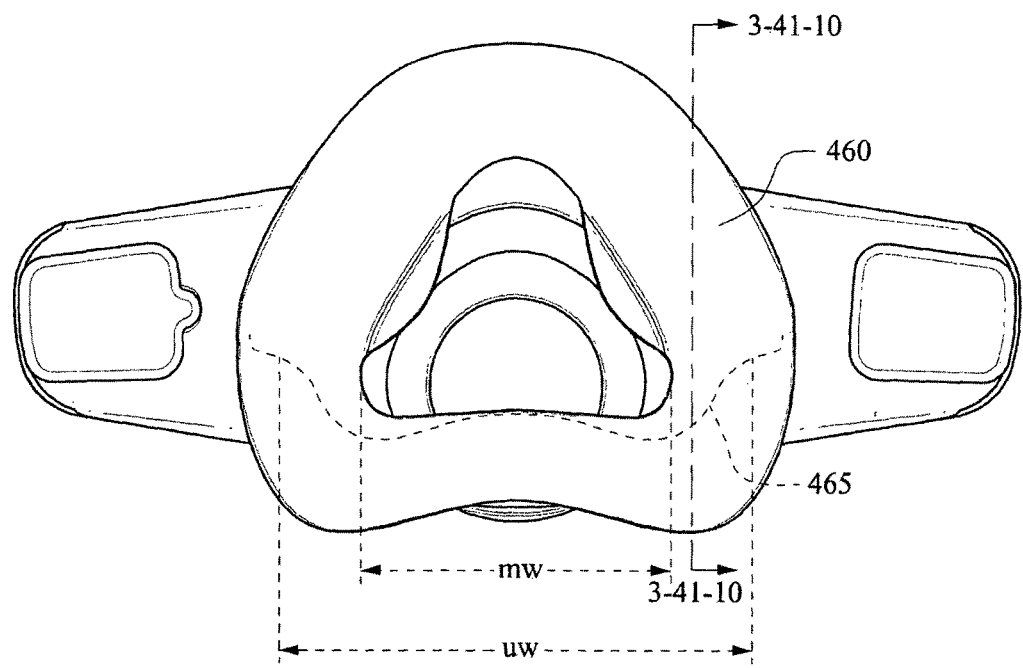
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
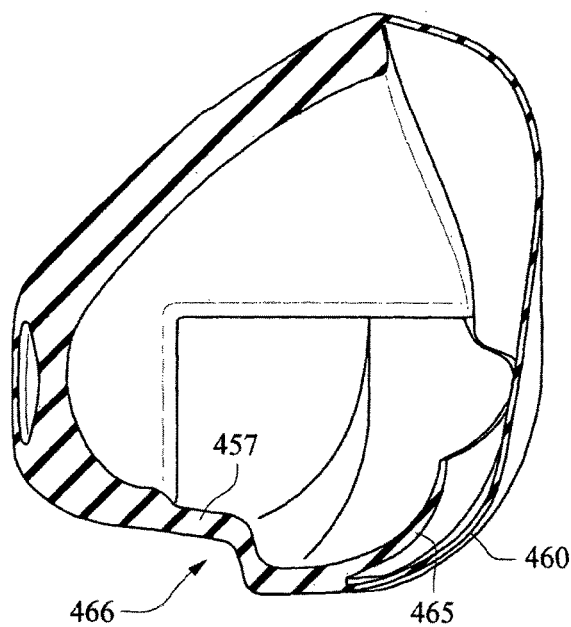

FIG. 3-5 is a perspective rear view of a cushion of a nasal mask system according to an example of the present technology.

FIG. 3-6 is a bottom view of a cushion of a nasal mask system according to an example of the present technology.

FIG. 3-7 is a top view of a cushion of a nasal mask system according to an example of the present technology.

FIG. 3-8 is a front view of a cushion of a nasal mask system according to an example of the present technology.

FIG. 3-9 is a rear view of a cushion of a nasal mask system according to an example of the present technology.

FIG. 3-10 is a cross-sectional view of the cushion of the nasal mask system of FIG. 3-9.

FIG. 3-11 is a perspective view of an elbow assembly of a nasal mask system according to an example of the present technology.

FIG. 3-12 is a rear view of an elbow assembly of a nasal mask system according to an example of the present technology.

FIG. 3-13 is a cross-sectional view of the elbow assembly of a nasal mask system of FIG. 3-12.

FIG. 3-14 is a perspective rear view of a cushion of a nasal mask system according to another example of the present technology.

FIG. 3-15 is a top view of the cushion of FIG. 3-14.

FIG. 3-16 is a bottom view of the cushion of FIG. 3-14.

FIG. 3-17 is a front view of the cushion of FIG. 3-14.

FIG. 3-18 is a cross-section view of the cushion of FIG. 3-17.

FIG. 3-19 is an enlarged view of a portion of FIG. 3-18.

FIG. 3-20 is a rear view of the cushion of FIG. 3-14.

FIG. 3-21 is a side view of the cushion of FIG. 3-14.

FIG. 3-22 is a rear view of the cushion of FIG. 3-14 showing cross-sectional lines.

FIG. 3-23 is a cross-section through line 3-23-3-23 of FIG. 3-22.

FIG. 3-24 is a cross-section through line 3-24-3-24 of FIG. 3-22.

FIG. 3-25 is a cross-section through line 3-25-3-25 of FIG. 3-22.

FIG. 3-26 is a cross-section through line 3-26-3-26 of FIG. 3-22.

FIG. 3-27 is a cross-section through line 3-27-3-27 of FIG. 3-22.

FIG. 3-28 is a cross-section through line 3-28-3-28 of FIG. 3-22.

FIG. 3-29 is a cross-section through line 3-29-3-29 of FIG. 3-22.

FIG. 3-30 is a cross-section through line 3-30-3-30 of FIG. 3-22.

FIGS. 3-31 to 3-34 are sequential views showing exemplary steps for donning a nasal mask system according to an example of the present technology.

FIG. 3-35 is a cross-sectional view showing a nasal mask system engaged with a patient's face according to an example of the present technology.

FIG. 3-36 is a cross-sectional view showing a nasal mask system engaged with a patient's face according to an example of the present technology.

FIG. 3-37 is another perspective view of the cushion of FIG. 3-14.

FIGS. 3-38 shows a cushion assembly engaged with the patient's face and under pressure or inflated in use according to an example of the present technology.

FIG. 3-39 is a schematic rear view of a cushion assembly showing the sealing portions engaged with the patient's face in use according to an example of the present technology.

FIGS. 3-40-1 to 3-40-8 show various views of a cushion assembly according to another example of the present technology.

FIGS. 3-41-1 to 3-41-10 show various views of a cushion assembly according to another example of the present technology.

Pap Device

Figure 4A:
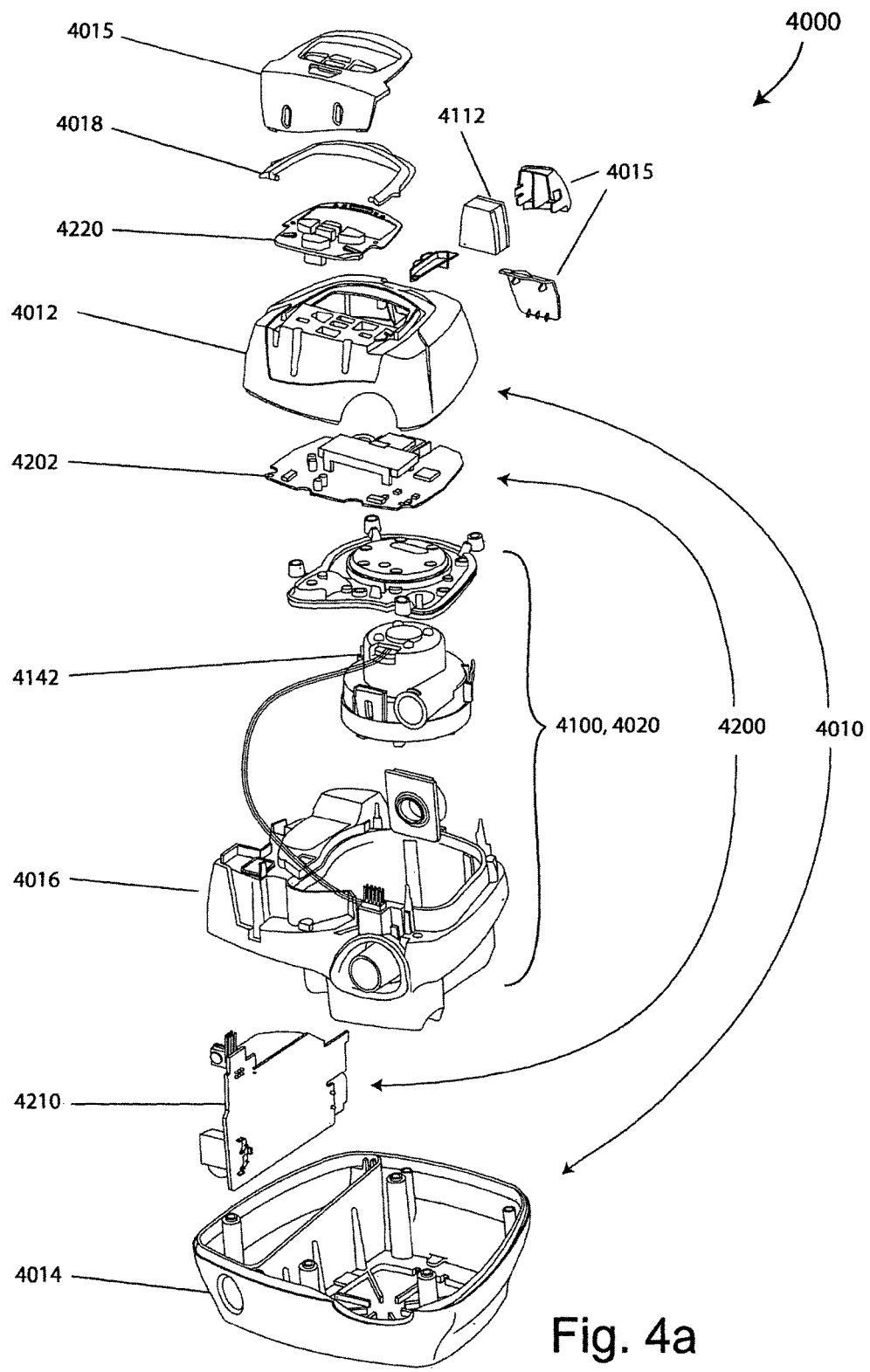

FIG. 4a shows a PAP device in accordance with one form of the present technology.

DETAILED DESCRIPTION ILLUSTRATED EXAMPLES

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to several examples which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. Hence a supply of air may correspond to a supply of gas including air and supplemental oxygen.

Examples of the technology are directed towards a nasal mask system that is easy and quick to fit (e.g., with little or no adjustment), enable reduced strap tension, is manufacturable in high volumes, provides high consumer appeal, provides comfort and seal, provides reliable quality, unobtrusive, and/or fits a large majority of the population.

One or more examples may include exemplary metrics, e.g., dimensions, angles, percentages, etc. Although specific metrics and ranges therefore may be provided, it is to be understood that these metrics and ranges are, merely exemplary and other metrics and ranges are possible depending on application. For example, metrics/ranges that vary from those provided +/−10-20% may be suitable for particular applications.

Treatment Systems

In one form, the present technology comprises apparatus for treating a respiratory disorder. In an example, the apparatus comprises a flow generator or blower for supplying pressurised respiratory gas, such as air, to the patient 1000 via an air delivery tube leading to a patient interface 3000 (e.g., see FIG. 1a). In one form, the apparatus is a CPAP system, in other forms the apparatus is a ventilator.

Therapy

Figure 1A:
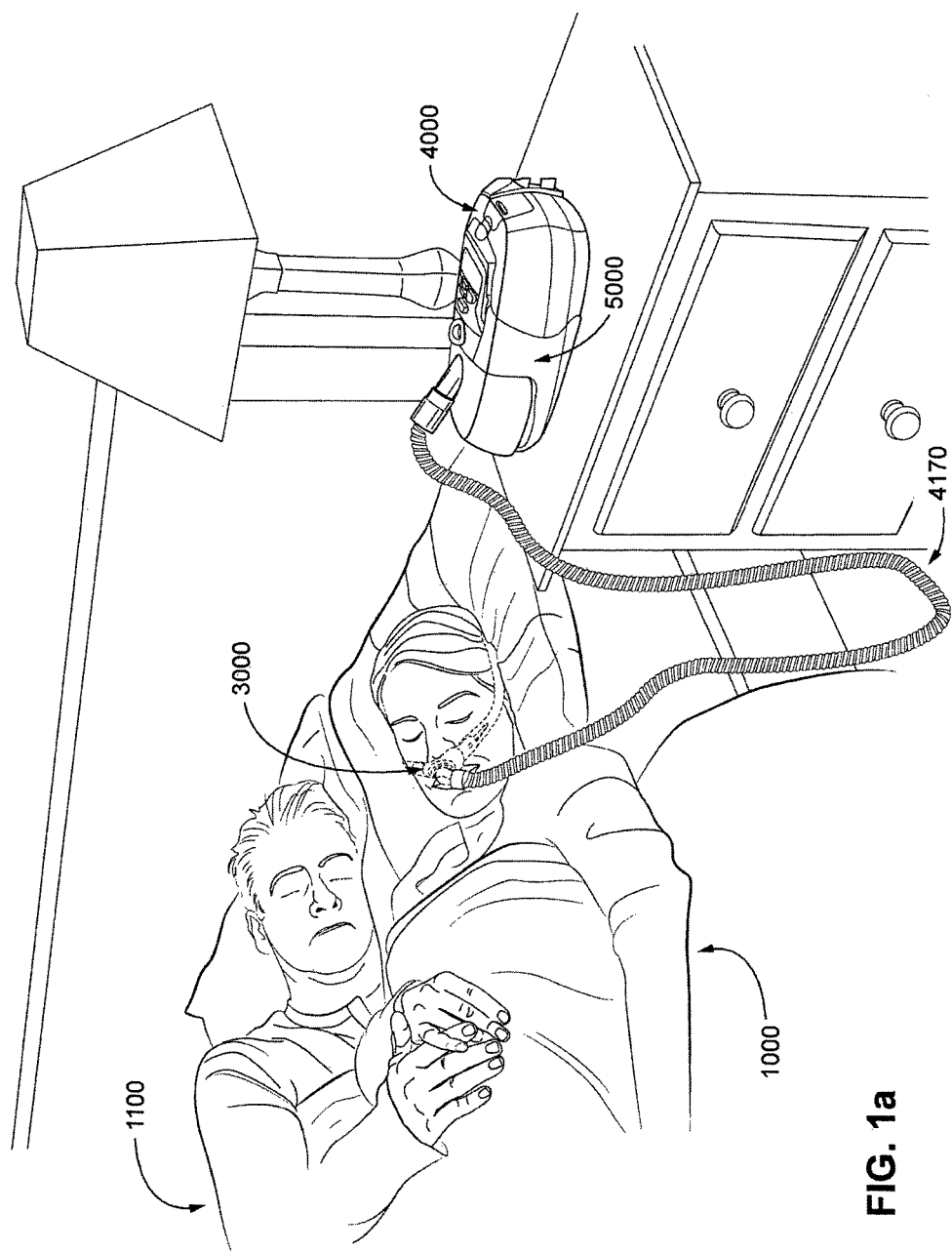
FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000. The PAP device 4000, humidifier 5000 and air circuit 4170 may be connected to a patient interface 3000 in accordance with the present technology.

In one form, the present technology comprises a method for treating a respiratory disorder comprising the step of applying positive pressure to the entrance of the airways of a patient 1000 (e.g., see FIG. 1a).

Nasal CPAP for OSA

In one form, the present technology comprises a method of treating Obstructive Sleep Apnea in a patient by applying nasal continuous positive airway pressure to the patient.

Patient Interface 3000

A patient interface 3000 in accordance with one aspect of the present technology comprises the following functional aspects: a seal-forming structure 3100, a plenum chamber 3200, a positioning and stabilising structure 3300 and a connection port 3600 for connection to an air circuit 4170 (e.g., see FIG. 3-2). In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

In an example, the plenum chamber 3200 and the seal forming structure 3100 are moulded in one piece. In another example they are formed as two or more separate components.

A patient interface 3000 in accordance with one form of the present technology is nasal mask system 100. As shown in FIGS. 3-1 to 3-3, nasal mask system 100 in accordance with the present technology may comprise a headgear assembly 110, an elbow assembly 120, an air delivery assembly 130 and a cushion assembly or cushion 150. FIGS. 3-4 to 3-10 show various views of the cushion assembly 150, and FIGS. 3-11 to 3-12 show various views of the elbow assembly 120.

A plenum chamber 3200 in accordance with one form of the present technology is cushion assembly 150. Cushion assembly 150 may be adapted to sealingly engage with a patient's airway, including a patient's nose. As shown in FIGS. 3-1 to 3-3, cushion assembly 150 may receive breathable gas from air delivery assembly 130 and/or elbow assembly 120, and be supported in position by headgear assembly 110.

Cushion assembly 150 may comprise a sealing region or sealing cuff 151, two headgear connectors 156, a side wall or side wall region 157 and an attachment region 158. In an example, cushion assembly 150 may be formed from a flexible elastomer or rubber.

FIGS. 3-14 to 3-30, 3-35, and 3-36-1 to 3-40-2 show various views of a cushion assembly 250 according to another example of the present technology, which is similar to the cushion assembly 150. As described below, the cushion assembly 250 includes a thinner wall section adjacent a top lip region of the sealing region of the cushion assembly (e.g., to avoid excessive pressure on the patient's columella and septum). Also, each side of the nose region of the sealing region includes a wing or sealing flap adapted to form a seal on the region adjacent the junction between the nasal greater alar cartilage and the lateral nasal cartilage of the patient's nose.

In the illustrated example of FIGS. 3-14 to 3-21, $D_1$ is about 85-105 mm (e.g., about 97 mm), $D_2$ is about 35-55 mm (e.g., about 48 mm), $D_3$ is about 35-55 mm (e.g., about 44 mm), $D_4$ is about 30-50 mm (e.g., about 41 mm), $D_5$ is about 25-45 mm (e.g., about 35 mm), $D_6$ is about 20-30 mm (e.g., about 26 mm), $D_7$ is about 40-60 mm (e.g., about 50 mm), and $D_8$ is about 20-30 mm (e.g., about 23 mm). Although specific dimensions are provided, it is to be understood that these dimensions are merely exemplary and other dimensions are possible depending on application. For example, the exemplary dimensions may vary by +/−10-20% or more or less depending on application.

Seal-Forming Structure 3100

In one form of the present technology, a seal-forming structure 3100 provides a sealing-forming surface, and may additionally provide a cushioning function.

In an example, a seal-forming structure 3100 in accordance with the present technology is constructed from a soft, flexible, resilient material such as silicone.

In one form, the seal-forming structure 3100 comprises a sealing flange 3110 and a support flange 3120. In one form of the present technology, sealing flange 3110 includes membrane 160 of the sealing region 151 and support flange 3120 includes undercushion or backup band 165 of the sealing region 151 (e.g., see FIG. 3-10). In an example, the sealing flange 3110 comprises a relatively thin member with a thickness of less than about 1 mm, for example about 0.25 mm to about 0.45 mm that extends around the perimeter 3210 of the plenum chamber 3200. In an example, the support flange 3120 is relatively thicker than the sealing flange 3110. The support flange 3120 is disposed between the sealing flange 3110 and the marginal edge 3220 of the plenum chamber 3200, and extends at least part of the way around the perimeter 3210 of the plenum chamber 3200. The support flange 3120 is a spring-like element and functions to support the sealing flange 3110 from buckling in use. In use the sealing flange 3110 can readily respond to system pressure in the plenum chamber 3200 acting on its underside to urge it into tight sealing engagement with the face.

In one form of the present technology, seal-forming structure 3100 comprises a superior sealing portion 3102 and an inferior sealing portion 3104 (e.g., see FIGS. 3-10 and 3-21). The superior sealing portion 3102 and the inferior sealing portion 3104 are, e.g., located adjacent one another, and one region may blend into the other.

Superior Sealing Portion 3102

Superior sealing portion 3102 is constructed and arranged to form a seal on a portion of the cartilaginous framework of the nose. In an example, superior sealing portion 3102 is constructed from a relatively thin material, e.g. a flap, flange or membrane of material e.g. a thermoplastic elastomer, or a silicone rubber, and further, e.g., one that readily bends or folds in response to light finger pressure when not in use. Depending on the shape of the nose with which it is being used, a relatively narrow width of superior sealing portion 3102 may engage with nose ridge to form a seal. A relatively wider portion of superior sealing portion 3102 may engage with the skin adjacent lateral nasal cartilage to form a seal. See, e.g., FIG. 3-39.

The superior sealing portion 3102 is not designed to overlay the whole of the nose.

In an example, the superior sealing portion 3102 is constructed and arranged, e.g. by being thin and flexible, to be adaptable to different heights of nose ridge. In this way, the range of faces that will be able to get a good seal is increased.

Furthermore, for a given face and nose, the flexibility of the superior sealing portion 3102 means that a seal may be maintained should the plenum chamber 3200 may be moved, e.g. in response to movement of the air circuit 4170.

While the superior sealing portion is constructed so that it does not overlay the nasal bones in use, certain portions of the superior sealing portion may overlay some part of the nasal bones on some faces, depending on exactly how the patient interface is used and the size and shape of the particular face.

In an alternative form, the superior sealing portion is constructed and arranged to form a seal on the nasal bones in use.

Inferior Sealing Portion 3104

Inferior sealing portion 3104 is constructed and arranged to form seal on a portion of the upper lip of a patient, and to direct at least part of a sealing force to the maxilla bone of the patient. In use, part of the inferior sealing portion 3104 is located close to the subalare and the alar crest point.

In one form, inferior sealing portion is configured to avoid excessive pressure on the upper teeth or gums. In an example, the inferior sealing portion does not extend along bone (e.g., frontal process of maxilla) superiorly to the alar crest point, however it should be appreciated that in other examples it might.

Inferior sealing portion 3104 may be constructed from a single, relatively thicker flap, rim or flange of material, e.g. a silicone rubber, or thermoplastic elastomer, e.g. with a thickness of about 1 mm to 2 mm. In one form, inferior sealing portion 3104 may be constructed from a dual flap, rim or flange, for example one being relatively thin and the other being relatively thick. Alternatively, inferior sealing portion 3104 may be constructed from a gel-filled bladder.

"W" Shaped Region

FIGS. 3-40-1 to 3-40-8 show various views of a cushion assembly 350 according to another example of the present technology. In this example, the cushion assembly includes a general "W" shape in the top lip region, i.e., general "W" shape along the outer (inferior) edge 360(o) of the membrane 360 in the top lip region as best shown in FIG. 3-40-4.

FIGS. 3-41-1 to 3-41-8 show various views of a cushion assembly 450 according to another example of the present technology. This example shows a cushion assembly with a general "W" shape in the top lip region. In contrast to the example of FIGS. 3-40-1 to 3-40-8, the cushion example of FIGS. 3-41-1 to 3-41-8 includes general "W" shape along both the inner (superior) edge 460(i) of the membrane 460 and the outer (inferior) edge 460(o) of the membrane in the top lip region as best shown in FIG. 3-41-4.

In one form, the "W" portion of the top lip region is constructed and arranged so that a middle portion of the "W" may rest on the subnasale or columella in use, in the event of the seal forming portion shifting upwards (superiorly) in use, leaving clearance (e.g., indicated by c in FIG. 3-41-8 which is between an inner edge of the undercushion 465 and an inner surface of the plenum chamber) around the respective left and right subalare.

In an example, as best shown in FIGS. 4-41-6, 3-41-7, and 3-41-10, a portion of the sealing portion may have a question-mark shaped, sickle shaped, or c-shaped cross-section. The question-mark shaped, sickle shaped, or c-shaped cross-section may provide the sealing portion with greater range of movement or flexibility towards the patient's face in use. In the illustrated example, the question-mark shaped, sickle shaped, or c-shaped cross-section is provided to a lower portion of the undercushion 465 and/or the side wall region 457, which provides a space below the lower portion of the undercushion 465 and adjacent the side wall region 457. For example, the lower portion of the undercushion 465 is radially offset towards the outside of the side wall region 457. It should be appreciated that such cross-section may be provided around the entire perimeter of the cushion or may only be provided in selected regions of the cushion, e.g., only in the top lip region. Also, the size and/or configuration of such cross-section may vary in selected regions.

In the illustrated example of FIGS. 3-40-1 to 3-40-8 and 3-41-1 to 3-41-8, $D_1$ is about 90-110 mm (e.g., about 105 mm), $D_2$ is about 40-60 mm (e.g., about 51 mm), $D_3$ is about 40-60 mm (e.g., about 51 mm), $D_4$ is about 35-55 mm (e.g., about 44 mm), $D_5$ is about 30-50 mm (e.g., about 38 mm), $D_6$ is about 25-35 mm (e.g., about 32 mm), $D_7$ is about 45-65 mm (e.g., about 58 mm), and $D_8$ is about 20-30 mm (e.g., about 26 mm). Although specific dimensions are provided, it is to be understood that these dimensions are merely exemplary and other dimensions are possible depending on application. For example, the exemplary dimensions may vary by +/−10-20% or more or less depending on application. For example, the sealing portion and aperture may be wider, e.g., $D_1$ is about 100-120 mm (e.g., about 114 mm), $D_6$ is about 40-50 mm (e.g., about 42 mm), $D_7$ is about 55-75 mm (e.g., about 68 mm), and $D_8$ is about 20-30 mm (e.g., about 24 mm). In another example, the sealing portion and aperture may be narrower, e.g., $D_1$ is about 90-110 mm (e.g., about 100 mm), $D_6$ is about 25-35 mm (e.g., about 28 mm), $D_7$ is about 45-65 mm (e.g., about 54 mm), and $D_8$ is about 20-30 mm (e.g., about 24 mm).

Sealing Region

In accordance with another form of the present technology seal forming structure 3100 comprises sealing region 151. Sealing region 151 may be adapted to interface with the patient and form a seal with the patient's airways. Sealing region 151 may include a nose ridge or nose ridge region 152, sides of the nose region 153, corners of the nose region 154 and top lip region 155. Sealing region 151 may comprise a membrane or flap type seal 160. In an example, as shown in FIGS. 3-18 and 3-19, the inner edge of the membrane 260 may includes a bead 260-1, e.g., to prevent tearing, enhance sealing along the edge. Sealing region 151 may further comprise an undercushion or backup band 165, extending around part of or the entire perimeter of the sealing region. A further aspect of the present technology is a cushion for a mask that seals at its upper extent in a region of the nose that is generally above the tip of the nose, and extends across the alar or flares of the patient's nose.

In an example, sealing region 151 may be preformed or otherwise pre-shaped so as to conform to that patient's facial topography.

Sealing Along Nasal Ridge

One aspect of the present technology relates to sealing of the sealing region in the nose ridge region. In an example, the sealing region in the nose ridge region is adapted to engage along the nasal ridge between the pronasale and sellion, and along the nasal cartilage region of the nasal ridge and below or inferior to the nasal bone. That is, the nasal mask system is constructed to have a seal-forming region that is substantially on at least part of the cartilaginous framework of the patient's nose and not on the nasal bone, i.e., seal along nasal ridge without contacting nasal bridge/skin on the nasal bone.

For example, the sealing region 151 is adapted to be positioned and seal at its upper extent in a region of the nose that is generally above the tip of the nose (i.e., above the pronasale), and extends across the alar or flares of the patient's nose, e.g., not extending over or across the bone of the patient's nose.

In an example, the sealing region 151 is positioned at its upper extent in a region of the nose that is generally close to the junction between bone and cartilage on a range of people with larger noses, and avoids impinging on the sight of people with smaller noses.

Nose Ridge Region

Nose ridge region 152 may be adapted to engage with a nose ridge of a patient. In an example, the nose ridge region may be shaped or preformed to accommodate a patient's nose ridge, for example, as best shown on. FIG. 3-7, the nose ridge region may be lower (i.e., closer to the attachment region 158) than the sides of the nose region 153. Nose ridge region 152 may comprise a membrane 160 for sealing without an undercushion or backup band. In an example, such an arrangement prevents excess pressure on the sensitive nose ridge region. In an example, the membrane at the nose ridge region 152 may be relatively longer that the membrane in other regions of the seal region, for example the top lip region 155. The membrane in the nose ridge region 152 may be, for example, about 2-5 mm in length. In an example, the membrane in the nose ridge region 152 may be about 2-4 mm in length. In an example, the membrane in the nose ridge region 152 may be about 3 mm in length.

Sides of the Nose Region

Sides of the nose region 153 may be adapted to engage with the sides of a patient's nose. In an example, sides of the nose region 153 may be preformed to accommodate the sides of the patient's nose and potentially their cheeks. As best shown on FIG. 3-5, sides of nose the region 153 extends from the apex of the cushion at nose ridge region 152 to the corners of the nose region 154. The sides of nose the region 153 slopes upwardly from the nose ridge region 152 to the corners of the nose region, see for example FIG. 3-6. Sides of the nose region 153 may comprise a membrane 160 for sealing without an undercushion or backup band. In an example, such arrangement prevents excess pressure on the sides of the patient's nose or alar or flares. Excess pressure on these regions may cause the cartilage of the nose to collapse inwardly towards the septum, thereby occluding or partially occluding the patient's airway.

Corners of the Nose Region

Corners of the nose region 154 may be adapted to form a seal with the corners of the patient's nose. FIG. 3-6 shows the corners of the nose region 154 having an apex or point generally indicated by $H_1$, being the maximum height of the sealing region 151. This height is to ensure that the most force is applied to the sealing region 151 in the corners of the nose region 154, as this is a boney region of the face and is therefore less sensitive to pressure. Furthermore, this region of the patient's face is particularly difficult to seal on as the geometry of the face in this region is quite complex, so the greater the force applied to the seal in this region, the more likely a seal will form. In addition, since lower sealing forces are required on the nose ridge region and the sides of the nose region (for comfort and to avoid occlusion), the sealing region must be anchored at the corners of the nose region. Corners of the nose region 154 may comprise a membrane or membrane seal 160 and an undercushion or backup band 165. The use of both a membrane and an undercushion may ensure a higher sealing force in this region. In an example, the membrane may have a thickness about 0.1-0.5 mm, for example about 0.3 mm. In an example, the undercushion may have a thickness of about 0.3-2 mm.

Top Lip Region

Top lip region 155 may be adapted to engage the surface between the patient's top lip and base of the nose. In an example, top lip region may have a relatively shorter membrane length than the nose ridge region, for example a length of about 0.5-2.5 mm, e.g., about 1.5-2.5 mm. In an example, this shorter membrane length may be advantageous as some patient's only have a small space between their top lip and the base of their nose. As best shown in FIG. 3-10, top lip region 155 may have a membrane seal 160 and an undercushion or backup band 165. The use of both a membrane and an undercushion may ensure a higher sealing force in this region. In an example, the membrane may have a thickness about 0.1-0.5 mm, for example about 0.3 mm. In an example, the undercushion may have a thickness of about 0.3-2 mm, for example about 1.5 mm. In an example, the thickness of the undercushion may vary along the length of the top lip region, for example from about 0.3 mm at the corners of the nose region, to about 1.2 mm at the centre of the top lip region.

Seal

Use of the undercushion or back-up band enables the membrane or facial flap to be made considerably thinner than if a single unsupported flap were used. This is highly advantageous in that a thinner flap is in turn more flexible, so as to feel softer and more comfortable and more readily conform to irregularities in the facial contour. It also permits the flap to more readily respond to system pressure in the breathing chamber acting on its underside to urge it into tight sealing engagement with the face.

As noted above, the nasal mask system is constructed to have a seal-forming region that is substantially on the cartilaginous framework on the nose (i.e., not on the nasal bone), and which does not block the nose. In an example, this may be achieved by providing a compression seal (e.g., using an undercushion structure) along the patient's top lip (e.g., inferior sealing portion) and not on the patient's nose. Seal on the patient's nose (e.g., superior sealing portion) may be achieved by tension in the membrane and/or a pneumatic seal.

For example, as shown in the cushion example of FIGS. 3-14 to 3-30 and also described in the above example, the undercushion or backup band 265 is only provided in the top lip region 255 and the corners of the nose region 254 of the cushion, e.g., see FIGS. 3-16, 3-18, 3-22, 3-23, 3-29, and 3-30. That is, the sealing region includes a single layer membrane 260 only structure in the nose ridge region 252 and sides of the nose region 253 (e.g., see FIGS. 3-18 and 3-22 to 3-28), and the sealing region includes a dual layer or membrane 260 and undercushion 265 structure in the top lip region 255 and corners of nose region 254. The dual layer structure provides a compression seal along the top lip region and corners of nose region. In contrast, the nose ridge region and sides of the nose region uses tension in the membrane (edge of the membrane stretched into sealing engagement due to tension applied to membrane) and/or pressure in the breathing chamber acting on the membrane (pneumatic seal) to provide a seal. The single layer is also provided in the nose ridge region and sides of the nose region to provide a softer and more flexible seal that avoids any potential for blocking the patient's nose, i.e., prevents excess pressure on the sides of the patient's nose or alar or flares which may cause the cartilage to collapse inwardly and potentially at least partially occlude the patient's airway.

Thus, the cushion assembly according to an example of the present technology provides different sealing mechanisms in different portions of the cushion. For example, the cushion assembly may provide one mechanism of sealing in the superior portion of the cushion (e.g., sealing by tension in the membrane and/or a pneumatic seal) and a different mechanism of sealing in the inferior portion of the cushion (e.g., compression seal). In the illustrated example, the cushion assembly provides a compression seal via a dual layer or membrane and undercushion structure. However, it should be appreciated that the compression seal may be provided by alternative structures, e.g., gel-filled or foam-filled pocket, thicker single wall (e.g., about 0.8 to 1.2 mm thick silicone).

FIGS. 3-38 shows an example of the cushion assembly 250 engaged with the patient's face and under pressure or inflated in use, i.e., supply of air at positive pressure being applied to the cushion assembly 250. FIG. 3-39 shows a hatched area along the sealing portion of the cushion assembly which illustrates a width or contact area 280 of the sealing portion engaged with the patient's face in use. The width or contact area includes an inner edge 280(*i*) (e.g., along the edge of the orifice) and an outer edge 280(*o*). FIG. 3-36 also shows the outer edge 280(*o*) of the contact area in dashed lines. As illustrated, a relatively narrow width of superior sealing portion 3102 may engage with the nose ridge to form a seal, e.g., depending on the shape of the nose with which it is being used. A relatively wider portion of superior sealing portion 3102 may engage with the skin adjacent lateral nasal cartilage to form a seal. In the inferior sealing portion 3104, substantially the entire width of the inferior sealing portion may engage the skin along the corner of nose region and top lip region to form a seal. Thus, the width or contact area of the sealing portion engaged with the patient's face in use may vary around the perimeter of the cushion assembly to form a seal.

Sealing Flap

In an example, as shown in FIGS. 3-14, 3-16, 3-20, 3-22, 3-26, 3-27; 3-35, and 3-36, each side of nose region 253 of the sealing region includes a portion 270, e.g., a wing or sealing flap, that protrudes from the edge of the membrane 260 along its inner perimeter. As best shown in FIGS. 3-35 and 3-36, each sealing flap 270 is adapted to form a seal on the region adjacent the junction between the nasal greater alar cartilage and the lateral nasal cartilage of a patient's nose (also referred to as the alar crease). The exact location of the sealing flap on a face in use may vary depending on the size and shape of the nose with which it is being used.

As illustrated, each sealing flap 270 is at least partially angled or pre-biased outwardly away from the breathing chamber of the cushion. When engaged with the patient's nose, the sealing flaps are deflected towards the breathing chamber which provides a bias for sealing in the junction noted above. That is, the shape, flexibility, and pre-bias of the sealing flaps allows the flaps to accommodate changes in curvature or contour in this junction (e.g., which tend to continually vary when the nasal alar or "flare" in use) so as to maintain seal and prevent leaks in use.

In an example, the sealing flange (including membrane 260 and sealing flap 270) defines a generally T-shaped orifice. The edge of the membrane 260 along its inner perimeter along with the edge of each sealing flap 270 along its inner perimeter cooperate to define an orifice 275 into the plenum chamber. In an example, such orifice 275 includes a general T-shape including an upper orifice portion 275(1) (along vertical axis v as viewed in FIG. 3-20) and a lower orifice portion 275(2) (along horizontal axis h as viewed in FIG. 3-20) that extends generally transverse to the upper orifice portion 275(1).

As best shown in FIG. 3-14, the sealing flap 270 changes the curvature and/or angle of the edge defining the orifice 275, i.e., edge of the orifice 275 curves upwardly and outwardly away from the breathing chamber at least along the sealing flap 270.

Curvature

The curvature of the cushion may vary along the patient contacting surface of the membrane 260 in different regions of the cushion, e.g., to facilitate sealing in different regions of the patient's face.

For example, as shown in FIG. 3-14, the nose ridge region 252 and the top lip region 255 each include at least a portion that is locally saddle-shaped in curvature, e.g., curves up in one direction d1 and curves down in a different direction d2. FIG. 3-37 is another view of the cushion 250 illustrating such saddle-shaped curvature in the nose ridge region 252 and the top lip region 255.

It should be appreciated that the above-noted shapes of curvature are approximate shapes and should not be limited to strict mathematical definitions of such shapes.

In addition, it should be appreciated that regions may include similar curvature shapes, but the magnitudes of such curvature may be different. For example, the nose ridge region 252 and the top lip region 255 may both include at least a portion that is locally saddle-shaped, however the magnitude of curvature in one and/or both principle directions of such saddle-shape may be different in each region.

Aperture

In an example, where a single mask should be used to fit about 85% of the female population, the undercushion aperture width (e.g., indicated at uw in FIG. 3-41-9 for example) is about 36 mm to about 42 mm, or about 38 mm to about 40 mm. In an example, where a single mask should be used to fit about 85% of the male population, the undercushion aperture width is about 40 mm to about 46 mm, or about 42 mm to about 44 mm. In one form, to account for nose width variations of various ethnicities, to fit up to 95% of an average population, an undercushion aperture width is about 50 mm to about 56 mm, or about 52 mm to about 54 mm.

In an example, where a single mask should be used to fit about 85% of the female population, the membrane aperture width (e.g., indicated at mw in FIG. 3-41-9 for example) is about 23 mm to about 29 mm, or about 25 mm to about 27 mm. In an example, where a single mask should be used to fit about 85% of the male population, the membrane aperture width is about 39 mm to about 45 mm, or about 41 mm to about 43 mm. In one form, to account for nose width variations of various ethnicities, to fit up to 95% of an average population, a membrane aperture width is about 49 mm to about 55 mm, or about 51 mm to about 53 mm.

Plenum Chamber 3200

Plenum chamber 3200 is formed in part by a side wall. In one form, the side wall includes side wall region 157 of sealing region 151. The plenum chamber has a perimeter 3210 that is shaped to conform generally to the surface contour of the face of an average person (e.g., see FIGS. 3-8 and 3-9). In use, a marginal edge 3220 of the plenum chamber 3200 is positioned in close proximity to an adjacent surface of the face (e.g., see FIG. 3-10). Actual contact with the face is provided by the seal-forming structure 3100. In an example, the seal-forming structure 3100 extends in use about the entire perimeter 3210 of the plenum chamber 3200. In an example, the plenum chamber is adapted to receive a portion of the patient's nose including the pronasale, e.g., the plenum chamber forms over and surrounds a portion of the cartilaginous framework of the nose including the pronasale.

In an example, the walls of the plenum chamber 3200 are flexible, or semi-rigid. In an example, plenum chamber 3200 does not include a rigid frame or shell. In an example, the walls of the plenum chamber 3200 are not rigid, and, e.g., the walls of the plenum chamber 3200 are not floppy. In certain forms, flexibility of the walls of the plenum chamber 3200 assists to decouple a tube drag force from disrupting a seal.

In one form, the walls of the plenum chamber 3200 are moulded from a silicone rubber. In an example, the walls of the plenum chamber 3200 are constructed from a silicone rubber with a Type A indentation hardness of about 35 to about 40, and with a thickness in the range of about 2 mm to about 4 mm. In certain forms of the present technology, the plenum chamber 3200 may have different thicknesses in different regions.

Side Wall Region

Side wall region 157 may extend between sealing region 151 and attachment region 158. Side wall region may be generally conical, that is, it may have a first diameter at proximate attachment region 158 and a second diameter proximate seal region 151, with the first diameter being less than the second diameter. Side wall region may have a thickness of about 1.5-5 mm, e.g., about 1.5-3 mm, e.g., about 2 mm. Such a thickness may provide some support to the seal region 151, prevent the elbow assembly 120 contacting the patient's nose, and ensure that the cushion does not collapse from headgear tension when in use.

Side wall region 157 may connect or be formed with headgear connectors 156. Such an arrangement may replace the need for a rigid frame or skeleton, as the headgear connectors are arrange proximal to the sealing region 151. Headgear connectors 156 may be disposed on opposing sides of side wall 157.

Thinner Wall Section

In an example, as best shown in FIGS. 3-16, 3-18, 3-23, and 3-30, the side wall region 257 between the sealing region 251 and the attachment region 258 includes an area 268 adjacent the top lip region 255 of the sealing region that includes a thickness that is less than corresponding thicknesses adjacent the nose ridge, sides of nose, and corners of nose regions of the sealing region. That is, the area 268 includes a thinner walled cross-section adjacent the top lip region 255 of the sealing region. Such area 268 of thinner cross-section lessens the force provided by the sealing region along this section of the top lip region 255. For example, such area 268 provides less pressure along the top lip region 255 than the corners of nose region 254 (i.e., stiffer along the corners of nose region than the top lip region thereby giving rise or effecting relatively greater pressure along the corners of nose region (along the corners of the lip adjacent the alars), in order to avoid excessive pressure on the columella or septum of the patient's nose which is a more sensitive region of the patient's nose.

FIGS. 3-22 to 3-30 show exemplary cross-sectional views through various regions of the cushion assembly 250. For example, FIG. 3-23 is a cross-sectional view through the nose ridge region 252 and the top lip region 255 showing the single layer or membrane 260 only structure in the nose ridge region 252 and the dual layer or membrane 260 and undercushion 265 structure in the top lip region 255. FIG. 3-23 also shows the thinner cross-section area 268 in the side wall region 257 adjacent the top lip region 255, e.g., to avoid excessive pressure on the columella or septum. In addition, FIG. 3-23 shows the attachment region 258 including thinner wall section 258(1), e.g., to permit decoupling of tube drag forces. FIGS. 3-24 and 3-25 show the single layer or membrane 260 only structure in the sides of the nose region 253. FIGS. 3-26 and 3-27 also show the single layer or membrane 260 only structure in the sides of the nose region 253 as well as at least part of the wing or sealing flap 270 that protrudes from the edge of the membrane 260. FIGS. 3-27 and 3-28 show at least part of the headgear connector 256. FIGS. 3-29 and 3-30 show the dual layer or membrane 260 and undercushion 265 structure in the corners of nose region 254 and the top lip region 255. FIG. 3-30 shows the thinner cross-section area 268 in the side wall region 257 adjacent the top lip region 255.

Positioning and Stabilising Structure 3300

In an example, the seal-forming portion 3100 of the patient interface 3000 of the present technology is held in sealing position in use by the positioning and stabilising structure 3300.

In one form, the seal-forming portion 3100 of the patient interface 3000 of the present technology is held in sealing position via a two-point connection to a positioning and stabilising structure 3300.

In one form, the positioning and stabilising structure 3300 connects to plenum chamber 3200 via headgear connector 156.

In an example, there are only two connectors 156 to the plenum chamber 3200.

Headgear Connector

Headgear connector 156 may comprise a lug or interface 159 adapted to receive a cushion connector 116 on headgear 110. A similar arrangement is disclosed in PCT application number PCT/AU2008/001557, filed 22 Oct. 2008, which is incorporated herein by reference in its entirety.

Headgear connectors 156 may be positioned at an angle relative to the vertical axis of the seal region 151. As best shown in FIGS. 3-6 and 3-7, headgear connectors 156 may be positioned at angle α relative to the vertical axis of the seal region 151. In an example, angle α may be approximately 90-135°. In an example, angle α may be approximately 90-120°. In an example, angle α may be approximately 90-100°. Angle α aligns the headgear connectors in such a way so as to ensure a sealing force between the cushion and the patient is sufficient to effect a seal without causing discomfort or causing the cushion to collapse (for example, the closer angle α is to 180°, the more likely the cushion is to collapse inwardly towards the vertical axis when headgear tension is applied, thus pinching the patient's nose), particularly in the sides of the nose region 153 of sealing region 151.

In an alternative example, as best shown in FIGS. 3-40-1, 3-40-3, 3-40-5, 3-40-6, 3-41-1, 3-41-3, 3-41-5, 3-41-6, a hinge or thinner wall section 356(1), 456(1) may be provided to each headgear connector 356, 456 to enhance flexibility of the headgear connectors and allow sufficient bending in use so headgear tensioning force is not transferred to collapse the cushion inwardly, e.g., to avoid pinching of the alar under headgear tension. Also, as shown in FIG. 3-41-6, one or more wall sections 457(1) of the side wall region 457 between the lugs of the headgear connectors may be thickened, e.g., to prevent or reduce collapse of the side wall region under headgear tension.

Headgear connectors 156 may be positioned at an angle relative to the horizontal axis of the seal region 151. As best shown in FIG. 3-9, headgear connectors 156 may be positioned at angle β relative to the horizontal axis of the seal region 151. In an example, angle β may be approximately 90-135°. In an example, angle β may be approximately 90-120°. In an example, angle β may be approximately 90-100°. Angle β aligns the headgear connectors in such a way so as to ensure the sealing force provided by the headgear connectors 156 is distributed over the sealing region 151, with more force provided in the top lip region 155 and corners of the nose region 154, and less force provided in the nose ridge region 152. Such distribution may be more comfortable and stable.

As shown in FIG. 3-8, headgear connectors 156 may have a first width $w_1$ at a region proximal to the side wall 157, and a second width $w_2$ at its extremity, with first width $w_1$ being greater than second width $w_2$. In an example, first width $w_1$ may be about 15-50 mm. In an example, first width $w_1$ may be about 15-30 mm. In an example, first width $w_1$ may be about 20-25 mm. In an example, second width $w_2$ may be about 15-30 mm. In an example, second width $w_2$ may be about 15-25 mm. In an example, second width $w_2$ may be about 15-20 mm. First width $w_1$ ensures that the force provided by the headgear is spread from the sides of the nose region 153 to the corners of the nose region 154, and also stabilizes the cushion in the horizontal plane. Second width $w_2$ is arranged to reduce the visual bulk of the headgear connector 156 and permit connection with cushion connector 116.

Headgear connectors 156 are advantageously disposed proximal to the sealing region 151. Headgear connectors 156 are positioned at a height $H_1$ from the sealing region 151, as shown on FIG. 3-6. In an example, height $H_1$ may be approximately 10-50 mm. In an example, height $H_1$ may be approximately 10-30 mm. In an example, height $H_1$ may be approximately 10-20 mm. In an example, height $H_1$ may be approximately 20-30 mm. This arrangement ensures that headgear forces are translated directly to the sealing portion, and the sealing region is able to wrap or conform to the patient's nasal geometry.

The position and size of the headgear connectors directs the sealing force to the sealing region in such a way so as to negate or eliminate the need for a forehead support or vertical headgear strap. For example, the width of the headgear connectors proximal to the side wall stabilizes the sealing region on the patient's face. The height of the headgear connectors 156 to the sealing region 151 ensures that headgear forces are translated directly to the sealing portion, thereby eliminating the need for additional stabilization from a forehead support.

In an alternative form of the present technology, headgear connectors 156 are formed separately from the plenum chamber.

Headgear Assembly

One form of positioning and stabilising structure 3300 in accordance with the present technology is headgear assembly 110. Headgear assembly 110 may be adapted to support, stabilize and/or position the cushion assembly 150 on the patient's face.

As shown in FIGS. 3-1 to 3-3, headgear assembly 110 may comprise a pair of side straps 115, connected to a rear strap 118. Side straps 115 define a main headgear loop that may be positioned along the sides of the patient's face, across the patient's cheeks, extending between the eyes and the ears of the patient, e.g., overlaying at least a portion of the zygomatic bone, towards the crown of the patient's head where it e.g., overlays a portion of the parietal bone. Side straps 115 may have a cushion connector 116 adapted to receive a headgear connector 156 of cushion 150. Side straps 115 may have an adjustment portion 117, wherein side straps 115 interlock or otherwise connect to each other and are able to adjust in length relative to one another. Rear strap 118 extends between the side straps and may loop through a respective slot 114 provided to the side straps 115. Rear strap 118 defines a rear headgear loop that may be positioned over the back of the patient's head, e.g., engaging along or below the patient's occiput. In an example, a portion of the headgear rear strap 118 or rear headgear loop overlays or engages a point on the head below or inferior to the occipital bone, e.g. a portion of the strap lies on a portion of the trapezius muscle, adjacent the occipital bone in use. In an example, at least a portion of the rear strap 118 engages below or inferior a lower edge of the occipital bone, which lower edge helps to maintain the rear strap in position and prevent the rear strap from riding up the patient's head, e.g., prevent sliding in a superior direction. Refer to FIGS. 2i and 3-2 for location of the trapezius and an exemplary positioning of the rear strap 118 along a portion of the trapezius. In an example, the headgear straps are sufficiently stretchy or flexible, e.g., to enhance comfort and adjustability. For example, the headgear may not require length adjustment to don.

In one form, headgear assembly 110 comprises a silicone main portion and a fabric rear portion. In another form, headgear assembly 110 comprises a fabric main portion and a fabric rear portion. In another form, headgear assembly 110 comprises a silicone main portion and a silicone rear portion.

In one form, headgear assembly 110 is constructed and arranged to be substantially floppy.

In one form, headgear assembly 110 comprises a main structural tie, and a rear structural tie.

An exemplary headgear assembly 110 is disclosed in PCT application number PCT/AU2008/001557, filed 22 Oct. 2008, which is incorporated herein by reference in its entirety.

Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

In an example, the vent 3400 is located in a decoupling structure 3500, e.g. a swivel 3510. Alternatively, the vent 3400 is located in the plenum chamber 3200.

One form of vent 3400 in accordance with the present technology is vent 126. Vent 126 may permit to expiration of exhaled gases from the nasal mask system. Vent 126 may comprise a series of holes, a mesh or other arrangement adapted to permit the flow of gas. In an example, vent 126 may be sufficiently rigid to avoid collapse of the air channels that exhaust the exhaled gas. Vent 126 may be positioned on the elbow 125 or other region such as the air delivery tube assembly 130 or cushion assembly 150 (including, for example, side wall 157).

In certain forms of the present technology, the vent 3400 may be constructed from a flexible, or floppy material that is supported by a sufficiently rigid frame to avoid collapse of the air channels that exhaust the exhaled gas.

In an alternative form, the patient interface 3000 does not include a vent.

Decoupling Structure(s) 3500

In one form the patient interface 3000 includes at least one decoupling structure 3500, for example a swivel 3510 or a ball and socket 3520 (e.g., see FIG. 3-13). In one form, decoupling structure 3500 may be formed at least in part by attachment region 158.

Attachment Region

Attachment region 158 may be adapted to receive elbow assembly 120. Attachment region 158 may include a thinner wall section 158(1) than the side wall region 157, for example attachment region 158 may have a wall section of about 0.1-1 mm, for example about 0.2-0.8 mm, for example about 0.5 mm. In an example, the thinner wall section is configured to permit decoupling of the tube drag forces from the sealing forces.

Connection Port 3600

In one form, connection port 3600 to air circuit 4170 is made by elbow assembly 120 (e.g., see FIGS. 3-1 and 3-2).

Elbow Assembly

Elbow assembly 120 may be adapted to connect or serve as an interface between the cushion assembly 150 and the air delivery assembly 130. Elbow assembly 120 may be formed with or integral with the air delivery assembly 130, or cushion assembly 150. Elbow assembly 120 may also be adapted to permit exhaust of exhaled gases.

As shown in FIGS. 3-1 to 3-3 and 3-11 to 3-13, elbow assembly 120 may comprise an elbow 125, the elbow having a vent 126, the elbow connecting to or otherwise formed with connector ring 128. Elbow 125 may be formed with a ball joint and the connector ring 128 may for constructed and arranged to permit rotation of the ball joint while ensuring a sufficient seal with the elbow to ensure air leakage does not compromise the patient's treatment pressure. The ball joint provides a decoupling mechanism, e.g., decouple tube drag forces from sealing forces.

Elbow 125 may also be attached to or otherwise connected with swivel 129, adapted to receive an air delivery tube assembly 130. Swivel 129 may be arranged such that it may form a seal or have a low leak with elbow 125, while still being able to freely rotate relative to elbow 125.

Forehead Support

In an example, the patient interface 3000 does not include a forehead support, however in one alternative form, a forehead support may be included.

Anti-Asphyxia

In one form, the patient interface 3000 includes an anti-asphyxia valve.

Ports

In one form of the present technology, a patient interface 3000 includes one or more ports, that allow access to the volume within the plenum chamber 3200. In one form this allows a clinician to supply supplemental oxygen. In one form this allows for the direct measurement of a property gases within the plenum chamber 3200, such as the pressure.

Air Circuit 4170

An air circuit 4170 in accordance with one form of the present technology is air delivery assembly 130. Air delivery assembly 130 may be constructed to connect a flow generator, to mask system 100. As shown in FIGS. 3-1 to 3-3, air delivery system 130 may comprise a tube 133 and a connector 135. Tube 133 may be relatively flexible. Connector 135 may be adapted to receive swivel 129 of elbow assembly 120.

Donning and Removing

The nasal mask system provides a small, unobtrusive mask system that is easy to don, easy to remove, is stable, comfortable, effective, provides wide-fit range, unobtrusive, easy to use, and adjustable. In addition, the nasal mask system provides a non-prong or non-pillows arrangement (i.e., nasal mask system provides nasal-type cushion that provides single orifice adapted to surround both nares in use) that does not suffer from problems of jetting effect, nor the potential discomfort associated with nasal prongs or pillows adapted to at least partially extend up the patient's nose. The nasal mask system is structured such that little or no adjustment may be needed to fit the nasal mask system to the patient's head. In an example, no forehead support is provided to the mask system, though one can be provided if desired.

In the illustrated example, the nasal mask system 100 provides a two-point connection with the cushion, i.e., two side straps 115 of the headgear assembly engage respective headgear connector 156 along side of the cushion 150 (e.g., see FIGS. 3-1 to 3-3). The headgear assembly provides three adjustment points, e.g., adjustable portion 117 of the side straps 115 and respective adjustability of ends of the rear strap 118 with a respective slot 114 of the side straps 115. However, it should be appreciated that more or fewer adjustment points may be provided, e.g., side straps and rear strap may provide fixed length with no adjustability.

In an example, the two-point connection does not does not require engagement or disengagement of a clip in order to don or remove the mask system, i.e., no clips are provided to the mask system but they can be provided if desired. Also, the main headgear loop defined by the side straps 115 extends from an inferior anterior position to a superior posterior position, which avoids any headgear strap extending below the ears (i.e., straps do not pass inferior to the patient's ear) as described below.

FIGS. 3-31 to 3-34 provide a sequence of views to illustrate an exemplary method for fitting the nasal mask system to a patient, e.g. prior to the application of air pressure to the plenum chamber. As shown in FIG. 3-31, the patient may grasp the nasal mask system such that one hand holds the cushion assembly 150 in a manner to orient the sealing region towards the patient's face and the other hand holds the rear strap 118 in a manner to allow the main headgear loop defined by the side straps 115 to receive the patient's head. Then, as shown in FIG. 3-32, the cushion assembly is engaged with the patient's face, and the rear strap is held over the patient's head as it passes through the main headgear loop. The rear strap, along with the side straps attached thereto, may be pulled onto the patient's head until the rear strap is positioned along the back of the patient's head as shown in FIG. 3-33, i.e., straps rotated or pivoted about the cushion assembly onto the patient's head until the straps engage and self-locate onto the patient's head. Finally, as shown in FIG. 3-34, ends of the rear strap 118 and/or the adjustment portion 117 of the side straps may be adjusted as necessary to secure the nasal mask system on the patient's head.

This arrangement is simple to put on and take off as the straps do not have to be pulled down over the ears to don the mask system or pulled up over the ears to remove the mask system, i.e., headgear straps easily slid on/off over the patient's head like a cap. That is, the mask system includes headgear that may be donned and removed like a cap without interfering with the ears of the patient.

In use, the side straps 115 are arranged to pull the nasal mask system in a superior posterior direction (e.g., as indicated by the arrow a1 in FIG. 3-34), which provides less compressive force along the nose ridge region of the cushion assembly 150 which is advantageous as such region is along a more sensitive region of the patient's nose, i.e., along the cartilage of the nose (not bone) as described above. Masks with nasal-type cushions normally include headgear arrangements arranged to pull the mask along a direction that is substantially parallel to Frankfort horizontal (as indicated by the arrow a2 in FIG. 3-34) so as to provide a compressive sealing force substantially normal to the patient's face. To provide such force, the headgear arrangement includes straps that extend under the patient's ears so as to provide such force along the Frankfort horizontal direction. In the mask system according to an example of the present technology, the headgear assembly is arranged to pull the mask along the superior posterior direction, e.g., like an "under the nose" mask (e.g., pillows or cradle), which provides less compressive force along the nose ridge region while maintaining sufficient seal as noted above. Thus, the nasal mask system provides headgear that provides an effective sealing vector similar to "under the nose" masks (i.e., not parallel to Frankfort horizontal), but instead used for mask that covers part of the nose, i.e., the nasal mask system compromises sealing force strictly along the Frankfort horizontal for an over the ear headgear arrangement to facilitate donning.

9.3.13 Pivoting Adjustment of Plenum Chamber

FIG. 3-9 shows a perpendicular distance $h_3$ between a headgear connection point hp, i.e., line of headgear tension as headgear connects to the cushion assembly 150, and a pivoting point or rotation axis pp of the cushion assembly 150 on the face, i.e., the top lip. This perpendicular distance $h_3$ allows adjustment of the headgear tension to effect rotational or pivotal adjustment of the plenum chamber/cushion assembly about the pivoting point pp. As illustrated, the headgear connection point hp is superior to the pivoting point pp or point of contact of the cushion assembly with the top lip. This arrangement enables a user to rotate/pivot the cushion assembly via adjustment of headgear tension and to use only a two point headgear connection to accommodate different nose ridge geometry. In an example, increasing the perpendicular distance $h_3$ will increase the moment.

Pap Device 4000

A PAP device 4000 in accordance with one aspect of the present technology comprises mechanical and pneumatic components, electrical components and is programmed to execute one or more algorithms. In an example, PAP device has an external housing, e.g., formed in two parts, an upper portion 4012 of the external housing, and a lower portion 4014 of the external housing. In alternative forms, the external housing may include one or more panel(s) 4015. In an example, the PAP device 4000 comprises a chassis 4016 that supports one or more internal components of the PAP device 4000. In one form a pneumatic block is supported by, or formed as part of the chassis 4016. The PAP device 4000 may include a handle 4018.

In an example, pneumatic path of the PAP device 4000 comprises an inlet air filter 4112, an inlet muffler, a controllable source of air at positive pressure (e.g., a blower 4142), and an outlet muffler. One or more pressure sensors and flow sensors are included in the pneumatic path.

In an example, pneumatic block comprises a portion of the pneumatic path that is located within the external housing.

In an example, the PAP device 4000 has an electrical power supply 4210, one or more input devices 4220, a processor, a pressure device controller, one or more protection circuits, memory, transducers, data communication interface and one or more output devices. Electrical components may be mounted on a single Printed Circuit Board Assembly (PCBA) 4202. In an alternative form, the PAP device 4000 may include more than one PCBA 4202.

The processor of the PAP device 4000 is programmed to execute a series of algorithm modules in use, e.g., including pre-processing transducer signals module, a therapy engine module, a pressure control module, and further e.g., a fault condition module.

GLOSSARY

In certain forms of the present technology, one or more of the following definitions may apply. In other forms of the present technology, alternative definitions may apply.

General

Air: Air will be taken to include breathable gases, for example air with supplemental oxygen.

Positive Airway Pressure (PAP): PAP treatment will be taken to mean the application of a supply of air or breathable gas to the entrance to the airways at a pressure that is positive with respect to atmosphere. In one form, the pressure will be continuously positive (CPAP) and e.g., approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms the pressure will be a number of centimeters, e.g. about 5-15 cm of water pressure higher during inhalation than exhalation, and provide ventilatory support. In some forms, the pressure will vary between different respiratory cycles of the patient, for example being increased in response to detection of indications of partial upper airway obstruction, and decreased in the absence of indications of partial upper airway obstruction.

Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises e.g. the nasal bones, the frontal process of the maxillae and the nasal part of the frontal bone.

(nose) Cartilaginous framework: The cartilaginous framework of the nose comprises, e.g., the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity-(or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow or air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. In an example, the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane, e.g., in the context of a sealing portion and/or face-contacting portion, will be taken to mean a typically thin element that has, e.g., substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: In an example, a shell will be taken to mean a curved structure having bending, tensile and compressive stiffness, for example, a portion of a mask that forms a curved structural wall of the mask. In an example, compared to its overall dimensions it is relatively thin. In some forms, a shell may be faceted. In an example, such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, e.g., independently, e.g., under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components, e.g., comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

Terms Used in Relation to Patient Interface

Floppy: A quality of a material, structure or composite that is the combination of features of:

Readily conforming to finger pressure.

Unable to retain its shape when caused to support its own weight.

Not rigid.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used or as being an example to construct a component, obvious alternative materials with similar properties may be used as a substitute.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

REFERENCE SIGNS LIST nasal mask system 100
headgear assembly 110
slot 114
side straps 115
cushion connector 116
adjustment portion 117
rear strap 118
elbow assembly 120
elbow 125
vent 126
connector ring 128
swivel 129
air delivery assembly 130
tube 133
connector 135
cushion assembly 150
sealing region or sealing cuff 151
nose ridge region 152
side of nose region 153
corner of nose region 154
top lip region 155
headgear connectors 156
side wall region or side wall 157
attachment region 158
thinner wall section 158(1)
lug 159
membrane 160
undercushion or backup band 165
cushion assembly 250
sealing region 251
nose ridge region 252
side of nose region 253
corner of nose region 254
top lip region 255
headgear connector 256
side wall region 257
thinner wall section 258(1)
attachment region 258
membrane 260
undercushion or backup band 265
area of thinner cross-section 268
sealing flap or wing 270
orifice 275
upper orifice portion 275(1)
lower orifice portion 275(2)
contact area 280
inner edge 280(i)
outer edge 280(o)
cushion assembly 350
hinge 356(1)
membrane 360
outer edge 360(o)
cushion assembly 450
hinge 456(1)
side wall region 457
wall section 457(1)
membrane 460
outer edge 460(o)
inner edge 460(i)
undercushion 465
sickle shaped cross-section 466
patient 1000
bed partner 1100
patient interface 3000
seal forming structure 3100
superior sealing portion 3102
inferior sealing portion 3104
sealing flange 3110
support flange 3120
plenum chamber 3200
perimeter 3210
marginal edge 3220
positioning and stabilising structure 3300
vent 3400
decoupling structure 3500
swivel 3510
socket 3520
connection port 3600
pap device 4000
upper portion 4012
lower portion 4014
panels 4015
chassis 4016
handle 4018
inlet air filter 4112
blower 4142
air circuit 4170
PCBA 4202
electrical power supply 4210
input devices 4220
humidifier 5000

What is claimed is:

1. A nasal mask for delivery of a supply of air to an entrance of a patient's airways, the nasal mask comprising:
a superior sealing portion and an inferior sealing portion,
wherein the superior sealing portion and the inferior sealing portion provide a sealing region including a flexible membrane adapted to engage a patient's face and form a seal around both nares of a patient's nose,
wherein the superior sealing portion is constructed and arranged to be substantially located on and to form a seal with a portion of the cartilaginous framework of a patient's nose,
wherein the superior sealing portion comprises the flexible membrane without an undercushion or backup band to provide a first sealing mechanism,
wherein the inferior sealing portion is constructed and arranged to be located in part on a portion of an upper lip of a patient and to direct a sealing force to a portion of a maxilla bone of the patient, wherein the inferior sealing portion comprises the flexible membrane and an undercushion or backup band to provide a second sealing mechanism that is different than the first sealing mechanism, and wherein the first and second sealing mechanisms are configured and arranged around a perimeter of the sealing region such that a contact area of the sealing region engaged with the patient's face in use varies around the perimeter of the sealing region to form the seal around both nares of the patient's nose.

2. The nasal mask according to claim 1, wherein the superior sealing portion includes a nose ridge region adapted to be positioned and seal along a nasal cartilage region which is above the pronasale and below a nasal bone region of the patient's nasal bridge.

3. The nasal mask according to claim 1, wherein the superior sealing portion includes a sides of nose region including a portion adapted to be positioned and seal substantially on the cartilaginous framework of the patient's nose along a region adjacent the junction between the nasal greater alar cartilage and the lateral nasal cartilage of the patient's nose.

4. The nasal mask according to claim 3, wherein the portion includes a wing or sealing flap that protrudes from an edge of the flexible membrane along its inner perimeter.

5. The nasal mask according to claim 4, wherein the wing or sealing flap is at least partially angled or pre-biased outwardly away from a breathing chamber provided by the nasal mask.

6. The nasal mask according to claim 1, wherein the sealing region includes a nose ridge region, sides of nose region, corners of nose region, and an upper lip region adapted to seal around both nares of the patient's nose.

7. The nasal mask according to claim 6, wherein the flexible membrane extends around an entire perimeter of the sealing region and the undercushion or backup band is only provided in the upper lip and corners of nose regions.

8. The nasal mask according to claim 7, wherein the flexible membrane and the undercushion or backup band provide a compression seal in the upper lip and corners of nose regions.

9. The nasal mask according to claim 7, wherein the flexible membrane in the nose ridge and sides of the nose regions is constructed and arranged to be in tension in use, and/or the flexible membrane is constructed and arranged such that a pressure within a breathing chamber provided by the nasal mask acts on the flexible membrane to provide a seal.

10. The nasal mask according to claim 6, wherein the contact area in the sides of nose region is relatively larger than the contact area in the nose ridge region.

11. The nasal mask according to claim 6, wherein the contact area includes a width extending from an inner edge along an edge of an orifice defined by the flexible membrane to an outer edge, and the width of the contact area in the nose ridge region is relatively narrower than the width of the contact area in the sides of nose region.

12. The nasal mask according to claim 1, wherein the superior sealing portion includes a nose ridge region including at least a portion that is locally saddle-shaped in curvature.

13. The nasal mask according to claim 1, wherein the inferior sealing portion includes an upper lip region including at least a portion that is locally saddle-shaped in curvature.

14. The nasal mask according to claim 1, wherein the superior sealing portion comprises a wing or sealing flap that protrudes from an edge of the flexible membrane along its inner perimeter, and the wing or sealing flap along with a curvature and a magnitude of the curvature of the flexible membrane around the perimeter of the sealing region form at least a portion of the first and second sealing mechanisms and determinative of the contact area of the sealing region in use.

15. A nasal mask system, comprising:

a cushion assembly including a sealing region having a nose ridge region, sides of nose region, corners of nose region, and a top lip region adapted to seal around both nares of a patient's nose, the nose ridge region adapted to be positioned and seal along a nasal cartilage region which is above the pronasale and below a nasal bone region of the patient's nasal bridge, and the sides of nose region is adapted to extend across the alar or flares of the patient's nose, the sealing region including a membrane that extends around an entire perimeter of the sealing region and an undercushion that is only provided in the top lip and corners of nose regions such that the sides of nose region includes a single layer or membrane only structure configured and arranged to seal along the alar or flares of the patient's nose and prevent excess pressure on the alar or flares of the patient's nose.

16. The nasal mask system according to claim 15, wherein the membrane and undercushion provide a compression seal in the top lip and corners of nose regions.

17. The nasal mask system according to claim 15, wherein the nose ridge and sides of the nose regions of the membrane is constructed and arranged to be in tension in use, and/or the membrane is constructed and arranged such that a pressure within a breathing chamber provided by the cushion assembly acts on the membrane to provide a seal.

18. The nasal mask system according to claim 15, wherein the sides of nose region includes a portion adapted to be positioned and seal substantially on the cartilaginous framework of the patient's nose along a region adjacent the junction between the nasal greater alar cartilage and the lateral nasal cartilage of the patient's nose.

19. The nasal mask system according to claim 18, wherein the portion includes a wing or sealing flap that protrudes from an edge of the membrane along its inner perimeter.

20. The nasal mask system according to claim 19, wherein the wing or sealing flap is at least partially angled or pre-biased outwardly away from a breathing chamber provided by the cushion assembly.

21. The nasal mask system according to claim 15, wherein the membrane has an edge that defines a T-shaped orifice.

22. The nasal mask system according to claim 15, wherein the nose ridge region includes at least a portion that is locally saddle-shaped in curvature.

23. The nasal mask system according to claim 15, wherein the top lip region includes at least a portion that is locally saddle-shaped in curvature.

24. A nasal mask system, comprising:

a cushion assembly including a sealing region adapted to seal around both nares of a patient's nose, an attachment region adapted to receive an elbow assembly, and a side wall region extending between the sealing region and the attachment region, the sealing region having a nose ridge region, sides of nose region, corners of nose region, and a top lip region, and the sealing region including a membrane that extends around an entire perimeter of the sealing region and an undercushion that is only provided in the top lip and corners of nose regions, the membrane and the undercushion in the top lip and corners of nose regions adapted to provide a compressive force in top lip and corners of nose regions of a patient's face in use, wherein the side wall region includes an area adjacent the top lip region of the sealing region, said area of the side wall region includes a cross-sectional wall thickness that is thinner than corresponding cross-sectional wall thicknesses of respective side wall regions adjacent the nose ridge, sides of nose, and corners of nose regions of the sealing region, wherein said area of thinner cross-sectional wall thickness is configured and arranged to lessen the compressive force provided by the membrane and the undercushion in the top lip region compared to the corners of nose region in order to avoid excessive pressure on the columella or septum of the patient's nose.

25. The nasal mask system according to claim 24, wherein the attachment region includes a decoupling portion having a cross-sectional wall thickness that is thinner than a corresponding cross-sectional wall thickness of an adjacent portion of the side wall region to permit decoupling of tube drag forces.

26. The nasal mask system according to claim 24, wherein the sides of nose region includes a portion adapted to be positioned and seal substantially on the cartilaginous framework of the patient's nose along a region adjacent the junction between the nasal greater alar cartilage and the lateral nasal cartilage of the patient's nose.

27. The nasal mask system according to claim 26, wherein the portion includes a wing or sealing flap that protrudes from an edge of the sealing region along its inner perimeter.

28. The nasal mask system according to claim 24, wherein, in a cross-sectional view through the nose ridge region and the top lip region, the sealing region includes a single layer or membrane only structure in the nose ridge region and a dual layer or membrane and undercushion structure in the top lip region.

29. A nasal mask system, comprising:
a cushion assembly including a sealing region having a nose ridge region, sides of nose region, corners of nose region, and a top lip region adapted to seal around both nares of a patient's nose,
the sides of nose region including a portion adapted to be positioned and seal substantially on the cartilaginous framework of the patient's nose along a region adjacent the junction between the nasal greater alar cartilage and the lateral nasal cartilage of the patient's nose,
wherein the sealing region includes a membrane that extends around an entire perimeter of the sealing region, and the portion includes a wing or sealing flap that protrudes from an edge of the membrane along its inner perimeter,
wherein the edge of the membrane along its inner perimeter along with an edge of each wing or sealing flap along its inner perimeter cooperate to define an orifice into a breathing chamber provided by the cushion assembly, and
wherein each wing or sealing flap is configured to extend outwardly at an incline from the edge of the membrane so that each wing or sealing flap is at least partially angled outwardly away from the breathing chamber before engagement with the patient's nose.

30. The nasal mask system according to claim 29, wherein the nasal mask system is constructed to have a seal-forming region that forms a seal along a nasal ridge without contacting a nasal bridge or the skin on the nasal bone.

31. The nasal mask system according to claim 29, wherein each wing or sealing flap is at least partially pre-biased outwardly away from the breathing chamber provided by the cushion assembly.

32. The nasal mask system according to claim 31, wherein the wing or sealing flap is adapted to deflect towards the breathing chamber when engaged with the patient's nose to provide a bias for sealing in the junction.

33. The nasal mask system according to claim 29, wherein the shape, flexibility, and pre-bias of the wing or sealing flap allows the wing or sealing flap to accommodate changes in curvature or contour in the junction so as to maintain seal and prevent leaks in use.

34. The nasal mask system according to claim 29, wherein the orifice is generally T-shaped.

35. The nasal mask system according to claim 34, wherein the generally T-shaped orifice includes an upper orifice portion and a lower orifice portion that extends generally transverse to the upper orifice portion.

36. The nasal mask system according to claim 34, wherein the wing or sealing flap changes a curvature and/or angle of the edge defining the generally T-shaped orifice.

37. The nasal mask system according to claim 36, wherein the edge of the generally T-shaped orifice curves upwardly and outwardly away from the breathing chamber at least along the wing or sealing flap.

38. The nasal mask system according to claim 29, wherein, in a cross-sectional view through the nose ridge region and the top lip region, the sealing region includes a single layer or membrane only structure in the nose ridge region and a dual layer or membrane and undercushion structure in the top lip region.

* * * * *